(12) United States Patent
Jiang et al.

(10) Patent No.: US 11,261,259 B2
(45) Date of Patent: Mar. 1, 2022

(54) ANTI-CLAUDIN 18.2 AND ANTI-4-1BB BISPECIFIC ANTIBODIES AND USES THEREOF

(71) Applicants: I-Mab Biopharma US Limited, Gaithersburg, MD (US); ABL Bio Inc., Seongnam-Si (KR)

(72) Inventors: Wenqing Jiang, Shanghai (CN); Lei Fang, Shanghai (CN); Zhengyi Wang, Shanghai (CN); Bingshi Guo, Shanghai (CN); Eunyoung Park, Seongnam-Si (KR); Eunsil Sung, Seongnam-Si (KR); Byungje Sung, Seongnam-Si (KR)

(73) Assignees: I-Mab Biopharma US Limited, Gaithersburg, MD (US); ABL Bio Inc., Seongnam-Si (KR)

(*) Notice: Subject to any disclaimer, the term of this patent is extended or adjusted under 35 U.S.C. 154(b) by 0 days.

(21) Appl. No.: 17/286,437

(22) PCT Filed: Aug. 12, 2020

(86) PCT No.: PCT/CN2020/108707
§ 371 (c)(1),
(2) Date: Apr. 16, 2021

(87) PCT Pub. No.: WO2021/027850
PCT Pub. Date: Feb. 18, 2021

(65) Prior Publication Data
US 2021/0317224 A1    Oct. 14, 2021

(30) Foreign Application Priority Data

| Aug. 12, 2019 | (WO) | PCT/CN2019/100162 |
| Sep. 5, 2019 | (WO) | PCT/CN2019/104508 |
| Jan. 14, 2020 | (WO) | PCT/CN2020/071954 |
| Apr. 30, 2020 | (WO) | PCT/CN2020/087968 |

(51) Int. Cl.
*C07K 16/28* (2006.01)
*A61P 35/00* (2006.01)
*A61K 39/00* (2006.01)

(52) U.S. Cl.
CPC .......... *C07K 16/2878* (2013.01); *A61P 35/00* (2018.01); *C07K 16/28* (2013.01); *A61K 2039/505* (2013.01); *C07K 2317/31* (2013.01); *C07K 2317/52* (2013.01); *C07K 2317/622* (2013.01); *C07K 2317/92* (2013.01)

(58) Field of Classification Search
None
See application file for complete search history.

(56) References Cited

FOREIGN PATENT DOCUMENTS

| WO | 2014075697 A1 | 5/2014 | |
| WO | 2014075788 A1 | 5/2014 | |
| WO | 2017143156 A1 | 8/2017 | |
| WO | 2018114748 A1 | 6/2018 | |
| WO | 2018114754 A1 | 6/2018 | |
| WO | 2018119001 A1 | 6/2018 | |
| WO | 2018140831 A1 | 8/2018 | |
| WO | WO 2018/140831 * | 8/2018 | ............. C07K 16/28 |
| WO | WO 2020/107715 * | 2/2019 | ............. C07K 16/46 |

OTHER PUBLICATIONS

International Search Report and Written Opinion for PCT/CN2020/108707 dated Nov. 19, 2020, 12 pages.
Jiang et al., "Claudin 18.2-Specific Chimeric Antigen Receptor Engineered T Cells for the Treatment of Gastric Cancer", Journal of the National Cancer Institute, vol. 111, No. 4, 2019, pp. 409-418.

* cited by examiner

*Primary Examiner* — Nelson B Moseley, II
(74) *Attorney, Agent, or Firm* — Sheppard Mullin Richter & Hampton LLP; Alex Nie

(57) ABSTRACT

Provided are bispecific and multi-specific antibodies that target both claudin 18.2 (CLDN18.2) and 4-1BB. These antibodies, in the absence of CLDN18.2-expressing cells, can bind to 4-1BB but are unable to activate 4-1BB signaling. In the presence of CLDN18.2-expressing cells, however, these antibodies can trigger CLDN18.2-dependent 4-1BB signaling, leading to potent immune response to the CLDN18.2-expressing tumor cells.

19 Claims, 20 Drawing Sheets

Specification includes a Sequence Listing.

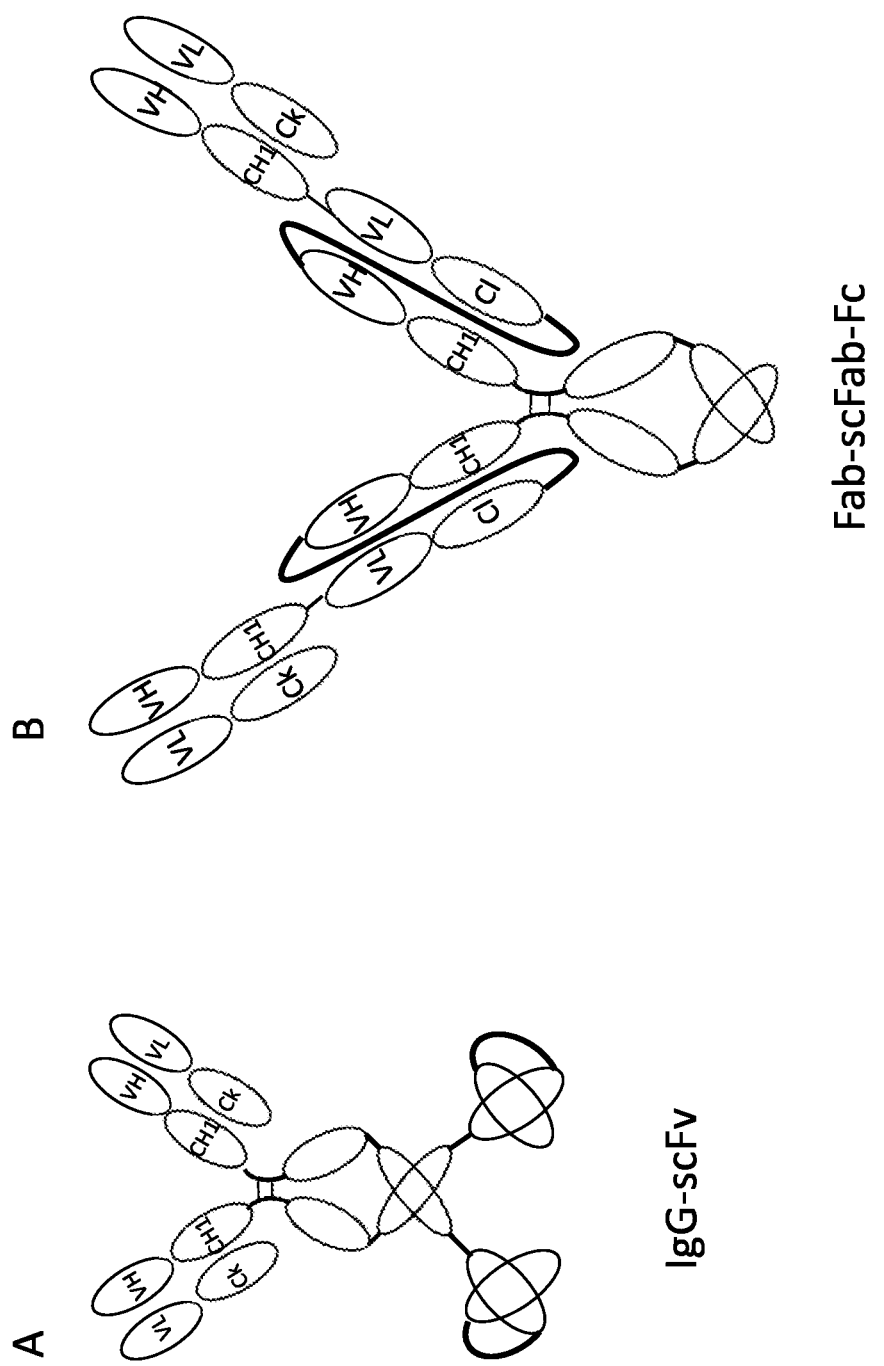
FIG. 1A-B

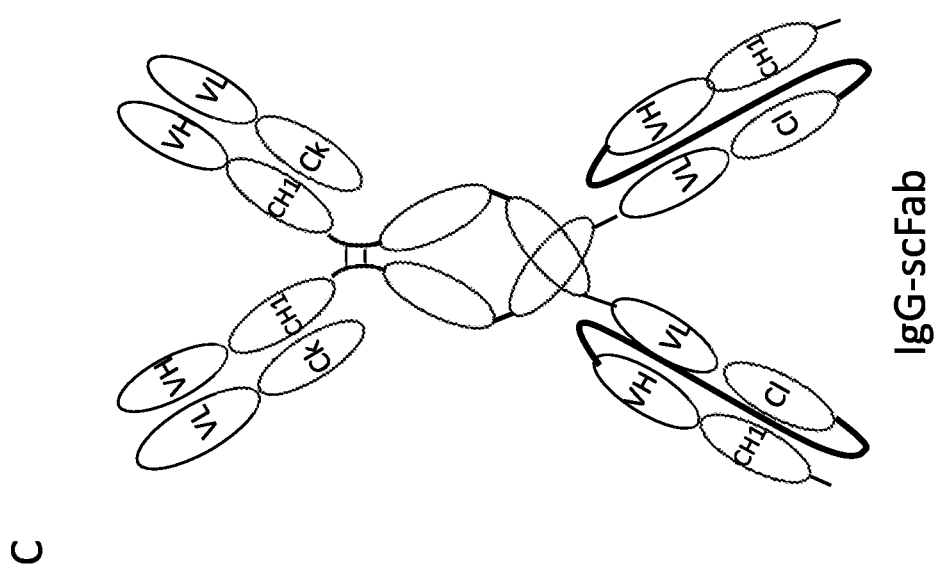

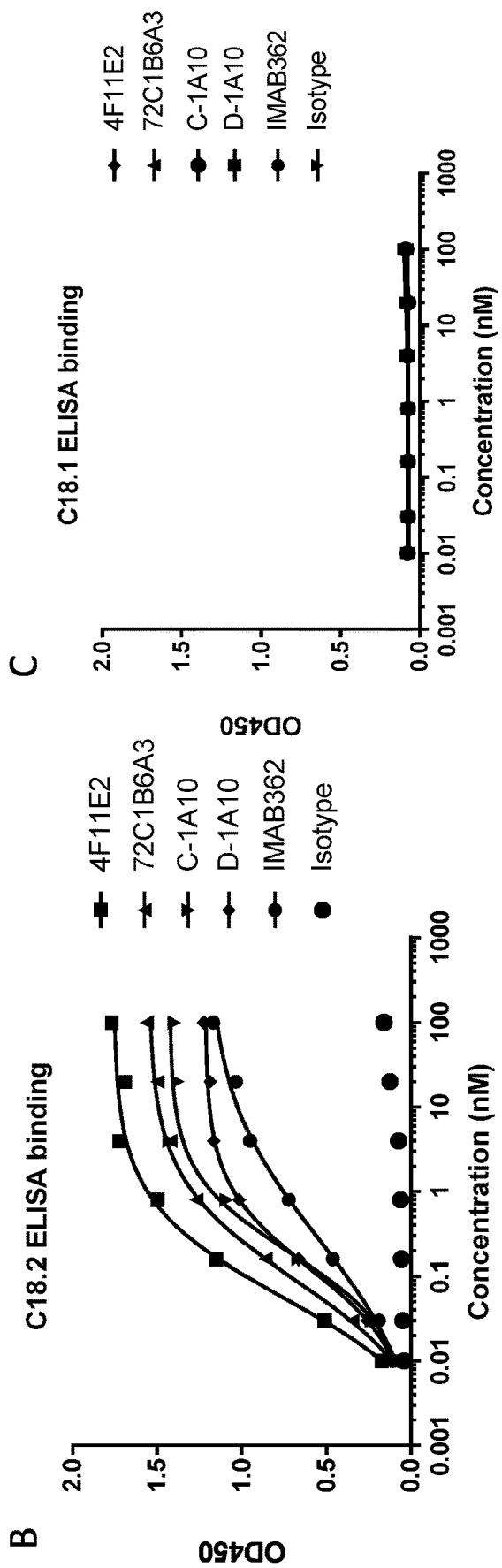
FIG. 2B-C

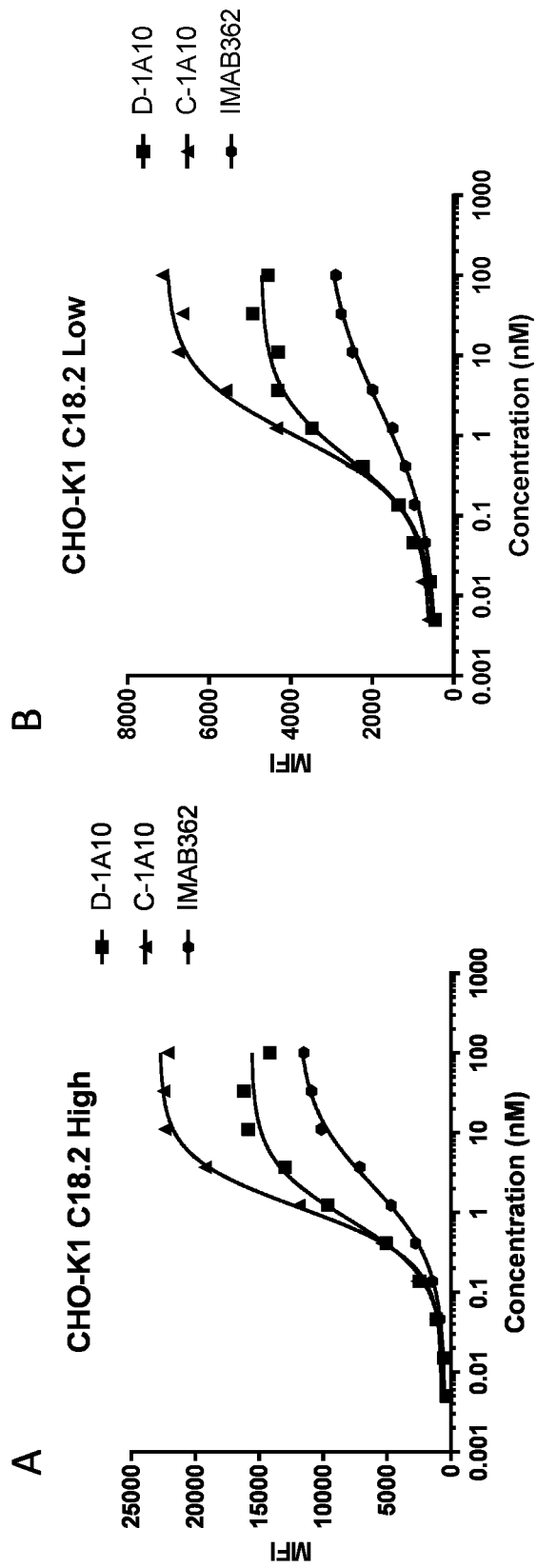
FIG. 4A-B

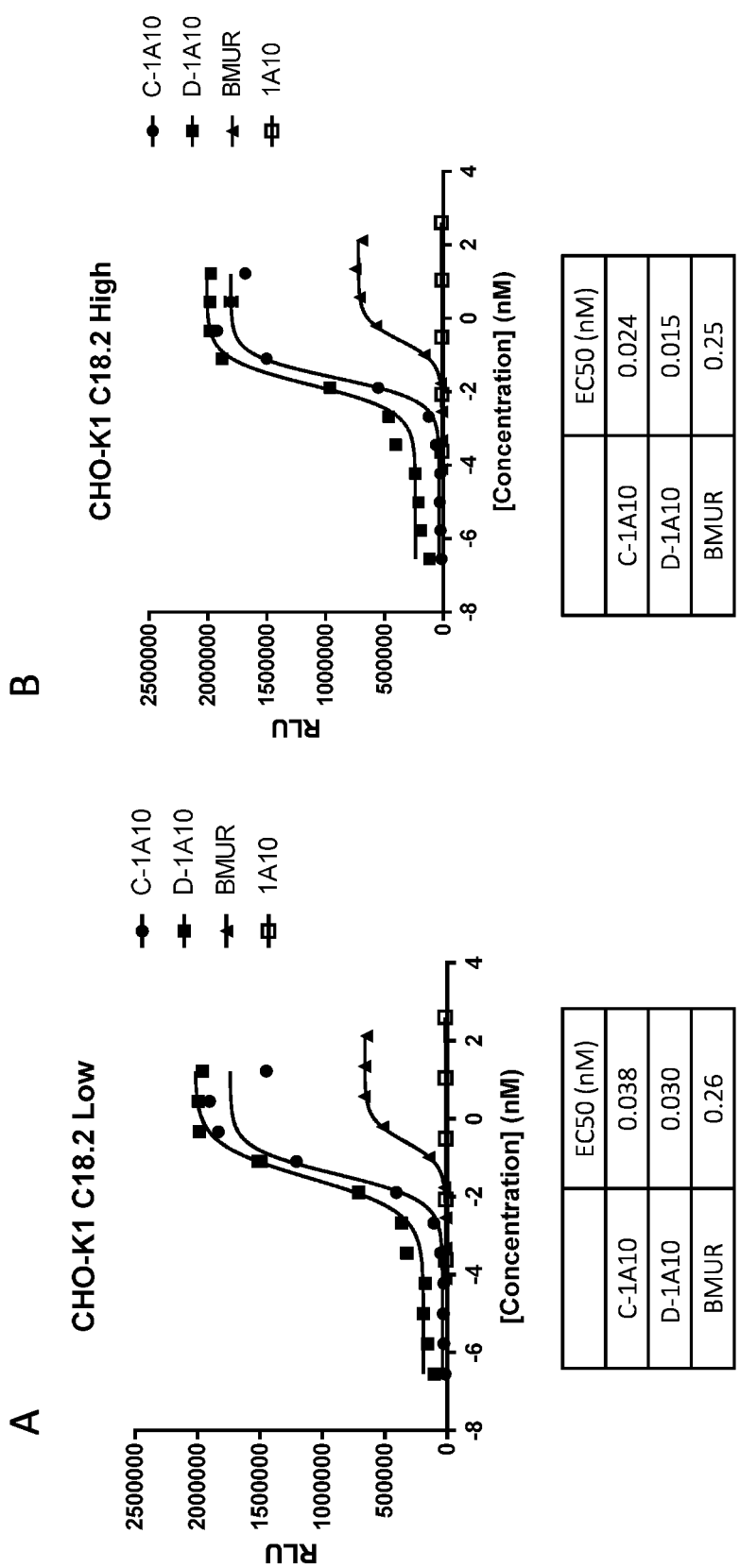
FIG. 5A-B

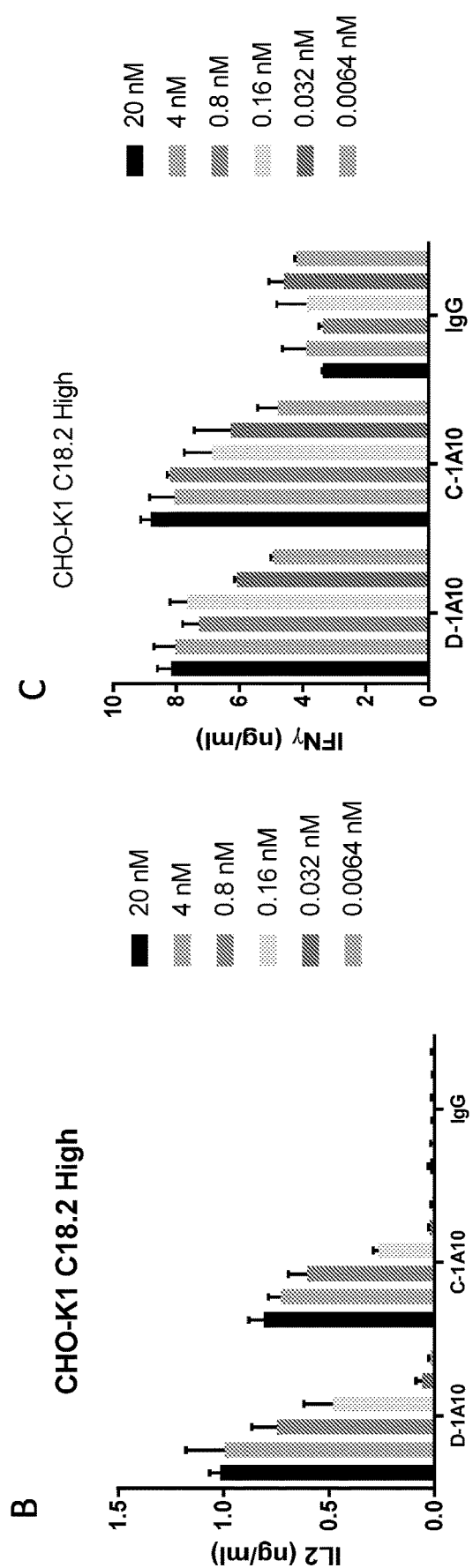
FIG. 6B-C

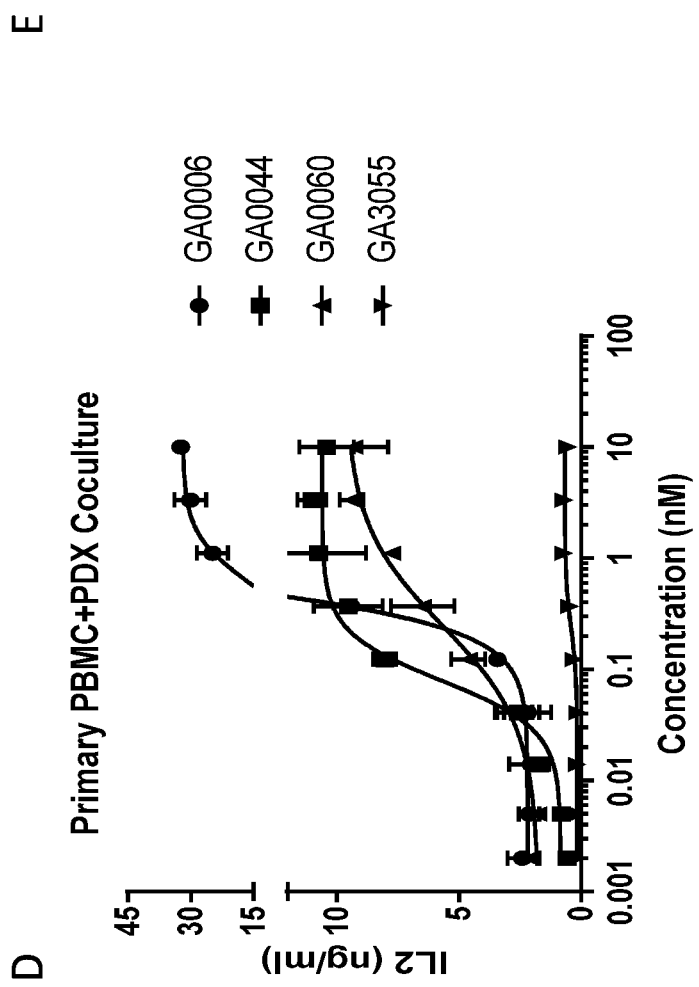
FIG. 6D-E

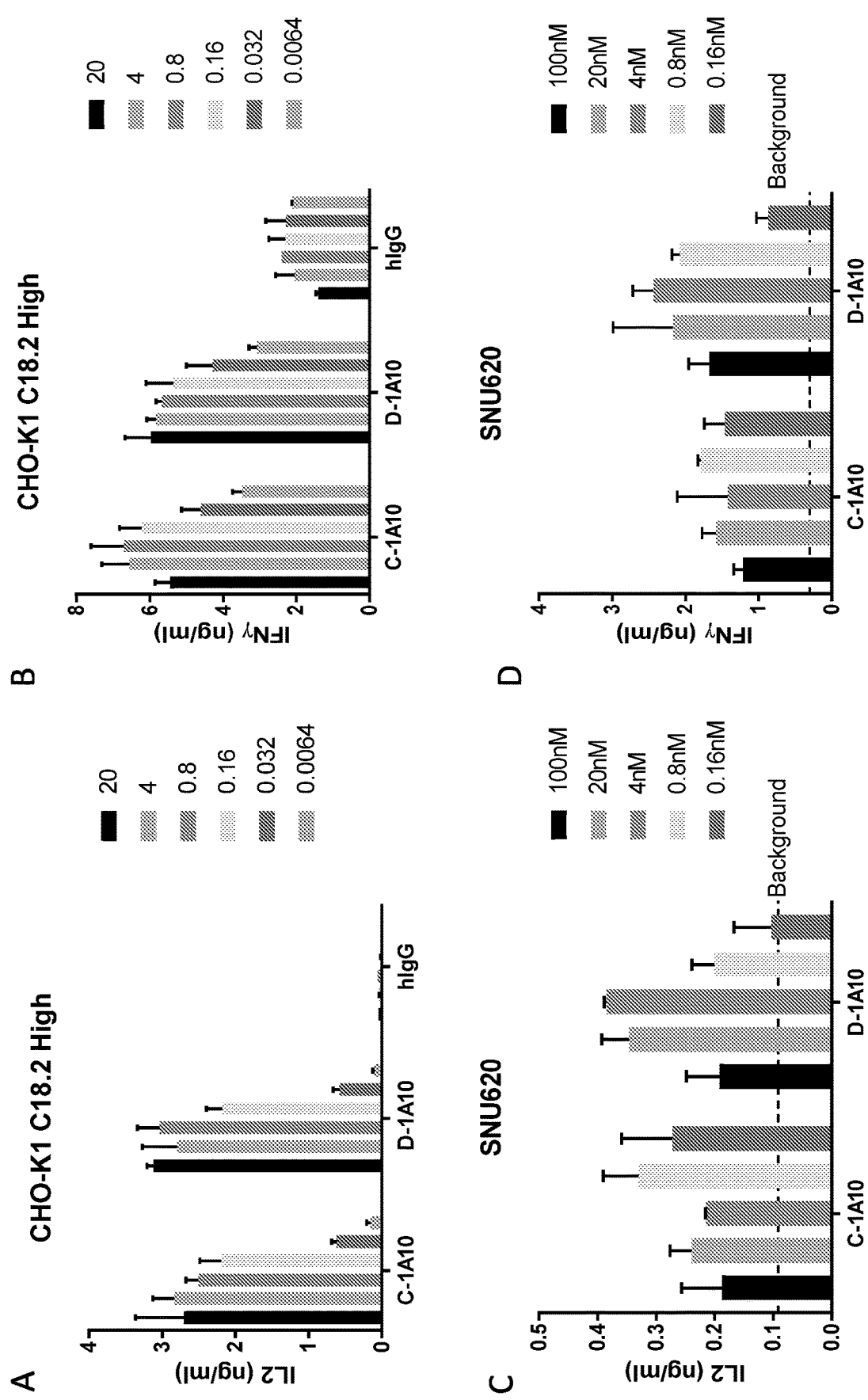
FIG. 7A-D

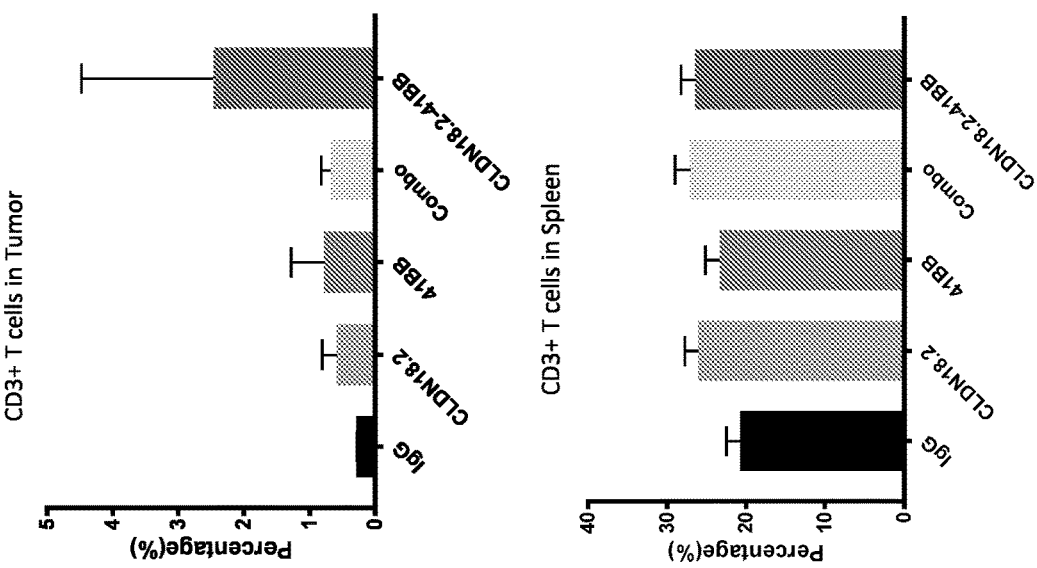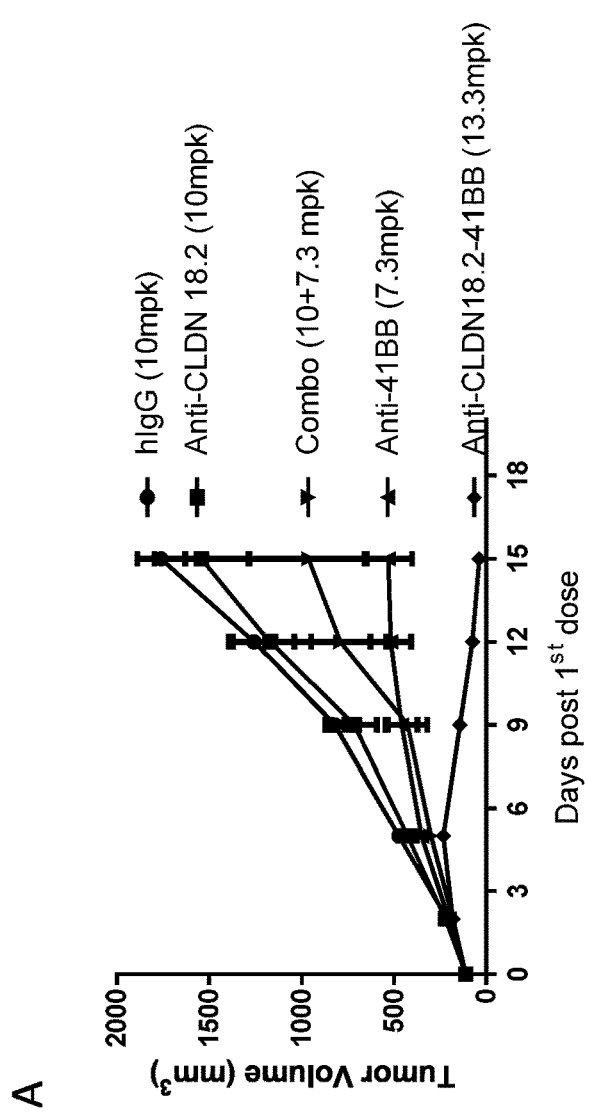
FIG. 8A-B

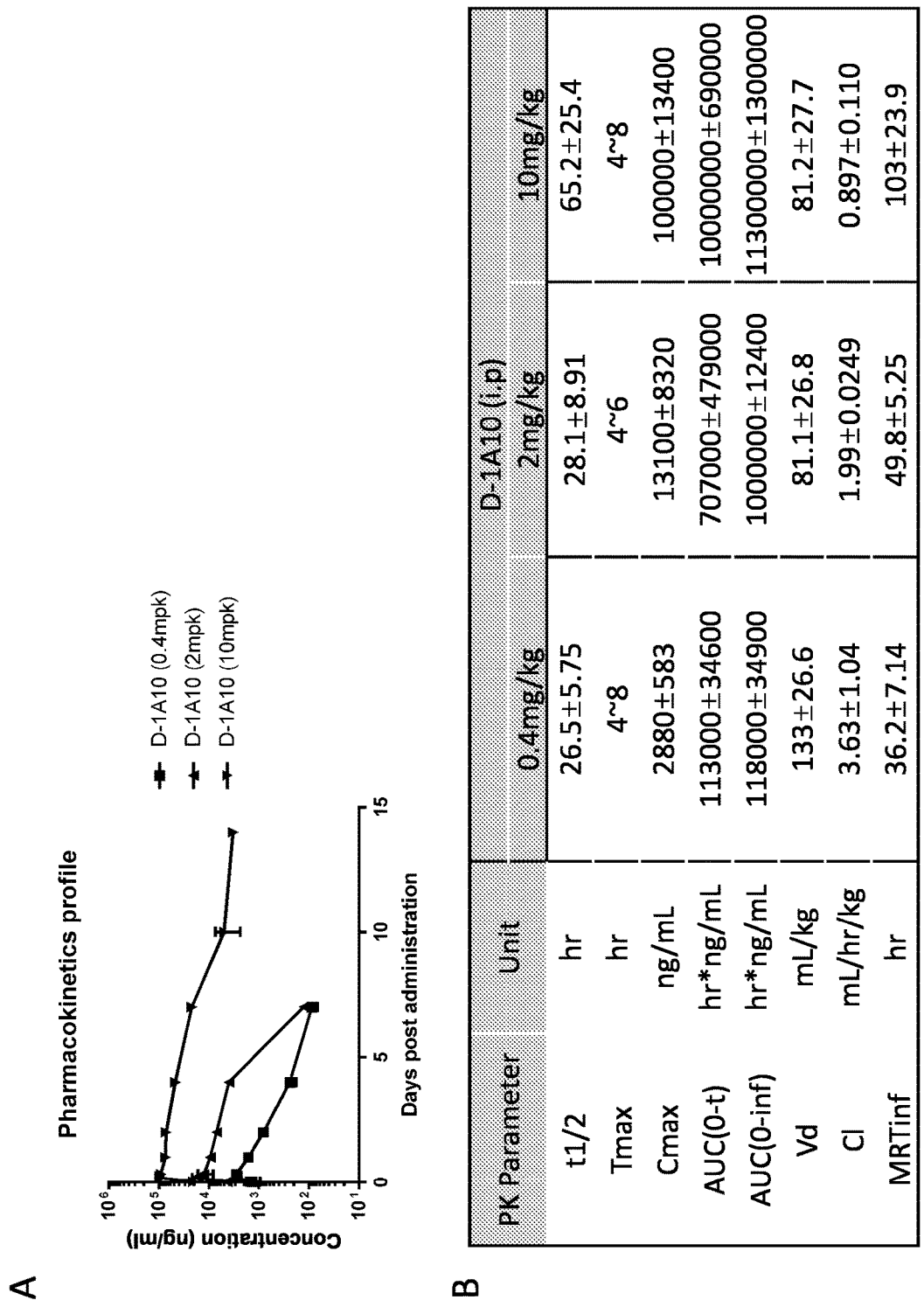
FIG. 11A-B

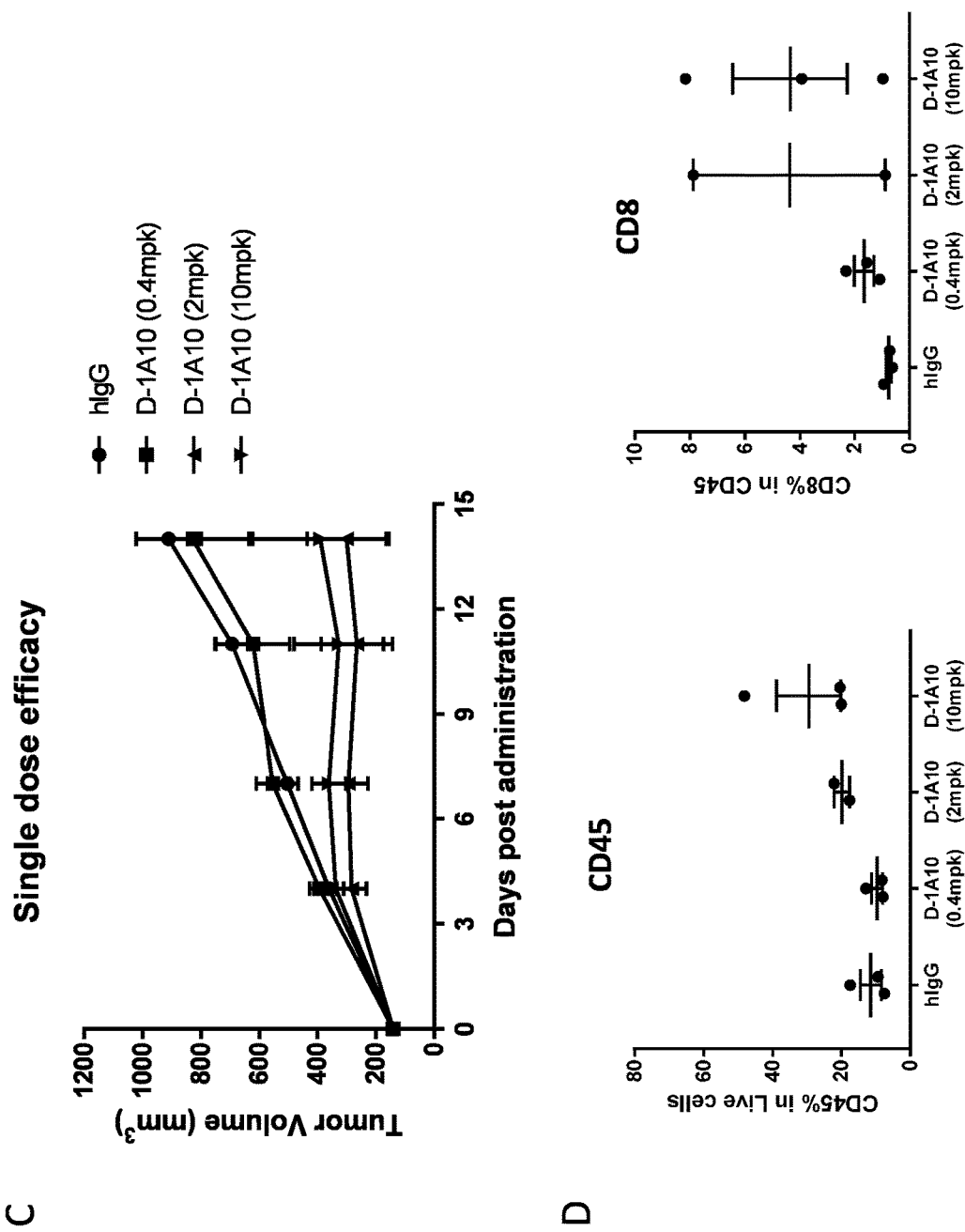
FIG. 11C-D

SEQUENCE LISTING

```
<160> NUMBER OF SEQ ID NOS: 74

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Ser Tyr Asp Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic

<400> SEQUENCE: 2
```

```
Trp Ile Ser Tyr Ser Gly Gly Ser Ile Tyr Tyr Ala Asp Ser Val Lys
1               5                   10                  15

Gly

<210> SEQ ID NO 3
<211> LENGTH: 12
<212> TYPE: PRT
<213> ORGANISM: Artificial Sequence
<220> FEATURE:
<223> OTHER INFORMATION: Synthetic

<400> SEQUENCE: 3

Asp Ala Gln Arg Asn Ser Met Arg Glu Phe Asp Tyr
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Synthetic

<400> SEQUENCE: 4

Ser Gly Ser Ser Ser Asn Ile Gly Asn Asn Tyr Val Thr
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Ala Asp Ser His Arg Pro Ser
1               5

<210> SEQ ID NO 6
<211> LENGTH: 11
<212> TYPE: PRT
<213> ORGANISM: Artificial Sequence
<220> FEATURE:
<223> OTHER INFORMATION: Synthetic

<400> SEQUENCE: 6

Ala Thr Trp Asp Tyr Ser Leu Ser Gly Tyr Val
1               5                   10

<210> SEQ ID NO 7
<211> LENGTH: 5
<212> TYPE: PRT
<213> ORGANISM: Artificial Sequence
<220> FEATURE:
<223> OTHER INFORMATION: Synthetic

<400> SEQUENCE: 7

Thr Phe Gly Met His
1               5

<210> SEQ ID NO 8
<211> LENGTH: 17
<212> TYPE: PRT
<213> ORGANISM: Artificial Sequence
<220> FEATURE:
<223> OTHER INFORMATION: Synthetic
```

```
<400> SEQUENCE: 8

Tyr Ile Thr Ser Gly Glu Ser Pro Ile Tyr Phe Thr Asp Thr Val Lys
1               5                   10                  15
Gly

<210> SEQ ID NO 9
<211> LENGTH: 10
<212> TYPE: PRT
<213> ORGANISM: Artificial Sequence
<220> FEATURE:
<223> OTHER INFORMATION: Synthetic

<400> SEQUENCE: 9

Ser Ser Tyr Tyr Gly Asn Ser Met Asp Tyr
1               5                   10

<210> SEQ ID NO 10
<211> LENGTH: 17
<212> TYPE: PRT
<213> ORGANISM: Artificial Sequence
<220> FEATURE:
<223> OTHER INFORMATION: Synthetic

<400> SEQUENCE: 10

Arg Ser Ser Gln Ser Leu Leu Asn Ala Gly Asn Arg Lys Asn Tyr Leu
1               5                   10                  15
Thr

<210> SEQ ID NO 11
<211> LENGTH: 7
<212> TYPE: PRT
<213> ORGANISM: Artificial Sequence
<220> FEATURE:
<223> OTHER INFORMATION: Synthetic

<400> SEQUENCE: 11

Trp Ala Ser Thr Arg Glu Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic

<400> SEQUENCE: 12

Gln Asn Ala Tyr Ser Tyr Pro Phe Thr
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic

<400> SEQUENCE: 13

Thr Tyr Pro Ile Glu
1               5

<210> SEQ ID NO 14
<211> LENGTH: 17
<212> TYPE: PRT
<213> ORGANISM: Artificial Sequence
```

```
<220> FEATURE:
<223> OTHER INFORMATION: Synthetic

<400> SEQUENCE: 14

Asn Phe His Pro Tyr Asn Asp Asp Thr Lys Tyr Asn Glu Lys Phe Lys
1               5                   10                  15

Gly

<210> SEQ ID NO 15
<211> LENGTH: 11
<212> TYPE: PRT
<213> ORGANISM: Artificial Sequence
<220> FEATURE:
<223> OTHER INFORMATION: Synthetic

<400> SEQUENCE: 15

Arg Ala Tyr Gly Tyr Pro Tyr Ala Met Asp Tyr
1               5                   10

<210> SEQ ID NO 16
<211> LENGTH: 17
<212> TYPE: PRT
<213> ORGANISM: Artificial Sequence
<220> FEATURE:
<223> OTHER INFORMATION: Synthetic

<400> SEQUENCE: 16

Lys Ser Ser Gln Ser Leu Leu Asn Ala Gly Asn Gln Lys Asn Tyr Leu
1               5                   10                  15

Thr

<210> SEQ ID NO 17
<211> LENGTH: 7
<212> TYPE: PRT
<213> ORGANISM: Artificial Sequence
<220> FEATURE:
<223> OTHER INFORMATION: Synthetic

<400> SEQUENCE: 17

Arg Ala Ser Ser Arg Glu Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic

<400> SEQUENCE: 18

Gln Asn Asp Tyr Ile Tyr Pro Tyr Thr
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic

<400> SEQUENCE: 19

Gly Tyr Ile Ile Gln
1               5

<210> SEQ ID NO 20
```

```
<211> LENGTH: 17
<212> TYPE: PRT
<213> ORGANISM: Artificial Sequence
<220> FEATURE:
<223> OTHER INFORMATION: Synthetic

<400> SEQUENCE: 20

Phe Ile Asn Pro Tyr Asn Asp Asp Thr Lys Tyr Asn Glu Gln Phe Lys
1               5                   10                  15

Gly

<210> SEQ ID NO 21
<211> LENGTH: 9
<212> TYPE: PRT
<213> ORGANISM: Artificial Sequence
<220> FEATURE:
<223> OTHER INFORMATION: Synthetic

<400> SEQUENCE: 21

Ala Tyr Phe Gly Asn Ala Phe Ala Tyr
1               5

<210> SEQ ID NO 22
<211> LENGTH: 17
<212> TYPE: PRT
<213> ORGANISM: Artificial Sequence
<220> FEATURE:
<223> OTHER INFORMATION: Synthetic

<400> SEQUENCE: 22

Lys Ser Ser Gln Ser Leu Leu Asn Ala Gly Asn Gln Lys Asn Tyr Leu
1               5                   10                  15

Thr

<210> SEQ ID NO 23
<211> LENGTH: 9
<212> TYPE: PRT
<213> ORGANISM: Artificial Sequence
<220> FEATURE:
<223> OTHER INFORMATION: Synthetic

<400> SEQUENCE: 23

Gln Asn Ala Tyr Tyr Phe Pro Phe Thr
1               5

<210> SEQ ID NO 24
<211> LENGTH: 121
<212> TYPE: PRT
<213> ORGANISM: Artificial Sequence
<220> FEATURE:
<223> OTHER INFORMATION: Synthetic

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Cys Leu Glu Trp Val
        35                  40                  45

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Asp Ala Gln Arg Asn Ser Met Arg Glu Phe Asp Tyr Trp Gly
            100                 105                 110

Gln Gly Thr Leu Val Thr Val Ser Ser
        115                 120

<210> SEQ ID NO 25
<211> LENGTH: 110
<212> TYPE: PRT
<213> ORGANISM: Artificial Sequence
<220> FEATURE:
<223> OTHER INFORMATION: Synthetic

<400> SEQUENCE: 25

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Tyr Val Thr Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Cys Gly Thr Lys Leu Thr Val Leu
            100                 105                 110

<210> SEQ ID NO 26
<211> LENGTH: 119
<212> TYPE: PRT
<213> ORGANISM: Artificial Sequence
<220> FEATURE:
<223> OTHER INFORMATION: Synthetic

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Phe
            20                  25                  30

Gly Met His Trp Val Arg Gln Ala Pro Gly Lys Gly Leu Glu Trp Val
        35                  40                  45

Ser Tyr Ile Thr Ser Gly Glu Ser Pro Ile Tyr Phe Thr Asp Thr Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Tyr Tyr Gly Asn Ser Met Asp Tyr Trp Gly Gln Gly
            100                 105                 110

Thr Leu Val Thr Val Ser Ser
        115

<210> SEQ ID NO 27
<211> LENGTH: 113
<212> TYPE: PRT
<213> ORGANISM: Artificial Sequence
```

-continued

<220> FEATURE:
<223> OTHER INFORMATION: Synthetic

<400> SEQUENCE: 27

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Leu Leu Asn Ala
            20                  25                  30

Gly Asn Arg Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ala Tyr Ser Tyr Pro Phe Thr Phe Gly Gly Gly Thr Lys Leu Glu Ile
            100                 105                 110

Lys

<210> SEQ ID NO 28
<211> LENGTH: 120
<212> TYPE: PRT
<213> ORGANISM: Artificial Sequence
<220> FEATURE:
<223> OTHER INFORMATION: Synthetic

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Pro Ile Glu Trp Val Arg Gln Ala Pro Gly Gln Arg Leu Glu Trp Met
        35                  40                  45

Gly Asn Phe His Pro Tyr Asn Asp Asp Thr Lys Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Ala Tyr Gly Tyr Pro Tyr Ala Met Asp Tyr Trp Gly Gln
            100                 105                 110

Gly Thr Leu Val Thr Val Ser Ser
        115                 120

<210> SEQ ID NO 29
<211> LENGTH: 113
<212> TYPE: PRT
<213> ORGANISM: Artificial Sequence
<220> FEATURE:
<223> OTHER INFORMATION: Synthetic

<400> SEQUENCE: 29

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ala
            20                  25                  30

Gly Asn Gln Lys Asn Tyr Leu Thr Trp Tyr Gln Gln Lys Pro Gly Gln

```
                35                  40                  45
Pro Pro Lys Leu Leu Ile Tyr Arg Ala Ser Ser Arg Glu Ser Gly Val
 50                  55                  60
Pro Asp Arg Phe Ser Gly Ser Gly Ser Gly Thr Asp Phe Thr Leu Thr
 65                  70                  75                  80
Ile Ser Ser Leu Gln Ala Glu Asp Val Ala Val Tyr Tyr Cys Gln Asn
                 85                  90                  95
Asp Tyr Ile Tyr Pro Tyr Thr Phe Gly Gly Gly Thr Lys Leu Glu Ile
                100                 105                 110
Lys

<210> SEQ ID NO 30
<211> LENGTH: 118
<212> TYPE: PRT
<213> ORGANISM: Artificial Sequence
<220> FEATURE:
<223> OTHER INFORMATION: Synthetic

<400> SEQUENCE: 30

Gln Val Gln Leu Val Gln Ser Gly Ala Glu Val Lys Lys Pro Gly Ala
 1               5                  10                  15
Ser Val Lys Val Ser Cys Lys Ala Ser Gly Tyr Thr Phe Thr Gly Tyr
                 20                  25                  30
Ile Ile Gln Trp Val Arg Gln Ala Pro Gly Gln Arg Leu Glu Trp Met
             35                  40                  45
Gly Phe Ile Asn Pro Tyr Asn Asp Asp Thr Lys Tyr Asn Glu Gln Phe
 50                  55                  60
Lys Gly Arg Val Thr Ile Thr Arg Asp Thr Ser Ala Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Ala Tyr Phe Gly Asn Ala Phe Ala Tyr Trp Gly Gln Gly Thr
                100                 105                 110
Leu Val Thr Val Ser Ser
        115

<210> SEQ ID NO 31
<211> LENGTH: 113
<212> TYPE: PRT
<213> ORGANISM: Artificial Sequence
<220> FEATURE:
<223> OTHER INFORMATION: Synthetic

<400> SEQUENCE: 31

Asp Ile Val Met Thr Gln Ser Pro Asp Ser Leu Ala Val Ser Leu Gly
 1               5                  10                  15
Glu Arg Ala Thr Ile Asn Cys Lys Ser Ser Gln Ser Leu Leu Asn Ala
                 20                  25                  30
Gly Asn Gln Lys Asn Tyr Leu Thr Trp Tyr Gln Gln Lys Pro Gly Gln
             35                  40                  45
Pro Pro Lys Leu Leu Ile Tyr Trp Ala Ser Thr Arg Glu Ser Gly Val
 50                  55                  60
Pro Asp Arg Phe Ser Gly Ser Gly Ser Gly Thr Asp Phe Thr Leu Thr
 65                  70                  75                  80
Ile Ser Ser Leu Gln Ala Glu Asp Val Ala Val Tyr Tyr Cys Gln Asn
                 85                  90                  95
Ala Tyr Tyr Phe Pro Phe Thr Phe Gly Gly Gly Thr Lys Leu Glu Ile
```

100    105    110

Lys

<210> SEQ ID NO 32
<211> LENGTH: 330
<212> TYPE: PRT
<213> ORGANISM: Artificial Sequence
<220> FEATURE:
<223> OTHER INFORMATION: Synthetic

<400> SEQUENCE: 32

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 33

```
<211> LENGTH: 107
<212> TYPE: PRT
<213> ORGANISM: Artificial Sequence
<220> FEATURE:
<223> OTHER INFORMATION: Synthetic

<400> SEQUENCE: 33

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 34
<211> LENGTH: 15
<212> TYPE: PRT
<213> ORGANISM: Artificial Sequence
<220> FEATURE:
<223> OTHER INFORMATION: Synthetic

<400> SEQUENCE: 34

Gly Gly Gly Gly Ser Gly Gly Gly Gly Ser Gly Gly Gly Gly Ser
1               5                   10                  15

<210> SEQ ID NO 35
<211> LENGTH: 20
<212> TYPE: PRT
<213> ORGANISM: Artificial Sequence
<220> FEATURE:
<223> OTHER INFORMATION: Synthetic

<400> SEQUENCE: 35

Gly Gly Gly Gly Ser Gly Gly Gly Gly Ser Gly Gly Gly Gly Ser Gly
1               5                   10                  15

Gly Gly Gly Ser
            20

<210> SEQ ID NO 36
<211> LENGTH: 103
<212> TYPE: PRT
<213> ORGANISM: Artificial Sequence
<220> FEATURE:
<223> OTHER INFORMATION: Synthetic

<400> SEQUENCE: 36

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 37
<211> LENGTH: 106
<212> TYPE: PRT
<213> ORGANISM: Artificial Sequence
<220> FEATURE:
<223> OTHER INFORMATION: Synthetic

<400> SEQUENCE: 37

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Gly Ser Pro
            35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 38
<211> LENGTH: 64
<212> TYPE: PRT
<213> ORGANISM: Artificial Sequence
<220> FEATURE:
<223> OTHER INFORMATION: Synthetic

<400> SEQUENCE: 38

Gly Ser Gly Ser Gly Ser Gly Ser Gly Ser Gly Ser Gly Ser Gly Ser
1               5                   10                  15

Gly Ser Gly Gly Gly Ser Gly Gly Gly Ser Gly Gly Gly Ser Gly Gly
                20                  25                  30

Ser Gly Gly Gly Ser Gly Gly Gly Ser Gly Gly Gly Ser Gly Gly Ser
            35                  40                  45

Gly Ser Gly Ser Gly Ser Gly Ser Gly Ser Gly Ser Gly Ser Gly Ser
    50                  55                  60

<210> SEQ ID NO 39
<211> LENGTH: 255
<212> TYPE: PRT
<213> ORGANISM: Artificial Sequence
<220> FEATURE:
<223> OTHER INFORMATION: Synthetic

<400> SEQUENCE: 39

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
                20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
                100                 105                 110

Thr Lys Lys Gly Cys Lys Asp Cys Cys Phe Gly Thr Phe Asn Asp Gln
                115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
                180                 185                 190

Ala Leu Thr Ser Thr Ala Leu Leu Phe Leu Leu Phe Phe Leu Thr Leu
                195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 40
<211> LENGTH: 715
<212> TYPE: PRT
<213> ORGANISM: Artificial Sequence
<220> FEATURE:
<223> OTHER INFORMATION: Synthetic

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Phe
                20                  25                  30

Gly Met His Trp Val Arg Gln Ala Pro Gly Lys Gly Leu Glu Trp Val
            35                  40                  45

Ser Tyr Ile Thr Ser Gly Glu Ser Pro Ile Tyr Phe Thr Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Tyr Tyr Gly Asn Ser Met Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

-continued

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Ala Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys Gly Gly Gly Gly Ser Gly Gly Gly Gly Ser Gly Gly Gly Gly Ser
        450                 455                 460

Gln Ser Val Leu Thr Gln Pro Pro Ser Ala Ser Gly Thr Pro Gly Gln
465                 470                 475                 480

Arg Val Thr Ile Ser Cys Ser Gly Ser Ser Asn Ile Gly Asn Asn
                485                 490                 495

Tyr Val Thr Trp Tyr Gln Gln Leu Pro Gly Thr Ala Pro Lys Leu Leu
            500                 505                 510

Ile Tyr Ala Asp Ser His Arg Pro Ser Gly Val Pro Asp Arg Phe Ser
        515                 520                 525

Gly Ser Lys Ser Gly Thr Ser Ala Ser Leu Ala Ile Ser Gly Leu Arg
    530                 535                 540

Ser Glu Asp Glu Ala Asp Tyr Tyr Cys Ala Thr Trp Asp Tyr Ser Leu
545                 550                 555                 560

Ser Gly Tyr Val Phe Gly Cys Gly Thr Lys Leu Thr Val Leu Gly Gly
```

```
                        565                 570                 575
Gly Gly Ser Gly Gly Gly Ser Gly Gly Gly Ser Gly Gly
            580                 585                 590
Gly Ser Glu Val Gln Leu Leu Glu Ser Gly Gly Leu Val Gln Pro
            595                 600                 605
Gly Gly Ser Leu Arg Leu Ser Cys Ala Ala Ser Gly Phe Thr Phe Ser
        610                 615                 620
Ser Tyr Asp Met Ser Trp Val Arg Gln Ala Pro Gly Lys Cys Leu Glu
625                 630                 635                 640
Trp Val Ser Trp Ile Ser Tyr Ser Gly Gly Ser Ile Tyr Tyr Ala Asp
                645                 650                 655
Ser Val Lys Gly Arg Phe Thr Ile Ser Arg Asp Asn Ser Lys Asn Thr
                660                 665                 670
Leu Tyr Leu Gln Met Asn Ser Leu Arg Ala Glu Asp Thr Ala Val Tyr
                675                 680                 685
Tyr Cys Ala Arg Asp Ala Gln Arg Asn Ser Met Arg Glu Phe Asp Tyr
            690                 695                 700
Trp Gly Gln Gly Thr Leu Val Thr Val Ser Ser
705                 710                 715

<210> SEQ ID NO 41
<211> LENGTH: 220
<212> TYPE: PRT
<213> ORGANISM: Artificial Sequence
<220> FEATURE:
<223> OTHER INFORMATION: Synthetic

<400> SEQUENCE: 41

Asp Ile Val Met Thr Gln Ser Pro Asp Ser Leu Ala Val Ser Leu Gly
1               5                   10                  15
Glu Arg Ala Thr Ile Asn Cys Arg Ser Ser Gln Ser Leu Leu Asn Ala
            20                  25                  30
Gly Asn Arg Lys Asn Tyr Leu Thr Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Asn
                85                  90                  95
Ala Tyr Ser Tyr Pro Phe Thr Phe Gly Gly Gly Thr Lys Leu Glu Ile
            100                 105                 110
Lys Arg Thr Val Ala Ala Pro Ser Val Phe Ile Phe Pro Pro Ser Asp
        115                 120                 125
Glu Gln Leu Lys Ser Gly Thr Ala Ser Val Val Cys Leu Leu Asn Asn
    130                 135                 140
Phe Tyr Pro Arg Glu Ala Lys Val Gln Trp Lys Val Asp Asn Ala Leu
145                 150                 155                 160
Gln Ser Gly Asn Ser Gln Glu Ser Val Thr Glu Gln Asp Ser Lys Asp
                165                 170                 175
Ser Thr Tyr Ser Leu Ser Ser Thr Leu Thr Leu Ser Lys Ala Asp Tyr
            180                 185                 190
Glu Lys His Lys Val Tyr Ala Cys Glu Val Thr His Gln Gly Leu Ser
        195                 200                 205
Ser Pro Val Thr Lys Ser Phe Asn Arg Gly Glu Cys
```

<210> SEQ ID NO 42
<211> LENGTH: 716
<212> TYPE: PRT
<213> ORGANISM: Artificial Sequence
<220> FEATURE:
<223> OTHER INFORMATION: Synthetic

<400> SEQUENCE: 42

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Pro Ile Glu Trp Val Arg Gln Ala Pro Gly Gln Arg Leu Glu Trp Met
        35                  40                  45

Gly Asn Phe His Pro Tyr Asn Asp Asp Thr Lys Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Ala Tyr Gly Tyr Pro Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
```

```
                    355                 360                 365
Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                    405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Gly Gly Gly Gly Ser Gly Gly Gly Ser Gly Gly Gly Gly
    450                 455                 460

Ser Gln Ser Val Leu Thr Gln Pro Pro Ser Ala Ser Gly Thr Pro Gly
465                 470                 475                 480

Gln Arg Val Thr Ile Ser Cys Ser Gly Ser Ser Ser Asn Ile Gly Asn
                    485                 490                 495

Asn Tyr Val Thr Trp Tyr Gln Gln Leu Pro Gly Thr Ala Pro Lys Leu
            500                 505                 510

Leu Ile Tyr Ala Asp Ser His Arg Pro Ser Gly Val Pro Asp Arg Phe
        515                 520                 525

Ser Gly Ser Lys Ser Gly Thr Ser Ala Ser Leu Ala Ile Ser Gly Leu
    530                 535                 540

Arg Ser Glu Asp Glu Ala Asp Tyr Tyr Cys Ala Thr Trp Asp Tyr Ser
545                 550                 555                 560

Leu Ser Gly Tyr Val Phe Gly Cys Gly Thr Lys Leu Thr Val Leu Gly
                    565                 570                 575

Gly Gly Gly Ser Gly Gly Gly Ser Gly Gly Gly Ser Gly Gly
            580                 585                 590

Gly Gly Ser Glu Val Gln Leu Leu Glu Ser Gly Gly Gly Leu Val Gln
        595                 600                 605

Pro Gly Gly Ser Leu Arg Leu Ser Cys Ala Ala Ser Gly Phe Thr Phe
    610                 615                 620

Ser Ser Tyr Asp Met Ser Trp Val Arg Gln Ala Pro Gly Lys Cys Leu
625                 630                 635                 640

Glu Trp Val Ser Trp Ile Ser Tyr Ser Gly Gly Ser Ile Tyr Tyr Ala
                    645                 650                 655

Asp Ser Val Lys Gly Arg Phe Thr Ile Ser Arg Asp Asn Ser Lys Asn
            660                 665                 670

Thr Leu Tyr Leu Gln Met Asn Ser Leu Arg Ala Glu Asp Thr Ala Val
        675                 680                 685

Tyr Tyr Cys Ala Arg Asp Ala Gln Arg Asn Ser Met Arg Glu Phe Asp
    690                 695                 700

Tyr Trp Gly Gln Gly Thr Leu Val Thr Val Ser Ser
705                 710                 715

<210> SEQ ID NO 43
<211> LENGTH: 220
<212> TYPE: PRT
<213> ORGANISM: Artificial Sequence
<220> FEATURE:
<223> OTHER INFORMATION: Synthetic

<400> SEQUENCE: 43

Asp Ile Val Met Thr Gln Ser Pro Asp Ser Leu Ala Val Ser Leu Gly
```

```
            1               5                  10                 15
        Glu Arg Ala Thr Ile Asn Cys Lys Ser Ser Gln Ser Leu Leu Asn Ala
                        20                 25                 30

Gly Asn Gln Lys Asn Tyr Leu Thr Trp Tyr Gln Gln Lys Pro Gly Gln
                    35                 40                 45

Pro Pro Lys Leu Leu Ile Tyr Arg Ala Ser Ser Arg Glu Ser Gly Val
                50                 55                 60

Pro Asp Arg Phe Ser Gly Ser Gly Ser Gly Thr Asp Phe Thr Leu Thr
        65                 70                 75                  80

Ile Ser Ser Leu Gln Ala Glu Asp Val Ala Val Tyr Tyr Cys Gln Asn
                        85                 90                 95

Asp Tyr Ile Tyr Pro Tyr Thr Phe Gly Gly Gly Thr Lys Leu Glu Ile
                    100                105                110

Lys Arg Thr Val Ala Ala Pro Ser Val Phe Ile Phe Pro Pro Ser Asp
                    115                120                125

Glu Gln Leu Lys Ser Gly Thr Ala Ser Val Val Cys Leu Leu Asn Asn
        130                135                140

Phe Tyr Pro Arg Glu Ala Lys Val Gln Trp Lys Val Asp Asn Ala Leu
        145                150                155                160

Gln Ser Gly Asn Ser Gln Glu Ser Val Thr Glu Gln Asp Ser Lys Asp
                        165                170                175

Ser Thr Tyr Ser Leu Ser Ser Thr Leu Thr Leu Ser Lys Ala Asp Tyr
                    180                185                190

Glu Lys His Lys Val Tyr Ala Cys Glu Val Thr His Gln Gly Leu Ser
                    195                200                205

Ser Pro Val Thr Lys Ser Phe Asn Arg Gly Glu Cys
                    210                215                220

<210> SEQ ID NO 44
<211> LENGTH: 714
<212> TYPE: PRT
<213> ORGANISM: Artificial Sequence
<220> FEATURE:
<223> OTHER INFORMATION: Synthetic

<400> SEQUENCE: 44

Gln Val Gln Leu Val Gln Ser Gly Ala Glu Val Lys Lys Pro Gly Ala
        1               5                  10                 15

Ser Val Lys Val Ser Cys Lys Ala Ser Gly Tyr Thr Phe Thr Gly Tyr
                        20                 25                 30

Ile Ile Gln Trp Val Arg Gln Ala Pro Gly Gln Arg Leu Glu Trp Met
                    35                 40                 45

Gly Phe Ile Asn Pro Tyr Asn Asp Asp Thr Lys Tyr Asn Glu Gln Phe
                50                 55                 60

Lys Gly Arg Val Thr Ile Thr Arg Asp Thr Ser Ala Ser Thr Ala Tyr
        65                 70                 75                  80

Met Glu Leu Ser Ser Leu Arg Ser Glu Asp Thr Ala Val Tyr Tyr Cys
                        85                 90                 95

Ala Arg Ala Tyr Phe Gly Asn Ala Phe Ala Tyr Trp Gly Gln Gly Thr
                    100                105                110

Leu Val Thr Val Ser Ser Ala Ser Thr Lys Gly Pro Ser Val Phe Pro
                    115                120                125

Leu Ala Pro Ser Ser Lys Ser Thr Ser Gly Gly Thr Ala Ala Leu Gly
        130                135                140

Cys Leu Val Lys Asp Tyr Phe Pro Glu Pro Val Thr Val Ser Trp Asn
```

```
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
                180                 185                 190
Ser Leu Gly Thr Gln Thr Tyr Ile Cys Asn Val Asn His Lys Pro Ser
                195                 200                 205
Asn Thr Lys Val Asp Lys Lys Val Glu Pro Lys Ser Cys Asp Lys Thr
            210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
                260                 265                 270
Glu Val Lys Phe Asn Trp Tyr Val Asp Gly Val Glu Val His Asn Ala
                275                 280                 285
Lys Thr Lys Pro Arg Glu Glu Gln Tyr Ala Ser Thr Tyr Arg Val Val
            290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
                340                 345                 350
Pro Pro Ser Arg Glu Glu Met Thr Lys Asn Gln Val Ser Leu Thr Cys
            355                 360                 365
Leu Val Lys Gly Phe Tyr Pro Ser Asp Ile Ala Val Glu Trp Glu Ser
                370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly Lys
            435                 440                 445
Gly Gly Gly Gly Ser Gly Gly Gly Ser Gly Gly Gly Ser Gly Gly Gln
450                 455                 460
Ser Val Leu Thr Gln Pro Pro Ser Ala Ser Gly Thr Pro Gly Gln Arg
465                 470                 475                 480
Val Thr Ile Ser Cys Ser Gly Ser Ser Asn Ile Gly Asn Asn Tyr
                485                 490                 495
Val Thr Trp Tyr Gln Gln Leu Pro Gly Thr Ala Pro Lys Leu Leu Ile
                500                 505                 510
Tyr Ala Asp Ser His Arg Pro Ser Gly Val Pro Asp Arg Phe Ser Gly
            515                 520                 525
Ser Lys Ser Gly Thr Ser Ala Ser Leu Ala Ile Ser Gly Leu Arg Ser
530                 535                 540
Glu Asp Glu Ala Asp Tyr Tyr Cys Ala Thr Trp Asp Tyr Ser Leu Ser
545                 550                 555                 560
Gly Tyr Val Phe Gly Cys Gly Thr Lys Leu Thr Val Leu Gly Gly Gly
                565                 570                 575
```

```
Gly Ser Gly Gly Gly Ser Gly Gly Gly Ser Gly Gly Gly
            580                 585                 590

Ser Glu Val Gln Leu Leu Glu Ser Gly Gly Gly Leu Val Gln Pro Gly
            595                 600                 605

Gly Ser Leu Arg Leu Ser Cys Ala Ala Ser Gly Phe Thr Phe Ser Ser
610                 615                 620

Tyr Asp Met Ser Trp Val Arg Gln Ala Pro Gly Lys Cys Leu Glu Trp
625                 630                 635                 640

Val Ser Trp Ile Ser Tyr Ser Gly Gly Ser Ile Tyr Tyr Ala Asp Ser
                    645                 650                 655

Val Lys Gly Arg Phe Thr Ile Ser Arg Asp Asn Ser Lys Asn Thr Leu
            660                 665                 670

Tyr Leu Gln Met Asn Ser Leu Arg Ala Glu Asp Thr Ala Val Tyr Tyr
            675                 680                 685

Cys Ala Arg Asp Ala Gln Arg Asn Ser Met Arg Glu Phe Asp Tyr Trp
            690                 695                 700

Gly Gln Gly Thr Leu Val Thr Val Ser Ser
705                 710

<210> SEQ ID NO 45
<211> LENGTH: 220
<212> TYPE: PRT
<213> ORGANISM: Artificial Sequence
<220> FEATURE:
<223> OTHER INFORMATION: Synthetic

<400> SEQUENCE: 45

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ala
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ala Tyr Tyr Phe Pro Phe Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 46
<211> LENGTH: 121
<212> TYPE: PRT
<213> ORGANISM: Artificial Sequence
<220> FEATURE:
<223> OTHER INFORMATION: Synthetic

<400> SEQUENCE: 46

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Tyr Ser Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gln Arg Asn Ser Met Arg Glu Phe Asp Tyr Trp Gly
            100                 105                 110

Gln Gly Thr Leu Val Thr Val Ser Ser
        115                 120
```

<210> SEQ ID NO 47
<211> LENGTH: 121
<212> TYPE: PRT
<213> ORGANISM: Artificial Sequence
<220> FEATURE:
<223> OTHER INFORMATION: Synthetic

<400> SEQUENCE: 47

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gln Arg Asn Ser Met Arg Glu Phe Asp Tyr Trp Gly
            100                 105                 110

Gln Gly Thr Leu Val Thr Val Ser Ser
        115                 120
```

<210> SEQ ID NO 48
<211> LENGTH: 121
<212> TYPE: PRT
<213> ORGANISM: Artificial Sequence
<220> FEATURE:
<223> OTHER INFORMATION: Synthetic

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gln Arg Gln Ser Met Arg Glu Phe Asp Tyr Trp Gly
            100                 105                 110

Gln Gly Thr Leu Val Thr Val Ser Ser
            115                 120

<210> SEQ ID NO 49
<211> LENGTH: 121
<212> TYPE: PRT
<213> ORGANISM: Artificial Sequence
<220> FEATURE:
<223> OTHER INFORMATION: Synthetic

<400> SEQUENCE: 49

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gln Arg Gln Ser Met Arg Glu Phe Asp Tyr Trp Gly
            100                 105                 110

Gln Gly Thr Leu Val Thr Val Ser Ser
            115                 120

<210> SEQ ID NO 50
<211> LENGTH: 121
<212> TYPE: PRT
<213> ORGANISM: Artificial Sequence
<220> FEATURE:
<223> OTHER INFORMATION: Synthetic

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gln Arg Asn Ala Met Arg Glu Phe Asp Tyr Trp Gly
            100                 105                 110

Gln Gly Thr Leu Val Thr Val Ser Ser
        115                 120

<210> SEQ ID NO 51
<211> LENGTH: 127
<212> TYPE: PRT
<213> ORGANISM: Artificial Sequence
<220> FEATURE:
<223> OTHER INFORMATION: Synthetic

<400> SEQUENCE: 51

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Asp Met Ser Trp Val Arg Gln Ala Pro Gly Lys Gly Leu Glu Trp Val
        35                  40                  45

Ser Val Ile Tyr Pro Asp Asp Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys His Gly Gly Gln Lys Pro Thr Thr Lys Ser Ser Ser Ala Tyr
            100                 105                 110

Gly Met Asp Gly Trp Gly Gln Gly Thr Leu Val Thr Val Ser Ser
        115                 120                 125

<210> SEQ ID NO 52
<211> LENGTH: 110
<212> TYPE: PRT
<213> ORGANISM: Artificial Sequence
<220> FEATURE:
<223> OTHER INFORMATION: Synthetic

<400> SEQUENCE: 52

Gln Ser Val Leu Thr Gln Pro Pro Ser Ala Ser Gly Thr Pro Gly Arg
1               5                   10                  15

Arg Val Thr Ile Ser Cys Ser Gly Ser Ser Ser Asn Ile Gly Asn Asn
            20                  25                  30

Tyr Val Thr Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Gly Gly Thr Lys Leu Thr Val Leu
            100                 105                 110

-continued

<210> SEQ ID NO 53
<211> LENGTH: 110
<212> TYPE: PRT
<213> ORGANISM: Artificial Sequence
<220> FEATURE:
<223> OTHER INFORMATION: Synthetic

<400> SEQUENCE: 53

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
                20                  25                  30

Tyr Val Thr Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Gly Gly Thr Lys Leu Thr Val Leu
            100                 105                 110
```

<210> SEQ ID NO 54
<211> LENGTH: 973
<212> TYPE: PRT
<213> ORGANISM: Artificial Sequence
<220> FEATURE:
<223> OTHER INFORMATION: Synthetic

<400> SEQUENCE: 54

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Phe
                20                  25                  30

Gly Met His Trp Val Arg Gln Ala Pro Gly Lys Gly Leu Glu Trp Val
            35                  40                  45

Ser Tyr Ile Thr Ser Gly Glu Ser Pro Ile Tyr Phe Thr Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Tyr Tyr Gly Asn Ser Met Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205
```

```
Ser Asn Thr Lys Val Asp Lys Lys Val Glu Pro Lys Ser Cys Gly Gly
    210                 215                 220

Gly Gly Ser Gly Gly Gly Gly Ser Gly Gly Gly Ser Gly Gly Gly Gly
225                 230                 235                 240

Gly Ser Gln Ser Val Leu Thr Gln Pro Pro Ser Ala Ser Gly Thr Pro
            245                 250                 255

Gly Gln Arg Val Thr Ile Ser Cys Ser Gly Ser Ser Asn Ile Gly
            260                 265                 270

Asn Asn Tyr Val Thr Trp Tyr Gln Gln Leu Pro Gly Thr Ala Pro Lys
        275                 280                 285

Leu Leu Ile Tyr Ala Asp Ser His Arg Pro Ser Gly Val Pro Asp Arg
    290                 295                 300

Phe Ser Gly Ser Lys Ser Gly Thr Ser Ala Ser Leu Ala Ile Ser Gly
305                 310                 315                 320

Leu Arg Ser Glu Asp Glu Ala Asp Tyr Tyr Cys Ala Thr Trp Asp Tyr
            325                 330                 335

Ser Leu Ser Gly Tyr Val Phe Gly Gly Gly Thr Lys Leu Thr Val Leu
            340                 345                 350

Gly Gln Pro Lys Ala Asn Pro Thr Val Thr Leu Phe Pro Pro Ser Ser
        355                 360                 365

Glu Glu Leu Gln Ala Asn Lys Ala Thr Leu Val Cys Leu Ile Ser Asp
370                 375                 380

Phe Tyr Pro Gly Ala Val Thr Val Ala Trp Lys Ala Asp Gly Ser Pro
385                 390                 395                 400

Val Lys Ala Gly Val Glu Thr Thr Lys Pro Ser Lys Gln Ser Asn Asn
            405                 410                 415

Lys Tyr Ala Ala Ser Ser Tyr Leu Ser Leu Thr Pro Glu Gln Trp Lys
        420                 425                 430

Ser His Arg Ser Tyr Ser Cys Gln Val Thr His Glu Gly Ser Thr Val
    435                 440                 445

Glu Lys Thr Val Ala Pro Thr Glu Cys Ser Gly Ser Gly Ser Gly Ser
450                 455                 460

Gly Ser Gly Ser Gly Ser Gly Ser Gly Ser Gly Gly Gly Gly
465                 470                 475                 480

Ser Gly Gly Gly Gly Ser Gly Gly Gly Gly Ser Gly Gly Gly Gly Ser
            485                 490                 495

Gly Gly Gly Gly Ser Gly Gly Gly Ser Gly Ser Gly Ser Gly Ser
                500                 505                 510

Gly Ser Gly Ser Gly Ser Gly Ser Glu Val Gln Leu Leu Glu
        515                 520                 525

Ser Gly Gly Gly Leu Val Gln Pro Gly Gly Ser Leu Arg Leu Ser Cys
530                 535                 540

Ala Ala Ser Gly Phe Thr Phe Ser Ser Tyr Asp Met Ser Trp Val Arg
545                 550                 555                 560

Gln Ala Pro Gly Lys Gly Leu Glu Trp Val Ser Trp Ile Ser Tyr Ser
            565                 570                 575

Gly Gly Ser Ile Tyr Tyr Ala Asp Ser Val Lys Gly Arg Phe Thr Ile
            580                 585                 590

Ser Arg Asp Asn Ser Lys Asn Thr Leu Tyr Leu Gln Met Asn Ser Leu
        595                 600                 605

Arg Ala Glu Asp Thr Ala Val Tyr Tyr Cys Ala Arg Asp Ala Gln Arg
    610                 615                 620

Asn Ser Met Arg Glu Phe Asp Tyr Trp Gly Gln Gly Thr Leu Val Thr
```

```
                625                 630                 635                 640
Val Ser Ser Ala Ser Thr Lys Gly Pro Ser Val Phe Pro Leu Ala Pro
                645                 650                 655

Ser Ser Lys Ser Thr Ser Gly Gly Thr Ala Ala Leu Gly Cys Leu Val
            660                 665                 670

Lys Asp Tyr Phe Pro Glu Pro Val Thr Val Ser Trp Asn Ser Gly Ala
        675                 680                 685

Leu Thr Ser Gly Val His Thr Phe Pro Ala Val Leu Gln Ser Ser Gly
    690                 695                 700

Leu Tyr Ser Leu Ser Ser Val Val Thr Val Pro Ser Ser Ser Leu Gly
705                 710                 715                 720

Thr Gln Thr Tyr Ile Cys Asn Val Asn His Lys Pro Ser Asn Thr Lys
                725                 730                 735

Val Asp Lys Lys Val Glu Pro Lys Ser Cys Asp Lys Thr His Thr Cys
            740                 745                 750

Pro Pro Cys Pro Ala Pro Glu Leu Leu Gly Gly Pro Ser Val Phe Leu
        755                 760                 765

Phe Pro Pro Lys Pro Lys Asp Thr Leu Met Ile Ser Arg Thr Pro Glu
    770                 775                 780

Val Thr Cys Val Val Val Asp Val Ser His Glu Asp Pro Glu Val Lys
785                 790                 795                 800

Phe Asn Trp Tyr Val Asp Gly Val Glu Val His Asn Ala Lys Thr Lys
                805                 810                 815

Pro Arg Glu Glu Gln Tyr Ala Ser Thr Tyr Arg Val Val Ser Val Leu
            820                 825                 830

Thr Val Leu His Gln Asp Trp Leu Asn Gly Lys Glu Tyr Lys Cys Lys
        835                 840                 845

Val Ser Asn Lys Ala Leu Pro Ala Pro Ile Glu Lys Thr Ile Ser Lys
    850                 855                 860

Ala Lys Gly Gln Pro Arg Glu Pro Gln Val Tyr Thr Leu Pro Pro Ser
865                 870                 875                 880

Arg Glu Glu Met Thr Lys Asn Gln Val Ser Leu Thr Cys Leu Val Lys
                885                 890                 895

Gly Phe Tyr Pro Ser Asp Ile Ala Val Glu Trp Glu Ser Asn Gly Gln
            900                 905                 910

Pro Glu Asn Asn Tyr Lys Thr Thr Pro Pro Val Leu Asp Ser Asp Gly
        915                 920                 925

Ser Phe Phe Leu Tyr Ser Lys Leu Thr Val Asp Lys Ser Arg Trp Gln
    930                 935                 940

Gln Gly Asn Val Phe Ser Cys Ser Val Met His Glu Ala Leu His Asn
945                 950                 955                 960

His Tyr Thr Gln Lys Ser Leu Ser Leu Ser Pro Gly Lys
                965                 970

<210> SEQ ID NO 55
<211> LENGTH: 968
<212> TYPE: PRT
<213> ORGANISM: Artificial Sequence
<220> FEATURE:
<223> OTHER INFORMATION: Synthetic

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Phe
```

-continued

```
                20                  25                  30
Gly Met His Trp Val Arg Gln Ala Pro Gly Lys Gly Leu Glu Trp Val
             35                  40                  45
Ser Tyr Ile Thr Ser Gly Glu Ser Pro Ile Tyr Phe Thr Asp Thr Val
 50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg Ser Ser Tyr Tyr Gly Asn Ser Met Asp Tyr Trp Gly Gln Gly
                100                 105                 110
Thr Leu Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
        130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Ala Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
```

```
Lys Gly Gly Gly Ser Gly Gly Gly Ser Gly Gly Gly Ser
    450                 455                 460
Gln Ser Val Leu Thr Gln Pro Pro Ser Ala Ser Gly Thr Pro Gly Gln
465                 470                 475                 480
Arg Val Thr Ile Ser Cys Ser Gly Ser Ser Asn Ile Gly Asn Asn
                    485                 490                 495
Tyr Val Thr Trp Tyr Gln Gln Leu Pro Gly Thr Ala Pro Lys Leu Leu
                500                 505                 510
Ile Tyr Ala Asp Ser His Arg Pro Ser Gly Val Pro Asp Arg Phe Ser
                515                 520                 525
Gly Ser Lys Ser Gly Thr Ser Ala Ser Leu Ala Ile Ser Gly Leu Arg
    530                 535                 540
Ser Glu Asp Glu Ala Asp Tyr Tyr Cys Ala Thr Trp Asp Tyr Ser Leu
545                 550                 555                 560
Ser Gly Tyr Val Phe Gly Gly Gly Thr Lys Leu Thr Val Leu Gly Gln
                565                 570                 575
Pro Lys Ala Asn Pro Thr Val Thr Leu Phe Pro Pro Ser Ser Glu Glu
                580                 585                 590
Leu Gln Ala Asn Lys Ala Thr Leu Val Cys Leu Ile Ser Asp Phe Tyr
                595                 600                 605
Pro Gly Ala Val Thr Val Ala Trp Lys Ala Asp Gly Ser Pro Val Lys
    610                 615                 620
Ala Gly Val Glu Thr Thr Lys Pro Ser Lys Gln Ser Asn Asn Lys Tyr
625                 630                 635                 640
Ala Ala Ser Ser Tyr Leu Ser Leu Thr Pro Glu Gln Trp Lys Ser His
                645                 650                 655
Arg Ser Tyr Ser Cys Gln Val Thr His Glu Gly Ser Thr Val Glu Lys
                660                 665                 670
Thr Val Ala Pro Thr Glu Cys Ser Gly Ser Gly Ser Gly Ser Gly Ser
                675                 680                 685
Gly Ser Gly Ser Gly Ser Gly Ser Gly Ser Gly Gly Gly Ser Gly
    690                 695                 700
Gly Gly Gly Ser Gly Gly Gly Ser Gly Gly Gly Ser Gly Gly
705                 710                 715                 720
Gly Gly Ser Gly Gly Gly Ser Gly Ser Gly Ser Gly Ser
                725                 730                 735
Gly Ser Gly Ser Gly Ser Gly Ser Glu Val Gln Leu Leu Glu Ser Gly
                740                 745                 750
Gly Gly Leu Val Gln Pro Gly Gly Ser Leu Arg Leu Ser Cys Ala Ala
                755                 760                 765
Ser Gly Phe Thr Phe Ser Ser Tyr Asp Met Ser Trp Val Arg Gln Ala
                770                 775                 780
Pro Gly Lys Gly Leu Glu Trp Val Ser Trp Ile Ser Tyr Ser Gly Gly
785                 790                 795                 800
Ser Ile Tyr Tyr Ala Asp Ser Val Lys Gly Arg Phe Thr Ile Ser Arg
                805                 810                 815
Asp Asn Ser Lys Asn Thr Leu Tyr Leu Gln Met Asn Ser Leu Arg Ala
                820                 825                 830
Glu Asp Thr Ala Val Tyr Tyr Cys Ala Arg Asp Ala Gln Arg Asn Ser
                835                 840                 845
Met Arg Glu Phe Asp Tyr Trp Gly Gln Gly Thr Leu Val Thr Val Ser
    850                 855                 860
```

Ser Ala Ser Thr Lys Gly Pro Ser Val Phe Pro Leu Ala Pro Ser Ser
865                 870                 875                 880

Lys Ser Thr Ser Gly Gly Thr Ala Ala Leu Gly Cys Leu Val Lys Asp
            885                 890                 895

Tyr Phe Pro Glu Pro Val Thr Val Ser Trp Asn Ser Gly Ala Leu Thr
        900                 905                 910

Ser Gly Val His Thr Phe Pro Ala Val Leu Gln Ser Ser Gly Leu Tyr
        915                 920                 925

Ser Leu Ser Ser Val Val Thr Val Pro Ser Ser Ser Leu Gly Thr Gln
        930                 935                 940

Thr Tyr Ile Cys Asn Val Asn His Lys Pro Ser Asn Thr Lys Val Asp
945                 950                 955                 960

Lys Lys Val Glu Pro Lys Ser Cys
                965

<210> SEQ ID NO 56
<211> LENGTH: 12
<212> TYPE: PRT
<213> ORGANISM: Artificial Sequence
<220> FEATURE:
<223> OTHER INFORMATION: Synthetic

<400> SEQUENCE: 56

Asp Gly Gln Arg Asn Ser Met Arg Glu Phe Asp Tyr
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Synthetic

<400> SEQUENCE: 57

Asp Ala Gln Arg Gln Ser Met Arg Glu Phe Asp Tyr
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Synthetic

<400> SEQUENCE: 58

Asp Gly Gln Arg Gln Ser Met Arg Glu Phe Asp Tyr
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Synthetic

<400> SEQUENCE: 59

Asp Ala Gln Arg Asn Ala Met Arg Glu Phe Asp Tyr
1               5                   10

<210> SEQ ID NO 60
<211> LENGTH: 5
<212> TYPE: PRT
<213> ORGANISM: Artificial Sequence
<220> FEATURE:

<223> OTHER INFORMATION: Synthetic

<400> SEQUENCE: 60

Gly Tyr Asp Met Ser
1               5

<210> SEQ ID NO 61
<211> LENGTH: 17
<212> TYPE: PRT
<213> ORGANISM: Artificial Sequence
<220> FEATURE:
<223> OTHER INFORMATION: Synthetic

<400> SEQUENCE: 61

Val Ile Tyr Pro Asp Asp Gly Asn Thr Tyr Tyr Ala Asp Ser Val Lys
1               5                   10                  15

Gly

<210> SEQ ID NO 62
<211> LENGTH: 18
<212> TYPE: PRT
<213> ORGANISM: Artificial Sequence
<220> FEATURE:
<223> OTHER INFORMATION: Synthetic

<400> SEQUENCE: 62

His Gly Gly Gln Lys Pro Thr Thr Lys Ser Ser Ala Tyr Gly Met
1               5                   10                  15

Asp Gly

<210> SEQ ID NO 63
<211> LENGTH: 121
<212> TYPE: PRT
<213> ORGANISM: Artificial Sequence
<220> FEATURE:
<223> OTHER INFORMATION: Synthetic

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Cys Leu Glu Trp Val
        35                  40                  45

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gln Arg Asn Ser Met Arg Glu Phe Asp Tyr Trp Gly
            100                 105                 110

Gln Gly Thr Leu Val Thr Val Ser Ser
        115                 120

<210> SEQ ID NO 64
<211> LENGTH: 121
<212> TYPE: PRT
<213> ORGANISM: Artificial Sequence
<220> FEATURE:
<223> OTHER INFORMATION: Synthetic

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Cys Leu Glu Trp Val
        35                  40                  45

Ser Trp Ile Ser Tyr Ser Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gln Arg Asn Ser Met Arg Glu Phe Asp Tyr Trp Gly
            100                 105                 110

Gln Gly Thr Leu Val Thr Val Ser Ser
        115                 120

<210> SEQ ID NO 65
<211> LENGTH: 121
<212> TYPE: PRT
<213> ORGANISM: Artificial Sequence
<220> FEATURE:
<223> OTHER INFORMATION: Synthetic

<400> SEQUENCE: 65

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Cys Leu Glu Trp Val
        35                  40                  45

Ser Trp Ile Ser Tyr Ser Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gln Arg Asn Ser Met Arg Glu Phe Asp Tyr Trp Gly
            100                 105                 110

Gln Gly Thr Leu Val Thr Val Ser Ser
        115                 120

<210> SEQ ID NO 66
<211> LENGTH: 121
<212> TYPE: PRT
<213> ORGANISM: Artificial Sequence
<220> FEATURE:
<223> OTHER INFORMATION: Synthetic

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Cys Leu Glu Trp Val
        35                  40                  45

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gln Arg Gln Ser Met Arg Glu Phe Asp Tyr Trp Gly
                100                 105                 110

Gln Gly Thr Leu Val Thr Val Ser Ser
            115                 120

<210> SEQ ID NO 67
<211> LENGTH: 127
<212> TYPE: PRT
<213> ORGANISM: Artificial Sequence
<220> FEATURE:
<223> OTHER INFORMATION: Synthetic

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Asp Met Ser Trp Val Arg Gln Ala Pro Gly Lys Cys Leu Glu Trp Val
        35                  40                  45

Ser Val Ile Tyr Pro Asp Asp Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys His Gly Gly Gln Lys Pro Thr Thr Lys Ser Ser Ser Ala Tyr
                100                 105                 110

Gly Met Asp Gly Trp Gly Gln Gly Thr Leu Val Thr Val Ser Ser
            115                 120                 125

<210> SEQ ID NO 68
<211> LENGTH: 127
<212> TYPE: PRT
<213> ORGANISM: Artificial Sequence
<220> FEATURE:
<223> OTHER INFORMATION: Synthetic

<400> SEQUENCE: 68

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Asp Met Ser Trp Val Arg Gln Ala Pro Gly Lys Cys Leu Glu Trp Val
        35                  40                  45

Ser Val Ile Tyr Pro Asp Asp Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Gly Gly Gln Lys Pro Thr Thr Lys Ser Ser Ser Ala Tyr
                100                 105                 110

Gly Met Asp Gly Trp Gly Gln Gly Thr Leu Val Thr Val Ser Ser
            115                 120                 125

<210> SEQ ID NO 69
<211> LENGTH: 110
<212> TYPE: PRT
<213> ORGANISM: Artificial Sequence
<220> FEATURE:
<223> OTHER INFORMATION: Synthetic

<400> SEQUENCE: 69

Gln Ser Val Leu Thr Gln Pro Pro Ser Ala Ser Gly Thr Pro Gly Arg
1               5                   10                  15

Arg Val Thr Ile Ser Cys Ser Gly Ser Ser Asn Ile Gly Asn Asn
            20                  25                  30

Tyr Val Thr Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Cys Gly Thr Lys Leu Thr Val Leu
            100                 105                 110

<210> SEQ ID NO 70
<211> LENGTH: 110
<212> TYPE: PRT
<213> ORGANISM: Artificial Sequence
<220> FEATURE:
<223> OTHER INFORMATION: Synthetic

<400> SEQUENCE: 70

Gln Ser Val Leu Thr Gln Pro Pro Ser Ala Ser Gly Thr Pro Gly Arg
1               5                   10                  15

Arg Val Thr Ile Ser Cys Ser Gly Ser Ser Asn Ile Gly Asn Asn
            20                  25                  30

Tyr Val Thr Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Cys Gly Thr Lys Leu Thr Val Leu
            100                 105                 110

<210> SEQ ID NO 71
<211> LENGTH: 110
<212> TYPE: PRT
<213> ORGANISM: Artificial Sequence
<220> FEATURE:
<223> OTHER INFORMATION: Synthetic

<400> SEQUENCE: 71

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
                20                  25                  30

Tyr Val Thr Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Cys Gly Thr Lys Leu Thr Val Leu
            100                 105                 110

<210> SEQ ID NO 72
<211> LENGTH: 110
<212> TYPE: PRT
<213> ORGANISM: Artificial Sequence
<220> FEATURE:
<223> OTHER INFORMATION: Synthetic

<400> SEQUENCE: 72

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
                20                  25                  30

Tyr Val Thr Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Cys Gly Thr Lys Leu Thr Val Leu
            100                 105                 110

<210> SEQ ID NO 73
<211> LENGTH: 110
<212> TYPE: PRT
<213> ORGANISM: Artificial Sequence
<220> FEATURE:
<223> OTHER INFORMATION: Synthetic

<400> SEQUENCE: 73

Gln Ser Val Leu Thr Gln Pro Pro Ser Ala Ser Gly Thr Pro Gly Arg
1               5                   10                  15

Arg Val Thr Ile Ser Cys Ser Gly Ser Ser Asn Ile Gly Asn Asn
                20                  25                  30

Tyr Val Thr Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Cys Gly Thr Lys Leu Thr Val Leu
            100                 105                 110

```
<210> SEQ ID NO 74
<211> LENGTH: 110
<212> TYPE: PRT
<213> ORGANISM: Artificial Sequence
<220> FEATURE:
<223> OTHER INFORMATION: Synthetic

<400> SEQUENCE: 74

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
                20                  25                  30

Tyr Val Thr Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Cys Gly Thr Lys Leu Thr Val Leu
                100                 105                 110
```

ANTI-CLAUDIN 18.2 AND ANTI-4-1BB BISPECIFIC ANTIBODIES AND USES THEREOF

CROSS REFERENCE TO RELATED APPLICATIONS

This application claims the benefit of PCT Application No. PCT/CN2020/108707, filed Aug. 12, 2020, which claims priority to PCT Application No. PCT/CN2019/100162, filed Aug. 12, 2019, No. PCT/CN2019/104508, filed Sep. 5, 2019, No. PCT/CN2020/071954, filed Jan. 14, 2020, and No. PCT/CN2020/087968, filed Apr. 30, 2020, the content of each which is hereby incorporated by reference in its entirety.

Sequence Listing

The instant application contains a Sequence Listing which has been submitted in ASCII format via EFS-Web and is hereby incorporated by reference in its entirety. Said ASCII copy, created on Apr. 15, 2021, is named 54LW-30073-US_SL.txt and is 87 kilobytes in size.

BACKGROUND

Claudins are a family of proteins that form the important components of the tight cell junctions. Claudin-18 splice variant 2 (CLDN18.2) is a gastric-specific membrane protein. In the healthy tissue, CLDN18.2 is restrictly expressed in the short-lived differentiated cells of gastric mucosa as a component of tight junction with limited accessibility of antibody treatment. However, it was ectopically expressed at significant levels in a variety of primary lesion and metastases of epithelial tumor entities, including gastric, pancreatic, esophageal, and lung adenocarcinoma cells.

4-1BB (CD137, tumor necrosis factor receptor superfamily 9) is a member of TNF-receptor superfamily (TNFRSF) and is a costimulatory molecule which is expressed following the activation of immune cells, both innate and adaptive immune cells. 4-1BB plays an important role in modulating the activity of various immune cells. 4-1BB agonists enhance immune cell proliferation, survival, secretion of cytokines and cytolytic activity CD8 T cells. Many other studies showed that activation of 4-1BB enhances immune response to eliminate tumors in mice. Therefore, it was suggested that 4-1BB is a promising target molecule in cancer immunology.

SUMMARY

Provided are bispecific and multi-specific antibodies that target both claudin 18.2 (CLDN18.2) and 4-1BB. In some embodiments, the antibodies of the present technology include a "conditional agonist" anti-4-1BB portion which, without the anti-CLDN18.2 portion binding to CLDN18.2 proteins expressed on a cell, cannot activate 4-1BB signaling.

4-1BB signaling activation is the expected mechanism for agonist antibodies, such as utomilumab (PF-05082566) and urelumab (BMS-663513). The anti-4-1BB portions of the presently disclosed antibodies, however, do not require such an activity. Actually, it is preferred that the anti-4-1BB portions of the present antibodies are not capable of independently activating 4-1BB in the absence of CLDN18.2 binding. As the experimental examples demonstrated, interestingly, when the anti-CLDN18.2 portion binds to CLDN18.2 proteins on a cell, such CLDN18.2 binding can trigger 4-1BB signaling activation.

Compared to the known anti-4-1BB agonist antibodies which are commonly associated with dose-limiting on-target toxicities, the antibodies of the present disclosure are contemplated to be much safer. In a tissue, such as liver, wherein CLDN18.2 is not expressed, the present antibodies are not expected to trigger cytotoxic immune response as they cannot activate 4-1BB signaling. In a tumor tissue wherein CLDN18.2 is expressed and/or accessible, by contrast, the present antibodies can initiate potent immune response to the tumor cells. Accordingly, unlike those anti-4-1BB antibodies currently being developed clinically which suffer on-target/inherent toxicities, the presently disclosed antibodies can be potent and safe at the same time in treating cancer.

BRIEF DESCRIPTION OF THE DRAWINGS

FIG. 1A-C illustrate three different bispecific formats tested in the present disclosure.

FIG. 2A-D present ELISA results for 4-1BB and CLDN18.2 binding.

FIG. 4A-C show the binding results for CLDN18.2.

FIG. 5A-D show CLDN18.2-dependent 4-1BB signaling activation.

FIG. 6A-E show PBMC response in the presence of CLDN18.2 expressing cells.

FIG. 7A-D show CD8+T response in the presence of CLDN18.2 expressing cells.

FIG. 8A-B show in vivo efficacy of anti-CLDN18.2-4-1BB antibody in syngeneic mouse model and ex vivo analysis of its impact on tumor infiltrating lymphocytes.

FIG. 11A-D show pharmacokinetics and pharmacodynamics relation of D-1A10 in syngeneic mouse model.

DETAILED DESCRIPTION

Definitions

Figure 2A:
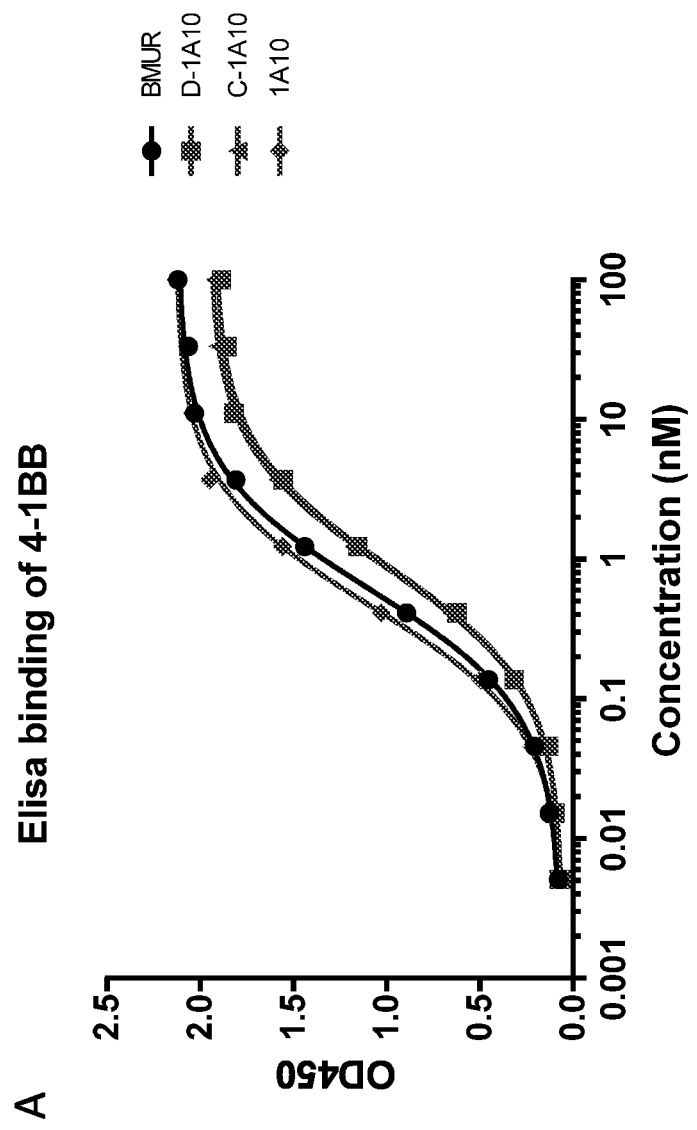

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

The term "isolated" as used herein with respect to cells, nucleic acids, such as DNA or RNA, refers to molecules separated from other DNAs or RNAs, respectively, that are present in the natural source of the macromolecule. The term "isolated" as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to cells or polypeptides which are isolated from other cellular proteins or tissues. Isolated polypeptides is meant to encompass both purified and recombinant polypeptides.

As used herein, the term "recombinant" as it pertains to polypeptides or polynucleotides intends a form of the polypeptide or polynucleotide that does not exist naturally, a non-limiting example of which can be created by combining polynucleotides or polypeptides that would not normally occur together.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+ PDB+GenBank CDS translations+SwissProtein+SPupdate+ PIR. Biologically equivalent polynucleotides are those having the above-noted specified percent homology and encoding a polypeptide having the same or similar biological activity.

As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody" includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody such as F(ab')$_2$, F(ab)$_2$, Fab', Fab, Fv, scFv and the like. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered protein that acts like an antibody by binding to a specific antigen to form a complex.

A "single-chain variable fragment" or "scFv" refers to a fusion protein of the variable regions of the heavy ($V_H$) and light chains ($V_L$) of immunoglobulins. In some aspects, the regions are connected with a short linker peptide of ten to about 25 amino acids. The linker can be rich in glycine for flexibility, as well as serine or threonine for solubility, and can either connect the N-terminus of the $V_H$ with the C-terminus of the $V_L$, or vice versa. This protein retains the specificity of the original immunoglobulin, despite removal of the constant regions and the introduction of the linker. ScFv molecules are known in the art and are described, e.g., in U.S. Pat. No. 5,892,019.

The term antibody encompasses various broad classes of polypeptides that can be distinguished biochemically. Those skilled in the art will appreciate that heavy chains are classified as gamma, mu, alpha, delta, or epsilon ($\gamma$, $\mu$, $\alpha$, $\delta$, $\varepsilon$) with some subclasses among them (e.g., $\gamma1$-$\gamma4$). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgG_5$, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Antibodies, antigen-binding polypeptides, variants, or derivatives thereof of the disclosure include, but are not limited to, polyclonal, monoclonal, multispecific, human, humanized, primatized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VK or VH domain, fragments produced by a Fab expression library, and anti-idiotypic (anti-Id) antibodies (including, e.g., anti-Id antibodies to LIGHT antibodies disclosed herein) Immunoglobulin or antibody molecules of the disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VK) and heavy (VH) chain portions determine antigen recognition and specificity. Conversely, the constant domains of the light chain (CK) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CK domains actually comprise the carboxy-terminus of the heavy and light chain, respectively.

As indicated above, the variable region allows the antibody to selectively recognize and specifically bind epitopes on antigens. That is, the VK domain and VH domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the VH and VK chains (i.e. CDR-H1, CDR-H2, CDR-H3, CDR-L1, CDR-L2 and CDR-L3). In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., *Nature* 363:446-448 (1993).

In naturally occurring antibodies, the six "complementarity determining regions" or "CDRs" present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see "Sequences of Proteins of Immunological Interest," Kabat, E., et al., U.S. Department of Health and Human Services, (1983); and Chothia and Lesk, *J. Mol. Biol.*, 196:901-917 (1987)).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., *J. Mol. Biol.* 196:901-917 (1987), which are incorporated herein by reference in their entireties. The CDR definitions according to Kabat and Chothia include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth in the table below as a comparison. The exact residue numbers which encompass a particular CDR will vary depending on the sequence and size of the CDR. Those skilled in the art can routinely determine which residues comprise a particular CDR given the variable region amino acid sequence of the antibody.

|        | Kabat  | Chothia |
|--------|--------|---------|
| CDR-H1 | 31-35  | 26-32   |
| CDR-H2 | 50-65  | 52-58   |
| CDR-H3 | 95-102 | 95-102  |
| CDR-L1 | 24-34  | 26-32   |
| CDR-L2 | 50-56  | 50-52   |
| CDR-L3 | 89-97  | 91-96   |

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983).

In addition to table above, the Kabat number system describes the CDR regions as follows: CDR-H1 begins at approximately amino acid 31 (i.e., approximately 9 residues after the first cysteine residue), includes approximately 5-7 amino acids, and ends at the next tryptophan residue. CDR-H2 begins at the fifteenth residue after the end of CDR-H1, includes approximately 16-19 amino acids, and ends at the next arginine or lysine residue. CDR-H3 begins at approximately the thirty third amino acid residue after the end of CDR-H2; includes 3-25 amino acids; and ends at the sequence W-G-X-G, where X is any amino acid. CDR-L1 begins at approximately residue 24 (i.e., following a cysteine residue); includes approximately 10-17 residues; and ends at the next tryptophan residue. CDR-L2 begins at approximately the sixteenth residue after the end of CDR-L1 and includes approximately 7 residues. CDR-L3 begins at approximately the thirty third residue after the end of CDR-L2 (i.e., following a cysteine residue); includes approximately 7-11 residues and ends at the sequence F or W-G-X-G, where X is any amino acid.

Antibodies disclosed herein may be from any animal origin including birds and mammals Preferably, the antibodies are human, murine, donkey, rabbit, goat, guinea pig, camel, llama, horse, or chicken antibodies. In another embodiment, the variable region may be condricthoid in origin (e.g., from sharks).

As used herein, the term "heavy chain constant region" includes amino acid sequences derived from an immunoglobulin heavy chain. A polypeptide comprising a heavy chain constant region comprises at least one of: a CH1 domain, a hinge (e.g., upper, middle, and/or lower hinge region) domain, a CH2 domain, a CH3 domain, or a variant or fragment thereof. For example, an antigen-binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the disclosure comprises a polypeptide chain comprising a CH3 domain. Further, an antibody for use in the disclosure may lack at least a portion of a CH2 domain (e.g., all or part of a CH2 domain). As set forth above, it will be understood by one of ordinary skill in the art that the heavy chain constant region may be modified such that they vary in amino acid sequence from the naturally occurring immunoglobulin molecule.

The heavy chain constant region of an antibody disclosed herein may be derived from different immunoglobulin molecules. For example, a heavy chain constant region of a polypeptide may comprise a CH1 domain derived from an $IgG_1$ molecule and a hinge region derived from an $IgG_3$ molecule. In another example, a heavy chain constant region can comprise a hinge region derived, in part, from an $IgG_1$ molecule and, in part, from an $IgG_3$ molecule. In another example, a heavy chain portion can comprise a chimeric hinge derived, in part, from an $IgG_1$ molecule and, in part, from an $IgG_4$ molecule.

As used herein, the term "light chain constant region" includes amino acid sequences derived from antibody light chain. Preferably, the light chain constant region comprises at least one of a constant kappa domain or constant lambda domain.

A "light chain-heavy chain pair" refers to the collection of a light chain and heavy chain that can form a dimer through a disulfide bond between the CL domain of the light chain and the CH1 domain of the heavy chain.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat et al., U.S. Dept. of Health and Human Services, "Sequences of Proteins of Immunological Interest" (1983). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains (Roux et al., *J. Immunol* 161:4083 (1998)).

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

As used herein, the terms "treat" or "treatment" refer to both therapeutic treatment and prophylactic or preventative measures, wherein the object is to prevent or slow down (lessen) an undesired physiological change or disorder, such as the progression of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects, that would benefit from administration of an antibody or composition of the present disclosure used, e.g., for detection, for a diagnostic procedure and/or for treatment.

Anti-Claudin 18.2 Anti-4-IBB Antibodies 4-1BB is an inducible costimulatory receptor expressed on activated T and natural killer (NK) cells. 4-1BB trimer clustering by 4-1BB ligand (41BBL) trimer on T cells triggers a signaling cascade that results in upregulation of antiapoptotic molecules, cytokine secretion, and enhanced effector function. On NK cells, 4-1BB signaling can increase antibody-dependent cell-mediated cytotoxicity. Agonistic monoclonal antibodies targeting 4-1BB have been developed to harness 4-1BB signaling for cancer immunotherapy. Preclinical results in a variety of induced and spontaneous tumor models suggest that targeting 4-1BB with agonist antibodies can lead to tumor clearance and durable antitumor immunity.

Two agonist antibodies, urelumab and utomilumab, are currently undergoing clinical trials. Urelumab has strong efficacy but showed inflammatory liver toxicities. The liver toxicity appears to be on-target, making it difficult to be separated from efficacy. Utomilumab is relatively safer than urelumab, but is also less effective.

The present experimental example tested a couple of anti-4-1BB antibodies which were specifically selected for their incapability to activate 4-1BB signaling independently. In their monospecific forms, they can bind to 4-1BB alone or 4-1BB on the cell surface. Their binding of 4-1BB on the cell surface, however, does not lead to 4-1BB signaling activation (see, e.g., Example 3 and FIG. 5).

Figures 5C, 5D:
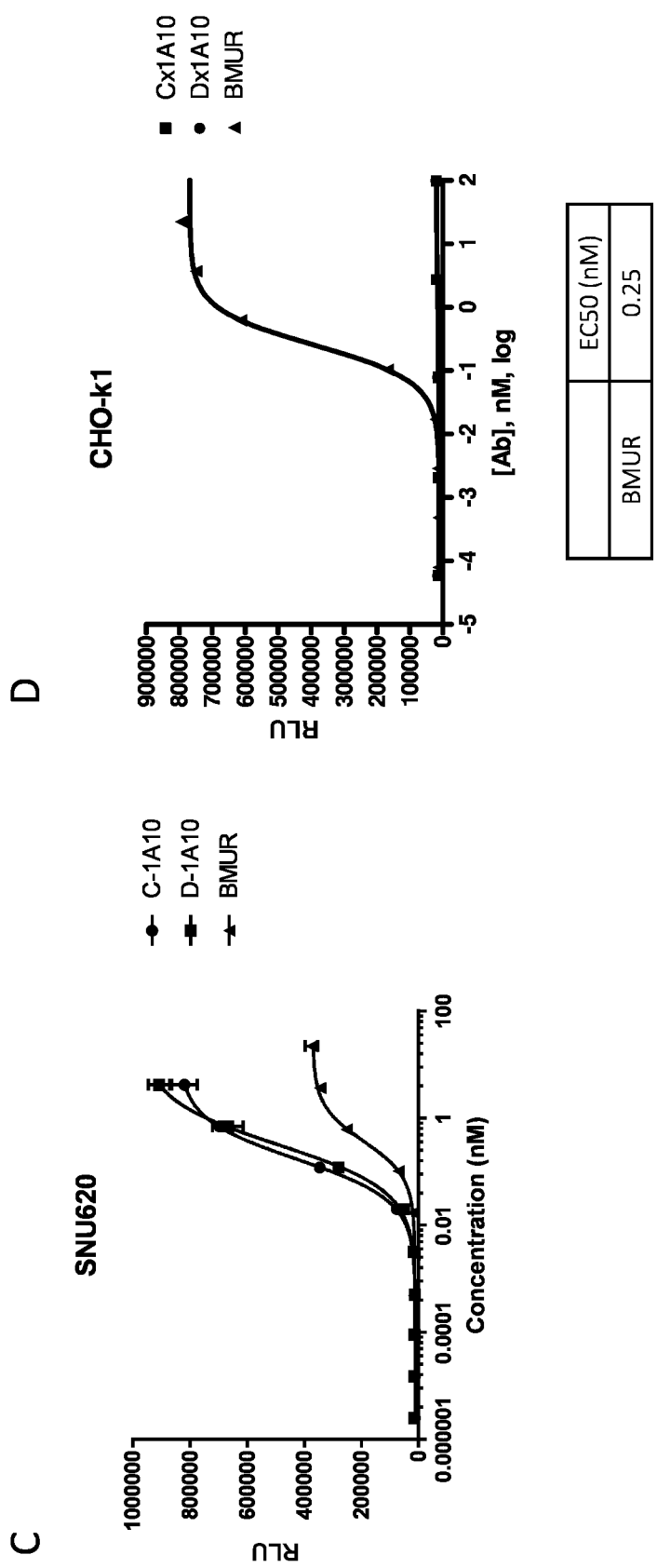

Interestingly, when the binding fragments of one of these conditional agonist 4-1BB antibodies, 1A10, was incorporated into a bispecific antibody that further has an anti-CLDN18.2 portion, the resulting bispecific antibody was able to efficiently activate 4-1BB signaling in a CLDN18.2-binding-dependent manner (see Example 3 and FIG. 5). It is worth noting that these tested bispecific antibodies employed an N297A IgG$_1$ Fc to disable FcγR-medicated 4-1BB agonism. Therefore, the 4-1BB signaling activation can only be attributed to the CLDN18.2 binding.

The on-target toxicity of the anti-4-1BB agonist antibody urelumab is attributed to the antibody's lack of selectivity in 4-1BB agonism. The antibodies of the present technology, however, can be readily recognized for their ability to overcome this limitation. In a tissue, such as liver, where CLDN18.2 is not expressed or accessible, the antibodies would be safe as they cannot activate 4-1BB-mediated cytotoxicity. In a tumor tissue wherein CLDN18.2 is overexpressed or accessible, by contrast, the antibodies undergo CLDN18.2 binding-dependent 4-1BB signaling activation, leading to 4-1BB-mediated immune cell activation, thereby treating the tumor.

In accordance with one embodiment of the present disclosure, therefore, provided is an antibody that includes an anti-claudin 18.2 (CLDN18.2) unit having binding specificity to a CLDN18.2 protein, and an anti-4-1BB unit having binding specificity to a 4-1BB protein. In a preferred embodiment, the anti-4-1BB unit is incapable of activating 4-1BB signaling upon binding to a 4-1BB protein, in the absence of the anti-CLDN18.2 unit binding to a CLDN18.2 protein.

The lack of 4-1BB agonism of the anti-4-1BB portion can be achieved by many different means. It is suggested that 4-1BB clustering on the cell surface is required for its activation. In some embodiments, therefore, the binding of the anti-4-1BB unit to 4-1BB proteins on a cell does not result in clustering of the 4-1BB proteins, in the absence of the anti-CLDN18.2 unit binding to a CLDN18.2 protein.

The 4-1BB protein has four extracellular cysteine-rich pseudo repeats (CRD) domains, CRD1, CRD2, CRD3 and CRD4 (see the amino acid sequence and the CRD regions in the table below). Urelumab binds to the N-terminal CDR1, and activates 4-1BB clustering in a 4-1BB ligand (4-1BBL)-dependent manner. In some embodiments, the anti-4-1BB unit of the presently disclosed antibodies does not bind to CDR1. In some embodiments, the anti-4-1BB unit of the presently disclosed antibodies binds to CDR2. In some embodiments, the anti-4-1BB unit of the presently disclosed antibodies binds to CDR3. In some embodiments, the anti-4-1BB unit of the presently disclosed antibodies binds to CDR4.

| Sequence and CRD Annotation (SEQ ID NO: 39) | |
|---|---|
| Human 4-1BB (NP_0015522) | 1 MGNSCYNIVA TLLLVLNFER TRSLQDPCSNCPAGTFCDNNRNQICSPCPP<br>  Signal peptide                    CRD1<br>51 NSFSSAGGQR TCDICRQCKG VFRTRKECSSTSNAECDCTPGFHCLGAGCS<br>                CRD2                                    CRD3<br>101 MCEQDCKQGQ ELTKKGCKDCCFGTFNDQKR GICRPWTNCSLDGKSVLVNG<br>                                          CRD4<br>151 TKERDVVCGPSPADLSPGASSVTPPAPARE PGHSPQIISFFLALTSTALL<br>201 FLLFFLTLRFSVVKRGRKKLLYIFKQPFMR PVQTTQEEDG CSCRFPEEEE<br>251 GGCEL |

In some instances, 4-1BB clustering may be mediated through the effector function of an anti-4-1BB antibody. In some embodiments, therefore, an antibody of the present disclosure has an Fc fragment that has reduced or no effector function. Such effort functions, in some embodiments, antibody-dependent cell-mediated cytotoxicity (ADCC), complement-dependent cytotoxicity (CDC), or antibody-dependent cellular phagocytosis (ADCP).

The effector function of an antibody can be altered using techniques known in the art. In some embodiments, the Fc fragment of the antibody is mutated, or manufactured, in a manner to reduce or eliminate its binding to FcγR. In some embodiments, the Fc fragment has reduced or no binding to FcγRI (CD64); in some embodiments, the Fc fragment has reduced or no binding to FcγRIIA (CD32); in some embodiments, the Fc fragment has reduced or no binding to FcγRIIB (CD32); in some embodiments, the Fc fragment has reduced or no binding to FcγRIIIA (CD16a); and in some embodiments, the Fc fragment has reduced or no binding to FcγRIIIB (CD16b). In some embodiments, the Fc fragment has reduced or no binding to C1q (first subcomponent of the C1 complex).

In some embodiments, the Fc fragment includes one or more mutations that reduce or eliminate the FcγR or C1q binding of the Fc fragment. Non-limiting examples of such mutations include the L235E mutation in an IgG1 Fc fragment, the L234A and/or L235A mutation in an IgG1 Fc fragment, the P329G or P329A mutation in an IgG1 Fc fragment, the F234A and/or L235A or L235E mutation in an IgG4 Fc fragment, the H268Q, V309L, A330S, and/or P331S mutation in an IgG2 Fc fragment, and the V234A, G237A, P238S, H268A, V309L, A330S, and/or P331S mutation in an IgG2 Fc fragment (EU numbering).

The effector function of an antibody can also be reduced by decreasing or inhibiting glycosylation of the Fc fragment (e.g., an aglycosylated Fc fragment). Such decrease or inhibition can be achieved, in some embodiments, by using a cell line that is incapable to glycosylate the antibody. In some embodiments, the Fc fragment is mutated.

Non-limiting examples of such mutations include a mutation at N297 (such as N297A, N297G, and N297Q) (EU numbering). In some embodiments, the mutation is N297A.

Antibody Formats and Example Sequences

In the experimental examples, three different bispecific antibody formats were tested. Among them, the format of FIG. 1A exhibited higher activity than those of FIG. 1B and FIG. 1C. These data suggest that a suitable format for the antibodies of the present disclosure may employ a Fab fragment for the anti-CLDN18.2 portion. In some embodiments, the format includes a single chain fragment (scFv) for the anti-4-IBB portion. In some embodiments, the anti-4-IBB portion is not located between the Fab and a Fc fragment.

In some embodiments, the anti-CLDN18.2 unit include a Fab fragment, and preferably a pair of the Fab fragment. In some embodiments, the anti-4-IBB unit includes a Fab fragment, preferably a pair of the Fab fragments. In some embodiments, the anti-4-IBB unit includes a scFv, preferably a pair of the scFv fragments.

In some embodiments, the anti-CLDN18.2 unit is located at the N-terminal side of the anti-4-IBB unit. In some embodiments, a Fc fragment is placed between the anti-CLDN18.2 unit and the anti-4-IBB unit.

Example CDR sequence and VH/VL sequences are also provided for the anti-CLDN18.2 unit and the anti-4-IBB unit. In some embodiments, the anti-4-IBB unit comprises a heavy chain variable region (VH) comprising a CDRH1, a CDRH2, and a CDRH3, and a light chain variable region (VL) comprising a CDRL1, a CDRL2 and a CDRL3, wherein: the CDRH1 comprises the amino acid sequence of SEQ ID NO:1, or an amino acid sequence having one or two amino acid substitution from SEQ ID NO:1; the CDRH2 comprises the amino acid sequence of SEQ ID NO:2, or an amino acid sequence having one or two amino acid substitution from SEQ ID NO:2; the CDRH3 comprises the amino acid sequence of SEQ ID NO: 3, 56, 57, 58, or 59, or an amino acid sequence having one or two amino acid substitution from SEQ ID NO: 3, 56, 57, 58, or 59; the CDRL1 comprises the amino acid sequence of SEQ ID NO:4 or 60, or an amino acid sequence having one or two amino acid substitution from SEQ ID NO:4 or 60; the CDRL2 comprises the amino acid sequence of SEQ ID NO:5 or 61, or an amino acid sequence having one or two amino acid substitution from SEQ ID NO:5 or 61; and the CDRL3 comprises the amino acid sequence of SEQ ID NO:6 or 62, or an amino acid sequence having one or two amino acid substitution from SEQ ID NO:6 or 62.

TABLE A

CDR Sequences of an Example Anti-4-1BB Unit

| | Sequence | SEQ ID NO: |
|---|---|---|
| CDRH1 | SYDMS | 1 |
| CDRH2 | WISYSGGSIYYADSVKG | 2 |
| CDRH3 | DAQRNSMREFDY, | 3 |
| | DGQRNSMREFDY, | 56 |
| | DAQRQSMREFDY, | 57 |
| | DGQRQSMREFDY, or | 58 |
| | DAQRNAMREFDY | 59 |
| CDRL1 | SGSSSNIGNNYVT | 4 |
| CDRL2 | ADSHRPS | 5 |
| CDRL3 | ATWDYSLSGYV | 6 |

TABLE A-continued

CDR Sequences of an Example Anti-4-1BB Unit

| | Sequence | SEQ ID NO: |
|---|---|---|
| CDRH1 | GYDMS | 60 |
| CDRH2 | VIYPDDGNTYYADSVKG | 61 |
| CDRH3 | HGGQKPTTKSSSAYGMDG | 62 |
| CDRL1 | SGSSSNIGNNYVT | 4 |
| CDRL2 | ADSHRPS | 5 |
| CDRL3 | ATWDYSLSGYV | 6 |

In some embodiments, the CDRH1 comprises the amino acid sequence of SEQ ID NO:1 or 60; the CDRH2 comprises the amino acid sequence of SEQ ID NO:2 or 61; the CDRH3 comprises the amino acid sequence of SEQ ID NO: 3, 56, 57, 58, 59, or 62; the CDRL1 comprises the amino acid sequence of SEQ ID NO:4; the CDRL2 comprises the amino acid sequence of SEQ ID NO:5; and the CDRL3 comprises the amino acid sequence of SEQ ID NO:6.

In some embodiments, the anti-4-1BB unit comprises a heavy chain variable region (VH) comprising an amino acid sequence selected from the group consisting of SEQ ID NO:24, 46-51 and 63-69 and a light chain variable region (VL) comprising an amino acid sequence selected from the group consisting of SEQ ID NO:25, 52-53 and 70-74.

TABLE B

VH/VL Sequences of an Example Anti-4-1BB Unit

| 1A10 VH | EVQLLESGGGLVQPGGSLRLSCAASGFTFSSYDMSWVRQAP GKCLEWVSWISYSGGSIYYADSVKGRFTISRDNSKNTLYLQ MNSLRAEDTAVYYCARDAQRNSMREFDYWGQGTLVTVSS (SEQ ID NO: 24) |
|---|---|
| 1A10 VL | QSVLTQPPSASGTPGQRVTISCSGSSSNIGNNYVTWYQQLP GTAPKLLIYADSHRPSGVPDRFSGSKSGTSASLAISGLRSE DEADYYCATWDYSLSGYVFGCGTKLTVL (SEQ ID NO: 25) |

In some embodiments, the anti-CLDN18.2 unit comprises a heavy chain variable region (VH) comprising a CDRH1, a CDRH2, and a CDRH3, and a light chain variable region (VL) comprising a CDRL1, a CDRL2 and a CDRL3, wherein (a) the CDRH1 comprises the amino acid sequence of SEQ ID NO:7; the CDRH2 comprises the amino acid sequence of SEQ ID NO:8; the CDRH3 comprises the amino acid sequence of SEQ ID NO:9; the CDRL1 comprises the amino acid sequence of SEQ ID NO:10; the CDRL2 comprises the amino acid sequence of SEQ ID NO:11; and the CDRL3 comprises the amino acid sequence of SEQ ID NO:12.

In some embodiments, the anti-CLDN18.2 unit comprises a heavy chain variable region (VH) comprising a CDRH1, a CDRH2, and a CDRH3, and a light chain variable region (VL) comprising a CDRL1, a CDRL2 and a CDRL3, wherein (b) the CDRH1 comprises the amino acid sequence of SEQ ID NO:13; the CDRH2 comprises the amino acid sequence of SEQ ID NO:14; the CDRH3 comprises the amino acid sequence of SEQ ID NO:15; the CDRL1 comprises the amino acid sequence of SEQ ID NO:16; the CDRL2 comprises the amino acid sequence of SEQ ID NO:17; and the CDRL3 comprises the amino acid sequence of SEQ ID NO:18.

In some embodiments, the anti-CLDN18.2 unit comprises a heavy chain variable region (VH) comprising a CDRH1, a CDRH2, and a CDRH3, and a light chain variable region (VL) comprising a CDRL1, a CDRL2 and a CDRL3, wherein (c) the CDRH1 comprises the amino acid sequence of SEQ ID NO:19; the CDRH2 comprises the amino acid sequence of SEQ ID NO:20; the CDRH3 comprises the amino acid sequence of SEQ ID NO:21; the CDRL1 comprises the amino acid sequence of SEQ ID NO:22; the CDRL2 comprises the amino acid sequence of SEQ ID NO:11; and the CDRL3 comprises the amino acid sequence of SEQ ID NO:23.

TABLE C

CDR Sequences of Example Anti-CLDN18.2 Units

| | | Sequence | SEQ ID NO: |
|---|---|---|---|
| 4F11E2 | CDRH1 | TFGMH | 7 |
| | CDRH2 | YITSGESPIYFTDTVKG | 8 |
| | CDRH3 | SSYYGNSMDY | 9 |
| | CDRL1 | RSSQSLLNAGNRKNYLT | 10 |
| | CDRL2 | WASTRES | 11 |
| | CDRL3 | QNAYSYPFT | 12 |
| 72C1B6A3 | CDRH1 | TYPIE | 13 |
| | CDRH2 | NFHPYNDDTKYNEKFKG | 14 |
| | CDRH3 | RAYGYPYAMDY | 15 |
| | CDRL1 | KSSQSLLNAGNQKNYLT | 16 |
| | CDRL2 | RASSRES | 17 |
| | CDRL3 | QNDYIYPYT | 18 |
| 120B782 | CDRH1 | GYIIQ | 19 |
| | CDRH2 | FINPYNDDTKYNEQFKG | 20 |
| | CDRH3 | AYFGNAFAY | 21 |
| | CDRL1 | KSSQSLLNAGNQKNYLT | 22 |
| | CDRL2 | WASTRES | 11 |
| | CDRL3 | QNAYYFPFT | 23 |

In some embodiments, the VH of the anti-CLDN18.2 unit comprises an amino acid sequence selected from the group consisting of SEQ ID NO:26, 28 and 30, and the $V_H$ of the anti-CLDN18.2 unit comprises an amino acid sequence selected from the group consisting of SEQ ID NO:27, 29 and 31.

In some embodiments, provided is a bispecific antibody adopting a format like illustrated in FIG. 1A. In some embodiments, provided is an antibody comprising two first polypeptides and two second polypeptides, wherein each first polypeptide comprises, from N- to C-terminus, a heavy chain variable region (VH), a CH1, a CH2, a CH3, and a single chain fragment (scFv) having specificity to a 4-1BB protein; wherein each second polypeptide comprises a light chain variable region (VL) and a CL; wherein each VH is paired with one of the VL and have specificity to a claudin 18.2 (CLDN18.2) protein; and wherein the scFv is incapable of activating 4-1BB signaling upon binding to a 4-1BB protein, in the absence of the VH/VL pairs binding to a CLDN18.2 protein.

The VH/VL pair here constitutes an anti-CLDN18.2 unit and the scFv constitutes an anti-4-1BB unit. The CH2-CH3/CH2-CH3 pair constitutes an Fc fragment. The various embodiments above relating to the anti-CLDN18.2 unit, the anti-4-1BB unit, and the Fc fragments may be applicable here as well.

The following table provides non-limiting examples of the first polypeptide (heavy component) and the second polypeptide (light component). In some embodiments, each of the first polypeptides comprises the amino acid sequence of SEQ ID NO:40 and each of the second polypeptides comprises the amino acid sequence of SEQ ID NO:41.

In some embodiments, each of the first polypeptides comprises the amino acid sequence of SEQ ID NO:42 and each of the second polypeptides comprises the amino acid sequence of SEQ ID NO:43.

In some embodiments, each of the first polypeptides comprises the amino acid sequence of SEQ ID NO:44 and each of the second polypeptides comprises the amino acid sequence of SEQ ID NO:45.

TABLE D

Peptide Chains of Example Bispecific Antibodies

C-1A10

| | | | |
|---|---|---|---|
| Heavy component (SEQ ID NO: 40) | Heavy chain of 4F11E2 | | EVQLVESGGGLVQPGGSLRLSCAASGFTFSTFGMHWVRQAPGKGLEWVS YITSGESPIYFTDTVKGRFTISRDNAKNSLYLQMNSLRAEDTAVYYCAR SSYYGNSMDYWGQGTLVTVSS (SEQ ID NO: 26) ASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKV EPKSCDKTHTCPPCPAPELLGGPSVFLFPPKPKDTLMISRTPEVTCVVV DVSHEDPEVKFNWYVDGVEVHNAKTKPREEQYASTYRVVSVLTVLHQDW LNGKEYKCKVSNKALPAPIEKTISKAKGQPREPQVYTLPPSREEMTKNQ VSLTCLVKGFYPSDIAVEWESNGQPENNYKTTPPVLDSDGSFFLYSKLT VDKSRWQQGNVFSCSVMHEALHNHYTQKSLSLSPGK (SEQ ID NO: 32) |
| | | Linker | GGGGSGGGGSGGGGS (SEQ ID NO: 34) |
| | scFv of 1A10 | VL | QSVLTQPPSASGTPGQRVTISCSGSSSNIGNNYVTWYQQLPGTAPKLLI YADSHRPSGVPDRFSGSKSGTSASLAISGLRSEDEADYYCATWDYSLSG YVFGCGTKLTVL (SEQ ID NO: 25) |
| | | Linker | GGGGSGGGGSGGGGSGGGGS (SEQ ID NO: 35) |
| | | VH | EVQLLESGGGLVQPGGSLRLSCAASGFTFSSYDMSWVRQAPGKCLEWVS WISYSGGSIYYADSVKGRFTISRDNSKNTLYLQMNSLRAEDTAVYYCAR DAQRNSMREFDYWGQGTLVTVSS (SEQ ID NO: 24) |
| Light component (SEQ ID NO: 41) | Light chain of 4E11E2 | | DIVMTQSPDSLAVSLGERATINCRSSQSLLNAGNRKNYLTWYQQKPGQP PKLLIYWASTRESGVPDRFSGSGSGTDFTLTISSLQAEDVAVYYCQNAY SYPFTFGGGTKLEIK (SEQ ID NO: 27) RTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPV TKSFNRGEC (SEQ ID NO: 33) |

TABLE D-continued

Peptide Chains of Example Bispecific Antibodies

D-1A10

| | | | |
|---|---|---|---|
| Heavy component (SEQ ID NO: 42) | Heavy chain of 72C1B6A3 | | QVQLVQSGAEVKKPGASVKVSCKASGYTFTTYPIEWVRQAPGQRLEWMGNFHPYNDDTKYNEKFKGRVTITRDTSASTAYMELSSLRSEDTAVYYCARRAYGYPYAMDYWGQGTLVTVSS (SEQ ID NO: 28) ASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKV EPKSCDKTHTCPPCPAPELLGGPSVFLFPPKPKDTLMISRTPEVTCVVV DVSHEDPEVKFNWYVDGVEVHNAKTKPREEQYASTYRVVSVLTVLHQDW LNGKEYKCKVSNKALPAPIEKTISKAKGQPREPQVYTLPPSREEMTKNQ VSLTCLVKGFYPSDIAVEWESNGQPENNYKTTPPVLDSDGSFFLYSKLT VDKSRWQQGNVFSCSVMHEALHNHYTQKSLSLSPGK (SEQ ID NO: 32) |
| | Linker | | GGGGSGGGGSGGGGS (SEQ ID NO: 34) |
| | scFv of 1A10 | VL | QSVLTQPPSASGTPGQRVTISCSGSSSNIGNNYVTWYQQLPGTAPKLLI YADSHRPSGVPDRFSGSKSGTSASLAISGLRSEDEADYYCATWDYSLSG YVFGCGTKLTVL (SEQ ID NO: 25) |
| | | Linker | GGGGSGGGGSGGGGSGGGGS (SEQ ID NO: 35) |
| | | VH | EVQLLESGGGLVQPGGSLRLSCAASGFTFSSYDMSWVRQAPGKCLEWVSWISYSGGSIYYADSVKGRFTISRDNSKNTLYLQMNSLRAEDTAVYYCARDAQRNSMREFDYWGQGTLVTVSS (SEQ ID NO: 24) |
| Light component (SEQ ID NO: 43) | Light chain of 72C1B6A3 | | DIVMTQSPDSLAVSLGERATINCKSSQSLLNAGNQKNYLTWYQQKPGQP PKLLIYRASSRESGVPDRFSGSGSGTDFTLTISSLQAEDVAVYYCQNDY IYPYTFGGGTKLEIK (SEQ ID NO: 29) RTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPV TKSFNRGEC (SEQ ID NO: 33) |

E-1A10

| | | | |
|---|---|---|---|
| Heavy component (SEQ ID NO: 44) | Heavy chain of 120B7B2 | | QVQLVQSGAEVKKPGASVKVSCKASGYTFTGYIIQWVRQAPGQRLEWMGFINPYNDDTKYNEQFKGRVTITRDTSASTAYMELSSLRSEDTAVYYCARAYFGNAFAYWGQGTLVTVSS (SEQ ID NO: 30) ASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKV EPKSCDKTHTCPPCPAPELLGGPSVFLFPPKPKDTLMISRTPEVTCVVV DVSHEDPEVKFNWYVDGVEVHNAKTKPREEQYASTYRVVSVLTVLHQDW LNGKEYKCKVSNKALPAPIEKTISKAKGQPREPQVYTLPPSREEMTKNQ VSLTCLVKGFYPSDIAVEWESNGQPENNYKTTPPVLDSDGSFFLYSKLT VDKSRWQQGNVFSCSVMHEALHNHYTQKSLSLSPGK (SEQ ID NO: 32) |
| | Linker | | GGGGSGGGGSGGGGS (SEQ ID NO: 34) |
| | scFv of 1A10 | VL | QSVLTQPPSASGTPGQRVTISCSGSSSNIGNNYVTWYQQLPGTAPKLLI YADSHRPSGVPDRFSGSKSGTSASLAISGLRSEDEADYYCATWDYSLSG YVFGCGTKLTVL (SEQ ID NO: 25) |
| | | Linker | GGGGSGGGGSGGGGSGGGGS (SEQ ID NO: 35) |
| | | VH | EVQLLESGGGLVQPGGSLRLSCAASGFTFSSYDMSWVRQAPGKCLEWVSWISYSGGSIYYADSVKGRFTISRDNSKNTLYLQMNSLRAEDTAVYYCARDAQRNSMREFDYWGQGTLVTVSS (SEQ ID NO: 24) |
| Light component (SEQ ID NO: 45) | Light chain of 120B7B2 | | DIVMTQSPDSLAVSLGERATINCKSSQSLLNAGNQKNYLTWYQQKPGQP PKLLIYWASTRESGVPDRFSGSGSGTDFTLTISSLQAEDVAVYYCQNAY YFPFTFGGGTKLEIK (SEQ ID NO: 31) RTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPV TKSFNRGEC (SEQ ID NO: 33) |

TABLE D2

Integrated Sequences of Example Bispecific Antibodies

C-1A10

| | |
|---|---|
| Heavy component (SEQ ID NO: 40) | EVQLVESGGGLVQPGGSLRLSCAASGFTESTFGMHWVRQAPGKGLEWVSYITSGESPIYFTD TVKGRFTISRDNAKNSLYLQMNSLRAEDTAVYYCARSSYYGNSMDYWGQGTLVTVSSASTKG PSVFPLAPSSKSTSGGTAALGCLVKDYFPEPVTVSWNSGALTSGVHTFPAVLQSSGLYSLSS VVTVPSSSLGTQTYICNVNHKPSNTKVDKKVEPKSCDKTHTCPPCPAPELLGGPSVFLFPPK PKDTLMISRTPEVTCVVVDVSHEDPEVKFNWYVDGVEVHNAKTKPREEQYASTYRVVSVLTV LHQDWLNGKEYKCKVSNKALPAPIEKTISKAKGQPREPQVYTLPPSREEMTKNQVSLTCLVK GFYPSDIAVEWESNGQPENNYKTTPPVLDSDGSFELYSKLTVDKSRWQQGNVFSCSVMHEAL HNHYTQKSLSLSPGKGGGGSGGGGSGGGGSQSVLTQPPSASGTPGQRVTISCSGSSSNIGNN YVTWYQQLPGTAPKLLIYADSHRPSGVPDRFSGSKSGTSASLAISGLRSEDEADYYCATWDY SLSGYVFGCGTKLTVLGGGGSGGGGSGGGGSGGGGSEVQLLESGGGLVQPGGSLRLSCAASG FTFSSYDMSWVRQAPGKCLEWVSWISYSGGSIYYADSVKGRFTISRDNSKNTLYLQMNSLRA EDTAVYYCARDAQRNSMREFDYWGQGTLVTVSS |

TABLE D2-continued

Integrated Sequences of Example Bispecific Antibodies

| | |
|---|---|
| Light component (SEQ ID NO: 41) | DIVMTQSPDSLAVSLGERATINCRSSQSLLNAGNRKNYLTWYQQKPGQPPKLLIYWASTRESGVPDRFSGSGSGTDFTLTISSLQAEDVAVYYCQNAYSYPFTFGGGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

D-1A10

| | |
|---|---|
| Heavy component (SEQ ID NO: 42) | QVQLVQSGAEVKKPGASVKVSCKASGYTFTTYPIEWVRQAPGQRLEWMGNFHPYNDDTKYNEKFKGRVTITRDTSASTAYMELSSLRSEDTAVYYCARRAYGYPYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGKGGGSGGGGSGGGGSQSVLTQPPSASGTPGQRVTISCSGSSSNIGNNYVTWYQQLPGTAPKLLIYADSHRPSGVPDRFSGSKSGTSASLAISGLRSEDEADYYCATWDYSLSGYVFGCGTKLTVLGGGGSGGGGSGGGGSGGGGSEVQLLESGGGLVQPGGSLRLSCAASSGTFSSYDMSWVRQAPGKCLEWVSWISYSGGSIYYADSVKGRFTISRDNSKNTLYLQMNSLRAEDTAVYYCARDAQRNSMREFDYWGQGTLVTVSS |
| Light component (SEQ ID NO: 43) | DIVMTQSPDSLAVSLGERATINCKSSQSLLNAGNQKNYLTWYQQKPGQPPKLLIYRASSRESGVPDRFSGSGSGTDFTLTISSLQAEDVAVYYCQNDYIYPYTFGGGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

E-1A10

| | |
|---|---|
| Heavy component (SEQ ID NO: 44) | QVQLVQSGAEVKKPGASVKVSCKASGYTFTGYIIQWVRQAPGQRLEWMGFINPYNDDTKYNEQFKGRVTITRDTSASTAYMELSSLRSEDTAVYYCARAYFGNAFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGKGGGGSGGGGSGGGGSQSVLTQPPSASGTPGQRVTISCSGSSSNIGNNYVTWYQQLPGTAPKLLIYADSHRPSGVPDRFSGSKSGTSASLAISGLRSEDEADYYCATWDYSLSGYVFGCGTKLTVLGGGGSGGGGSGGGGSGGGGSEVQLLESGGGLVQPGGSLRLSCAASGFTFSSYDMSWVRQAPGKCLEWVSWISYSGGSIYYADSVKGRFTISRDNSKNTLYLQMNSLRAEDTAVYYCARDAQRNSMREFDYWGQGTLVTVSS |
| Light component (SEQ ID NO: 45) | DIVMTQSPDSLAVSLGERATINCKSSQSLLNAGNQKNYLTWYQQKPGQPPKLLIYWASTRESGVPDRFSGSGSGTDFTLTISSLQAEDVAVYYCQNAYYFPFTFGGGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

It will also be understood by one of ordinary skill in the art that antibodies as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 80%, 85%, 90%, 95%, 98%, or 99% identical to the starting sequence.

In certain embodiments, the antibody comprises an amino acid sequence or one or more moieties not normally associated with an antibody. Exemplary modifications are described in more detail below. For example, an antibody of the disclosure may comprise a flexible linker sequence, or may be modified to add a functional moiety (e.g., PEG, a drug, a toxin, or a label).

Antibodies, variants, or derivatives thereof of the disclosure include derivatives that are modified, i.e., by the covalent attachment of any type of molecule to the antibody such that covalent attachment does not prevent the antibody from binding to the epitope. For example, but not by way of limitation, the antibodies can be modified, e.g., by glycosylation, acetylation, pegylation, phosphorylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the antibodies may contain one or more non-classical amino acids.

In some embodiments, the antibodies may be conjugated to therapeutic agents, prodrugs, peptides, proteins, enzymes, viruses, lipids, biological response modifiers, pharmaceutical agents, or PEG.

The antibodies may be conjugated or fused to a therapeutic agent, which may include detectable labels such as radioactive labels, an immunomodulator, a hormone, an enzyme, an oligonucleotide, a photoactive therapeutic or diagnostic agent, a cytotoxic agent, which may be a drug or a toxin, an ultrasound enhancing agent, a non-radioactive label, a combination thereof and other such agents known in the art.

The antibodies can be detectably labeled by coupling it to a chemiluminescent compound. The presence of the chemiluminescent-tagged antigen-binding polypeptide is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

The antibodies can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA). Techniques for conjugating various moieties to an antibody are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in Controlled Drug Delivery (2nd Ed.), Robinson et al., (eds.), Marcel Dekker, Inc., pp. 623-53 (1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), Academic Press pp. 303-16 (1985), and Thorpe et al., "The Preparation And Cytotoxic Properties Of Antibody-Toxin Conjugates", *Immunol. Rev.* (52:119-58 (1982)).

Polynucleotides Encoding the Antibodies and Methods of Preparing the Antibodies

The present disclosure also provides isolated polynucleotides or nucleic acid molecules encoding the antibodies, variants or derivatives thereof of the disclosure. The polynucleotides of the present disclosure may encode the entire heavy and light chain variable regions of the antigen-binding polypeptides, variants or derivatives thereof on the same polynucleotide molecule or on separate polynucleotide molecules. Additionally, the polynucleotides of the present disclosure may encode portions of the heavy and light chain variable regions of the antigen-binding polypeptides, variants or derivatives thereof on the same polynucleotide molecule or on separate polynucleotide molecules.

Methods of making antibodies are well known in the art and described herein. In certain embodiments, both the variable and constant regions of the antigen-binding polypeptides of the present disclosure are fully human Fully human antibodies can be made using techniques described in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140 which are incorporated by reference in their entireties.

Treatment Methods

As described herein, the antibodies, variants or derivatives of the present disclosure may be used in certain treatment and diagnostic methods.

The present disclosure is further directed to antibody-based therapies which involve administering the antibodies of the disclosure to a patient such as an animal, a mammal, and a human for treating one or more of the disorders or conditions described herein. Therapeutic compounds of the disclosure include, but are not limited to, antibodies of the disclosure (including variants and derivatives thereof as described herein) and nucleic acids or polynucleotides encoding antibodies of the disclosure (including variants and derivatives thereof as described herein).

In some embodiments, provided are methods for treating a cancer in a patient in need thereof. The method, in one embodiment, entails administering to the patient an effective amount of an antibody of the present disclosure. In some embodiments, at least one of the cancer cells (e.g., stromal cells) in the patient over-express claudin 18.2.

Cellular therapies, such as chimeric antigen receptor (CAR) T-cell therapies, are also provided in the present disclosure. A suitable cell can be used, that is put in contact with an antibody of the present disclosure (or alternatively engineered to express an antibody of the present disclosure). Upon such contact or engineering, the cell can then be introduced to a cancer patient in need of a treatment. The cancer patient may have a cancer of any of the types as disclosed herein. The cell (e.g., T cell) can be, for instance, a tumor-infiltrating T lymphocyte, a CD4+ T cell, a CD8+ T cell, or the combination thereof, without limitation.

In some embodiments, the cell was isolated from the cancer patient him- or her-self. In some embodiments, the cell was provided by a donor or from a cell bank. When the cell is isolated from the cancer patient, undesired immune reactions can be minimized.

Non-limiting examples of cancers include bladder cancer, breast cancer, colorectal cancer, endometrial cancer, esophageal cancer, head and neck cancer, kidney cancer, leukemia, liver cancer, lung cancer, lymphoma, melanoma, pancreatic cancer, prostate cancer, and thyroid cancer. In some embodiments, the cancer is one or more of gastric, pancreatic, esophageal, ovarian, and lung cancers.

Additional diseases or conditions associated with increased cell survival, that may be treated, prevented, diagnosed and/or prognosed with the antibodies or variants, or derivatives thereof of the disclosure include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

A specific dosage and treatment regimen for any particular patient will depend upon a variety of factors, including the particular antibodies, variant or derivative thereof used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

Methods of administration of the antibodies, variants or include but are not limited to intradermal, intramuscular, intraperitoneal, intravenous, subcutaneous, intranasal, epidural, and oral routes. The antigen-binding polypeptides or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Thus, pharmaceutical compositions containing the antigen-binding polypeptides of the disclosure may be administered orally, rectally, parenterally, intracistemally, intravaginally, intraperitoneally, topically (as by powders, ointments, drops or transdermal patch), bucally, or as an oral or nasal spray.

The term "parenteral" as used herein refers to modes of administration which include intravenous, intramuscular, intraperitoneal, intrasternal, subcutaneous and intra-articular injection and infusion.

Administration can be systemic or local. In addition, it may be desirable to introduce the antibodies of the disclosure into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

It may be desirable to administer the antigen-binding polypeptides or compositions of the disclosure locally to the area in need of treatment; this may be achieved by, for example, and not by way of limitation, local infusion during surgery, topical application, e.g., in conjunction, with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the disclosure, care must be taken to use materials to which the protein does not absorb.

The amount of the antibodies of the disclosure which will be effective in the treatment, inhibition and prevention of an inflammatory, immune or malignant disease, disorder or condition can be determined by standard clinical techniques. In addition, in vitro assays may optionally be employed to help identify optimal dosage ranges. The precise dose to be employed in the formulation will also depend on the route of administration, and the seriousness of the disease, disorder or condition, and should be decided according to the judgment of the practitioner and each patient's circumstances. Effective doses may be extrapolated from dose-response curves derived from in vitro or animal model test systems.

As a general proposition, the dosage administered to a patient of the antigen-binding polypeptides of the present disclosure is typically 0.1 mg/kg to 100 mg/kg of the patient's body weight, between 0.1 mg/kg and 20 mg/kg of the patient's body weight, or 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the disclosure may be reduced by enhancing uptake and tissue penetration (e.g., into the brain) of the antibodies by modifications such as, for example, lipidation.

In an additional embodiment, the compositions of the disclosure are administered in combination with cytokines. Cytokines that may be administered with the compositions of the disclosure include, but are not limited to, IL-2, IL-3, IL-4, IL-5, IL-6, IL-7, IL-10, IL-12, IL-13, IL-15, anti-CD40, CD40L, and TNF-α.

In additional embodiments, the compositions of the disclosure are administered in combination with other therapeutic or prophylactic regimens, such as, for example, radiation therapy.

Compositions

The present disclosure also provides pharmaceutical compositions. Such compositions comprise an effective amount of an antibody, and an acceptable carrier. In some embodiments, the composition further includes a second anticancer agent (e.g., an immune checkpoint inhibitor).

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. Further, a "pharmaceutically acceptable carrier" will generally be a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin, incorporated herein by reference. Such compositions will contain a therapeutically effective amount of the antigen-binding polypeptide, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

EXAMPLES

Example 1: Generation of Anti-CLDN18.2/4-1BB Bispecific Antibodies

Three previously identified anti-CLDN18.2 antibodies, 4F11E2, 72C1B6A3 and 120B7B2, and an anti-4-1BB antibody, 1A10 (sequences are shown in the tables below), were selected to generate anti-CLDN18.2-4-1BB bispecific antibodies in a full-length IgG X scFv form (structure illustrated in FIG. 1A). The anti-Claudin 18.2 portion was placed in full IgG part, while the anti-4-1BB was a scFv placed at the C-terminal side of the Fc fragment. The bispecific antibodies included an IgG1 backbone with a N297A mutation to disable Fcγ function.

TABLE 1

Antibody Sequences

| | | | |
|---|---|---|---|
| | | C-1A10 | |
| Heavy component | Heavy chain of 4F11E2 | | EVQLVESGGGLVQPGGSLRLSCAASGFTFSTFGMHWVRQAPGKGLEWVSYITSGESPIYFTDTVKGRFTISRDNAKNSLYLQMNSLRAEDTAVYYCARSSYYGNSMDYWGQGTLVTVSS (SEQ ID NO: 26) ASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKV EPKSCDKTHTCPPCPAPELLGGPSVFLFPPKPKDTLMISRTPEVTCVVV DVSHEDPEVKFNWYVDGVEVHNAKTKPREEQYASTYRVVSVLTVLHQDW LNGKEYKCKVSNKALPAPIEKTISKAGQPREPQVYTLPPSREEMTKNQ VSLTCLVKGFYPSDIAVEWESNGQPENNYKTTPPVLDSDGSFFLYSKLT VDKSRWQQGNVFSCSVMHEALHNHYTQKSLSLSPGK (SEQ ID NO: 32) |
| | Linker | | GGGGSGGGGSGGGGS (SEQ ID NO: 34) |
| | scFv of 1A10 | VL | QSVLTQPPSASGTPGQRVTISCSGSSSNIGNNYVTWYQQLPGTAPKLLIYADSHRPSGVPDRFSGSKSGTSASLAISGLRSEDEADYYCATWDYSLSG YVFGCGTKLTVL (SEQ ID NO: 25) |
| | | Linker | GGGGSGGGGSGGGGSGGGGS (SEQ ID NO: 35) |
| | | VH | EVQLLESGGGLVQPGGSLRLSCAASGFTFSSYDMSWVRQAPGKCLEWVSWISYSGGSIYYADSVKGRFTISRDNSKNTLYLQMNSLRAEDTAVYYCARDAQRNSMREFDYWGQGTLVTVSS (SEQ ID NO: 24) |
| Light component | Light chain of 4F11E2 | | DIVMTQSPDSLAVSLGERATINCRSSQSLLNAGNRKNYLTWYQQKPGQP PKLLIYWASTRESGVPDRFSGSGSGTDFTLTISSLQAEDVAVYYCQNAY SYPFTFGGGTKLEIK (SEQ ID NO: 27) RTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPV TKSFNRGEC (SEQ ID NO: 33) |
| | | D-1A10 | |
| Heavy component | Heavy chain of 72C1B6A3 | | QVQLVQSGAEVKKPGASVKVSCKASGYTFTTYPIEWVRQAPGQRLEWMGNFHPYNDDTKYNEKFKGRVTITRDTSASTAYMELSSLRSEDTAVYYCARRAYGYPYAMDYWGQGTLVTVSS (SEQ ID NO: 28) ASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKV EPKSCDKTHTCPPCPAPELLGGPSVFLFPPKPKDTLMISRTPEVTCVVV DVSHEDPEVKFNWYVDGVEVHNAKTKPREEQYASTYRVVSVLTVLHQDW LNGKEYKCKVSNKALPAPIEKTISKAGQPREPQVYTLPPSREEMTKNQ VSLTCLVKGFYPSDIAVEWESNGQPENNYKTTPPVLDSDGSFFLYSKLT VDKSRWQQGNVFSCSVMHEALHNHYTQKSLSLSPGK (SEQ ID NO: 32) |
| | Linker | | GGGGSGGGGSGGGGS (SEQ ID NO: 34) |
| | scFv of 1A10 | VL | QSVLTQPPSASGTPGQRVTISCSGSSSNIGNNYVTWYQQLPGTAPKLLIYADSHRPSGVPDRFSGSKSGTSASLAISGLRSEDEADYYCATWDYSLSG YVFGCGTKLTVL (SEQ ID NO: 25) |
| | | Linker | GGGGSGGGGSGGGGSGGGGS (SEQ ID NO: 35) |
| | | VH | EVQLLESGGGLVQPGGSLRLSCAASGFTFSSYDMSWVRQAPGKCLEWVSWISYSGGSIYYADSVKGRFTISRDNSKNTLYLQMNSLRAEDTAVYYCARDAQRNSMREFDYWGQGTLVTVSS (SEQ ID NO: 24) |

TABLE 1-continued

Antibody Sequences

| | | |
|---|---|---|
| Light component | Light chain of 72C166A3 | DIVMTQSPDSLAVSLGERATINCKSSQSLLNAGNQKNYLTWYQQKPGQP PKLLIYRASSRESGVPDRFSGSGSGTDFTLTISSLQAEDVAVYYCQNDY IYPYTFGGGTKLEIK (SEQ ID NO: 29) RTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPV TKSFNRGEC (SEQ ID NO: 33) |

E-1A10

| | | | |
|---|---|---|---|
| Heavy component | Heavy chain of 120B762 | | QVQLVQSGAEVKKPGASVKVSCKASGYTFTGYIIQWVRQAPGQRLEWMG FINPYNDDTKYNEQFKGRVTITRDTSASTAYMELSSLRSEDTAVYYCAR AYFGNAFAYWGQGTLVTVSS (SEQ ID NO: 30) ASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKV EPKSCDKTHTCPPCPAPELLGGPSVFLFPPKPKDTLMISRTPEVTCVVV DVSHEDPEVKFNWYVDGVEVHNAKTKPREEQYASTYRVVSVLTVLHQDW LNGKEYKCKVSNKALPAPIEKTISKAKGQPREPQVYTLPPSREEMTKNQ VSLTCLVKGFYPSDIAVEWESNGQPENNYKTTPPVLDSDGSFFLYSKLT VDKSRWQQGNVFSCSVMHEALHNHYTQKSLSLSPGK (SEQ ID NO: 32) |
| | Linker | | GGGGSGGGGSGGGGS (SEQ ID NO: 34) |
| | scFv of 1A10 | VL | QSVLTQPPSASGTPGQRVTISCSGSSSNIGNNYVTWYQQLPGTAPKLLI YADSHRPSGVPDRFSGSKSGTSASLAISGLRSEDEADYYCATWDYSLSG YVFGCGTKLTVL (SEQ ID NO: 25) |
| | | Linker | GGGGSGGGGSGGGGSGGGGS (SEQ ID NO: 35) |
| | | VH | EVQLLESGGGLVQPGGSLRLSCAASGFTFSSYDMSWVRQAPGKCLEWVS WISYSGGSIYYADSVKGRFTISRDNSKNTLYLQMNSLRAEDTAVYYCAR DAQRNSMREFDYWGQGTLVTVSS (SEQ ID NO: 24) |
| Light component | Light chain of 120B762 | | DIVMTQSPDSLAVSLGERATINCKSSQSLLNAGNQKNYLTWYQQKPGQP PKLLIYWASTRESGVPDRFSGSGSGTDFTLTISSLQAEDVAVYYCQNAY YFPFTFGGGTKLEIK (SEQ ID NO: 31) RTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPV TKSFNRGEC (SEQ ID NO: 33) |

The 4F11E2 and 1A10 sequences were also used to generate bispecific antibodies of two different formats, as illustrated in FIG. 1B and FIG. 1C, respectively. In the format of FIG. 1B, the anti-Claudin 18.2 portion also took a Fab format, while the anti-4-1BB portion was present as a scFab fragment inserted between the anti-Claudin 18.2 Fab and the Fc fragments. The IgG1 (N297A) was also used here.

TABLE 2

Antibody of Format of FIG. 1B

Fab-scFab-Fc

| | | | |
|---|---|---|---|
| Heavy component (SEQ ID NO: 54) | Heavy chain of 4F11E2 | | EVQLVESGGGLVQPGGSLRLSCAASGFTFSTFGMHWVRQAPGKGLEWV SYITSGESPIYFTDTVKGRFTISRDNAKNSLYLQMNSLRAEDTAVYYC ARSSYYGNSMDYWGQGTLVTVSS (SEQ ID NO: 26) ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KVEPKSC (SEQ ID NO: 36) |
| | Linker | | GGGGSGGGGSGGGGSGGGGS (SEQ ID NO: 35) |
| | scFab of 1A10 | Light chain of 1A10 | QSVLTQPPSASGTPGQRVTISCSGSSSNIGNNYVTWYQQLPGTAPKLL IYADSHRPSGVPDRFSGSKSGTSASLAISGLRSEDEADYYCATWDYSL SGYVFGGGTKLTVL (SEQ ID NO: 53) GQPKANPTVTLFPPSSEELQANKATLVCLISDFYPGAVTVAWKADGSP VKAGVETTKPSKQSNNKYAASSYLSLTPEQWKSHRSYSCQVTHEGSTV EKTVAPTECS (SEQ ID NO: 37) |
| | | Linker | GSGSGSGSGSGSGSGSGGGGSGGGGSGGGGSGGGGSGGGGSGGGGS GSGSGSGSGSGSGS (SEQ ID NO: 38) |
| | | Heavy chain of 1A10 | EVQLLESGGGLVQPGGSLRLSCAASGFTFSSYDMSWVRQAPGKGLEWV SWISYSGGSIYYADSVKGRFTISRDNSKNTLYLQMNSLRAEDTAVYYC ARDAQRNSMREFDYWGQGTLVTVSS (SEQ ID NO: 47) ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KVEPKSCDKTHTCPPCPAPELLGGPSVFLFPPKPKDTLMISRTPEVTC VVVDVSHEDPEVKFNWYVDGVEVHNAKTKPREEQYASTYRVVSVLTVL HQDWLNGKEYKCKVSNKALPAPIEKTISKAKGQPREPQVYTLPPSREE MTKNQVSLTCLVKGFYPSDIAVEWESNGQPENNYKTTPPVLDSDGSFF LYSKLTVDKSRWQQGNVFSCSVMHEALHNHYTQKSLSLSPGK (SEQ ID NO: 32) |

TABLE 2-continued

Antibody of Format of FIG. 1B

Fab-scFab-Fc

| Light component (SEQ ID NO: 41) | Light chain of 4F11E2 | DIVMTQSPDSLAVSLGERATINCRSSQSLLNAGNRKNYLTWYQQKPGQ PPKLLIYWASTRESGVPDRFSGSGSGTDFTLTISSLQAEDVAVYYCQN AYSYPFTFGGGTKLEIK (SEQ ID NO: 27) RTVAAPSVFIFPPSDEQLKSGTASVVCLLNNFYPREAKVQWKVDNALQ SGNSQESVTEQDSKDSTYSLSSTLTLSKADYEKHKVYACEVTHQGLSS PVTKSFNRGEC (SEQ ID NO: 33) |

In the format of FIG. 1C, the anti-Claudin 18.2 portion was present in full IgG1, while the anti-4-1BB portion was a scFab fragment placed at the C-terminal side of the Fc.

TABLE 3

Antibody of Format of FIG. 1C

IgG-scFab

| Heavy component (SEQ ID NO: 55) | Heavy chain of 4F11E2 | EVQLVESGGGLVQPGGSLRLSCAASGFTFSTFGMHWVRQAPGKGLE WVSYITSGESPIYFTDTVKGRFTISRDNAKNSLYLQMNSLRAEDTA VYYCARSSYYGNSMDYWGQGTLVTVSS (SEQ ID NO: 26) ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVDVSHEDPEVKFNWYVDGVEVHNAKTKPREEQYASTYR VVSVLTVLHQDWLNGKEYKCKVSNKALPAPIEKTISKAKGQPREPQ VYTLPPSREEMTKNQVSLTCLVKGFYPSDIAVEWESNGQPENNYKT TPPVLDSDGSFFLYSKLTVDKSRWQQGNVFSCSVMHEALHNHYTQK SLSLSPGK (SEQ ID NO: 32) |
| | Linker | GGGGSGGGGSGGGGS (SEQ ID NO: 34) |
| | scFab of 1A10 | Light chain of 1A10 | QSVLTQPPSASGTPGQRVTISCSGSSSNIGNNYVTWYQQLPGTAPK LLIYADSHRPSGVPDRFSGSKSGTSASLAISGLRSEDEADYYCATW DYSLSGYVFGGGTKLTVL (SEQ ID NO: 53) GQPKANPTVTLFPPSSEELQANKATLVCLISDFYPGAVTVAWKADG SPVKAGVETTKPSKQSNNKYAASSYLSLTPEQWKSHRSYSCQVTHE GSTVEKTVAPTECS (SEQ ID NO: 37) |
| | Linker | GSGSGSGSGSGSGSGSGSGGGGSGGGGSGGGGSGGGGSGGGGSGGG GSGSGSGSGSGSGSGS (SEQ ID NO: 38) |
| | Heavy chain of 1A10 | EVQLLESGGGLVQPGGSLRLSCAASGFTFSSYDMSWVRQAPGKGLE WVSWISYSGGSIYYADSVKGRFTISRDNSKNTLYLQMNSLRAEDTA VYYCARDAQRNSMREFDYWGQGTLVTVSS (SEQ ID NO: 47) ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSC (SEQ ID NO: 36) |
| Light component (SEQ ID NO: 41) | Light chain of 4F11E2 | DIVMTQSPDSLAVSLGERATINCRSSQSLLNAGNRKNYLTWYQQKP GQPPKLLIYWASTRESGVPDRFSGSGSGTDFTLTISSLQAEDVAVY YCQNAYSYPFTFGGGTKLEIK (SEQ ID NO: 27) RTVAAPSVFIFPPSDEQLKSGTASVVCLLNNFYPREAKVQWKVDNA LQSGNSQESVTEQDSKDSTYSLSSTLTLSKADYEKHKVYACEVTHQ GLSSPVTKSFNRGEC (SEQ ID NO: 33) |

The bispecific antibodies of the formats in FIGS. 1B and 1C were outperformed by those of format in FIG. 1A in terms of 4-1BB binding, in preliminary testing. Thus, only those of format FIG. 1A underwent additional testing as shown below. Further, E-1A10 was slightly less potent than C-1A10 and D-1A10 and was thus also not included in further studies.

Example 2. Antigen Binding of the Anti-CLDN18.2/4-1BB Bispecific Antibodies

This example evaluated the binding activities of the bispecific antibodies of Example 1 to CLDN18.2 and 4-1BB, using protein-based and cell-based assays.

2.1 ELISA Binding to 4-IBB

Briefly, microtiter plates were coated with 100 µl human 4-1BB-His protein at 0.5 µg/ml diluted in PBS at 4° C. overnight, then blocked with 100 µl/well of 1% BSA. Three-fold dilution of antibodies starting from 100 nM were added to each well and incubated for 2 hours at RT. The plates were washed with PBS/Tween and then incubated with goat-anti-human IgG antibody conjugated with Horse Radish Peroxidase (HRP) for 30 minutes at RT. After washing, the plates were developed with TMB substrate and analyzed by plate reader at OD450 nm. As shown in FIG. 2A, the anti-CLDN18.2-4-1BB antibodies (C-1A10 and D-1A10) showed comparable binding as anti-4-1BB monoclonal antibodies (1A10, and urelumab (BMUR)).

2.2 ELISA Binding to CLDN18.2

To text CLDN18.2 binding, the CLDN18.2 protein was expressed in a Virus Like Particle (VLP) to mimic the nature conformation. Similarly, microtiter plates were coated with 100 µl CLDN18.2 VLP at 3 µg/ml diluted in PBS at 4° C. overnight, then blocked with 300 µl/well of 3% BSA. Three-fold dilution of antibodies starting from 100 nM were added to each well and incubated for 2 hours at 37° C. The plates were washed with PBS/Tween and then incubated with goat-anti-human IgG antibody conjugated with Horse Radish Peroxidase (HRP) for 30 minutes at RT. After washing, the plates were developed with TMB substrate and analyzed by plate reader at OD450 nm. As shown in FIG. 2B, the anti-CLDN18.2-4-1BB antibodies (C-1A10 and D-1A10) showed stronger binding than the anti-CLDN18.2 monoclonal antibody (I-MAB362). Meanwhile, in the same experiment setting, the binding to CLDN18.1 protein was tested as well. As shown in FIG. 2C, no antibody showed cross-reactivity to CLDN18.1.

2.3 ELISA Binding to Dual Antigen

Figure 2D:
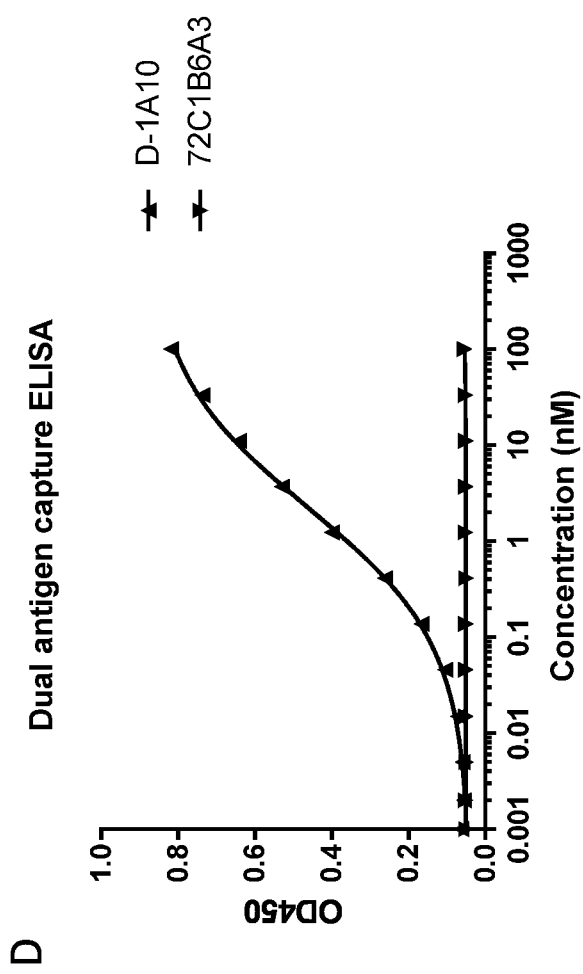

To further demonstrate that the anti-CLDN18.2-4-1BB antibodies can bind to CLDN18.2 and 4-1BB simultaneously, a DACE (Dual antigen captured ELISA) test was performed. Briefly, microtiter plate was coated with 100 µl CLDN18.2 VLP at 3 µg/ml diluted in PBS at 4° C. overnight. Then, three-fold dilution of antibodies starting from 100 nM were added to each well and incubated for 2 hours at 37° C. After washing, the plate was then incubated with 100 µl human 4-1BB-biotin protein at a concentration of 1 µg/ml for 1 hour at 37° C. and followed with Streptavidin HRP for another 30 minutes at room temperature. After washing, the plates were developed with TMB substrate and analyzed by plate reader at OD 450 nm. As shown in FIG. 2D, D-1A10 can bind to hCLDN18.2 and 4-1BB at the same time. On the contrast, CLDN18.2 mAb 72C1B6A3 showed no signal in this assay.

2.4 Cell-Based Binding to 4-IBB

Figure 3:
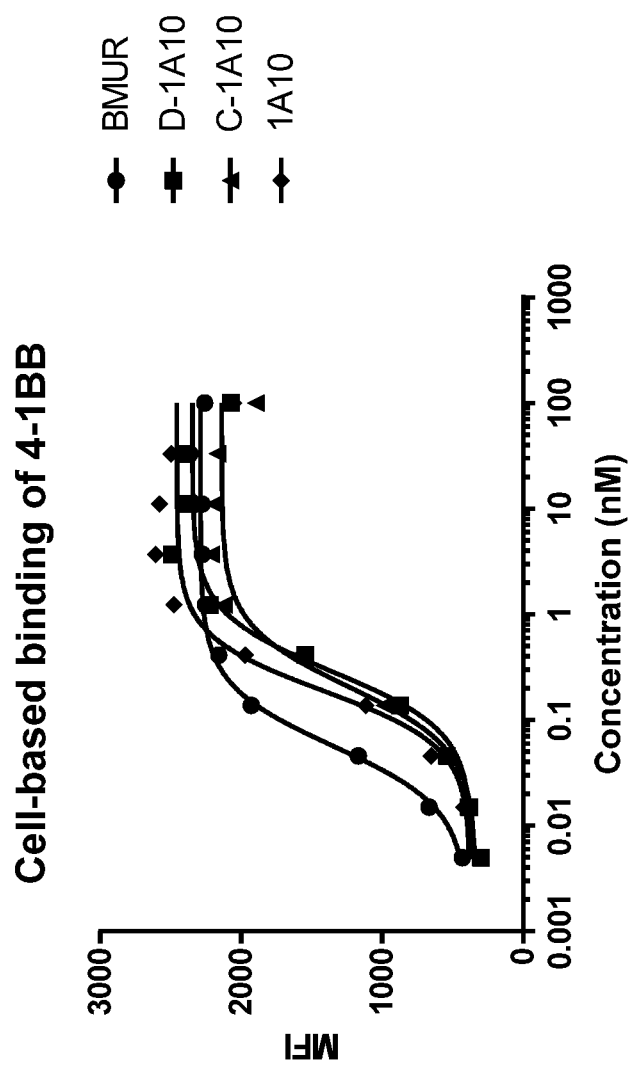
FIG. 3 shows the cell-based 4-1BB binding.

To evaluate the antigen binding property, the anti-CLDN18.2-4-1BB antibodies were analyzed for their binding to HEK293 expressed 4-1BB by FACS. A total number of $1 \times 10^5$ HEK293-4-1BB cells in each well were incubated with serial diluted antibodies for 30 minutes at 4° C. in FACS buffer (2% FBS in PBS). After wash by FACS buffer, PE conjugated-anti-human IgG antibody was added to each well and incubated at 4° C. for 30 minutes. After wash, MFI of PE was evaluated by FACS Caliber. As shown in FIG. 3, the anti-CLDN18.2-4-1BB antibodies (C-1A10 and D-1A10) tested showed concentration-dependent binding abilities to 4-1BB, comparable with the monoclonal antibodies (1A10 and BMUR).

2.5 Cell-Based Binding to CLDN18.2

To evaluate the binding capability towards CLDN18.2, a CHO-K1 cell line which stably expressed human CLDN18.2 was made. CHO-C18.2 cell line was then sorted for high expressers (CHO-K1 C18.2 High) and low expressers (CHO-K1 C18.2 Low) using flow cytometry. CHO-K1-C18.2 cells were incubated with serial diluted antibodies for 30 minutes at 4° C. in FACS buffer. After wash by FACS buffer, PE conjugated-anti-human IgG antibody was added and incubated at 4° C. for 30 minutes. MFI of PE was evaluated by FACS. As shown in FIGS. 4A and 4B, anti-CLDN18.2-4-1BB antibodies bound to CLDN18.2-expressed cells in a concentration-dependent manner; meanwhile, both of the bispecific antibodies showed stronger binding than IMAB362, a reference monoclonal anti-CLDN18.2 antibody currently in clinical trials.

Figure 4C:
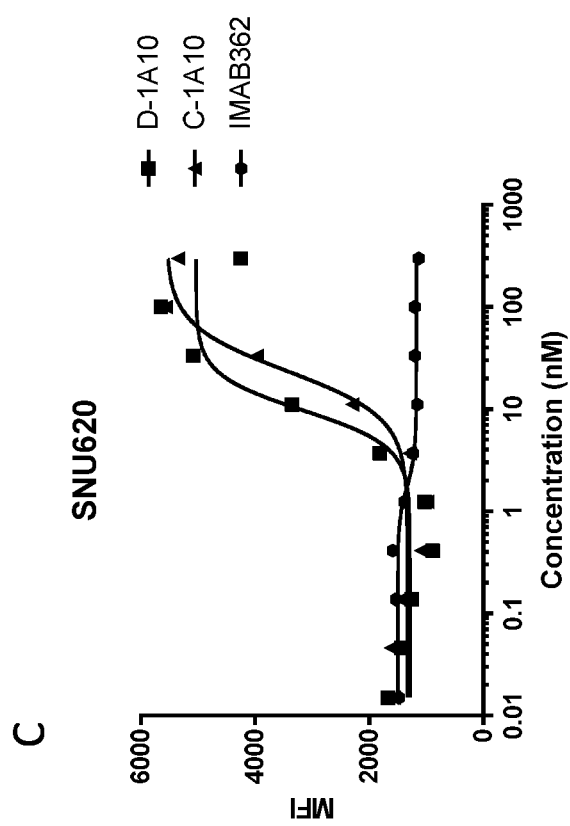

SNU620 is a gastric carcinoma cell line with endogenous CLDN18.2 expression. As shown in FIG. 4C, the anti-CLDN18.2-4-1BB bispecific antibodies could bind to SNU620 as well.

Example 3. Functional Activity of Anti-CLDN18.2/4-1BB Bispecific Antibodies 3.1 Cell-Line Based Functional Characterization of CLDN18.2-4-IBB Bispecific Antibody To test the ability of the bispecific antibodies to promote 4-1BB signal, a commercial 4-1BB assay was used. In this assay, GloResponse™ NFκB-luc2/4-1BB Jurkat cell line (Promega, cat #CS196004) was used as effector cells and CHO-K1-expressing or not expressing CLDN18.2 or SNU620 as target cells. GloResponse™ NFκB-luc2/4-1BB Jurkat cell line is genetically modified to stably express 4-1BB and luciferase downstream of a response element. Luciferase expression is induced upon antibody binding to the 4-1BB receptor. In brief, effector cells at a density of $2.5 \times 10^4$ cells per well were mixed with $2.5 \times 10^4$ target cells in a white 96-well plate. Antibodies 6-fold serially diluted were added to a white 96-well assay plate, at a final concentration ranging from 16.7 nM to 0.28 fm. After 6 hours' incubation at 37° C., luminescence was obtained by adding the substrate of luciferase and measured by a microplate reader (PHERAstar). Four-parameter logistic curve analysis was performed with GraphPad software.

As shown in FIG. 5, the BMUR monoclonal antibody can dose-dependent boost the 41BB singling, while the 1A10 monoclonal antibody had no agonist activity in the same experimental settings. The activity of anti-CLDN18.2-4-1BB bispecific antibodies D-1A10 and C-1A10 was dependent on the expression of CLDN18.2.

Figure 6A:
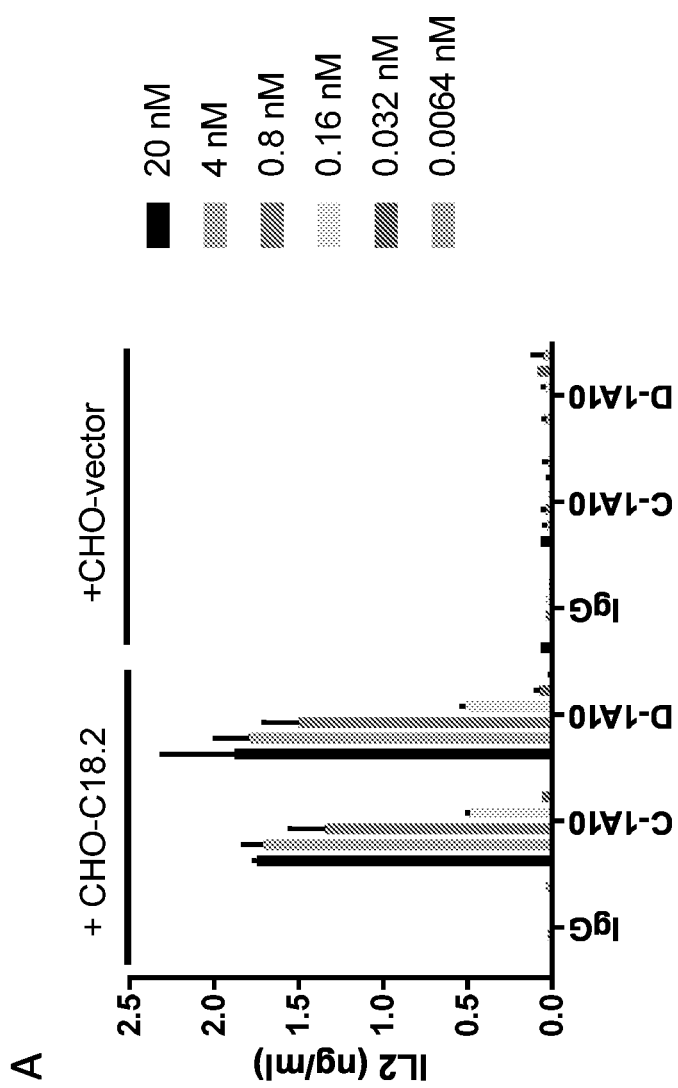

3.2 Activity of the Bispecific Antibodies to Promote Human Peripheral Blood Mononuclear Cell (PBMC) Immune Response To test the ability of bispecific antibodies to stimulated human PBMCs response, cytokine production assay was used. Human PBMCs stimulated with 0.5 µg/ml human anti-CD3 antibody were used as the effector cells. CHO-K1 express CLDN18.2 was used as the target cells. Human PBMCs ($1 \times 10^5$) were co-cultured with CHO-K1-CLDN18.2 or control CHO-K1 cells ($2.5 \times 10^4$) in the presence of human anti-CD3 antibody. Serially diluted bispecific antibodies were added to the mixed culture at a final concentration starting from 20 nM. 48 hours later, the level of IL2 and IFN-γ in the culture medium was measured using IL-2 (human) LANCE Ultra TR-FRET Detection Kit and IFN-γ (human) LANCE Ultra TR-FRET Detection Kit (PerkinElmer). As shown in FIG. 6, only bispecific antibodies can activate PBMC response in the presence of CLDN18.2 expressing cells.

To further demonstrate that the activity of bispecific antibodies was correlated with CLDN18.2 level, human PBMC from one donor were cocultured with different Gastric Adenocarcinoma (GA) PDX derived cells, which was proved to express different level of C18.2. Serially diluted bispecific antibodies were added to the mixed culture at a final concentration starting from 20 nM. After 48 hours, the level of IL2 in the culture medium was measured using IL-2 (human) LANCE Ultra TR-FRET Detection Kit (PerkinElmer). As shown in FIGS. 6D and 6E, the activity of bispecific antibody D-1A10 correlated with CLDN18.2 level. D-1A10 effectively activated T cells even in CLDN18.2 low- to middle-expressed tumors.

3.3 Activity of the Bispecific Antibodies to Promote Human CD8+ T Cell Response

To further test the ability of bispecific antibodies in activating human CD8+ T cell, human CD8+ T cells isolated from PBMCs were used as the effector cells. CHO-K1 expressed CLDN18.2 or SNU620 was used as the target cells. Isolated CD8+ T cells (7.5×10⁴) were co-cultured with target cells (2.5×10⁴) in the presence of human anti-CD3 antibody. Serially diluted bispecific antibodies were added to the mixed culture at a final concentration starting from 20 nM. The level of IL2 and IFN-γ in the culture medium was measured 48 hours after coculture, using IL-2 (human) LANCE Ultra TR-FRET Detection Kit and IFN-γ (human) LANCE Ultra TR-FRET Detection Kit (PerkinElmer). As shown in FIG. 7, bispecific antibodies C-1A10 and D-1A10 can both increase the production of IL2 and IFN-γ of activated CD8+ T cells in the presence of C18.2 overexpressing CHO-K1 (FIG. 7A-7B) or SNU620 which endogenously express C18.2 (FIG. 7C-7D).

Example 4. Tumor Growth Inhibition by Anti-CLDN18.2-4-1BB Bispecific Antibodies

Humanized mice that expressed the extracellular domain of human 4-1BB were used. Mouse colon adenocarcinoma cells (MC38) were engineered to express human CLDN18.2. Humanized mice (h4-1BB) were subcutaneously implanted with MC38-hCLDN18.2 cells. Mouse were intraperitoneally administered every 3 days for 5 times with following antibodies: isotype control (10 mg/kg), anti-CLDN18.2 antibody (10 mg/kg), anti-4-1BB antibody (10 mg/kg), combination of anti-CLDN18.2 (10 mg/kg) and anti-4-1BB (10 mg/kg) and anti-CLDN18.2-4-1BB bispecific antibody (13.3 mg/kg). Tumor volumes were monitored by caliper measurement twice per week for the duration of the experiment. Tumor growth inhibition induced by bispecific antibodies was significantly greater than that observed with the combination of each targeting monoclonal antibodies, shown in FIG. 8. To further understand the mechanism of the antibody, tumor infiltrated lymphocytes and peripheral lymphocytes were collected and analyzed for the percentage of CD3+ T cells by flow cytometry. Results showed that bispecific antibodies can specifically increase the number of CD3+ T cells in the tumor microenvironment, while had no impact on peripheral blood.

Figure 9A:
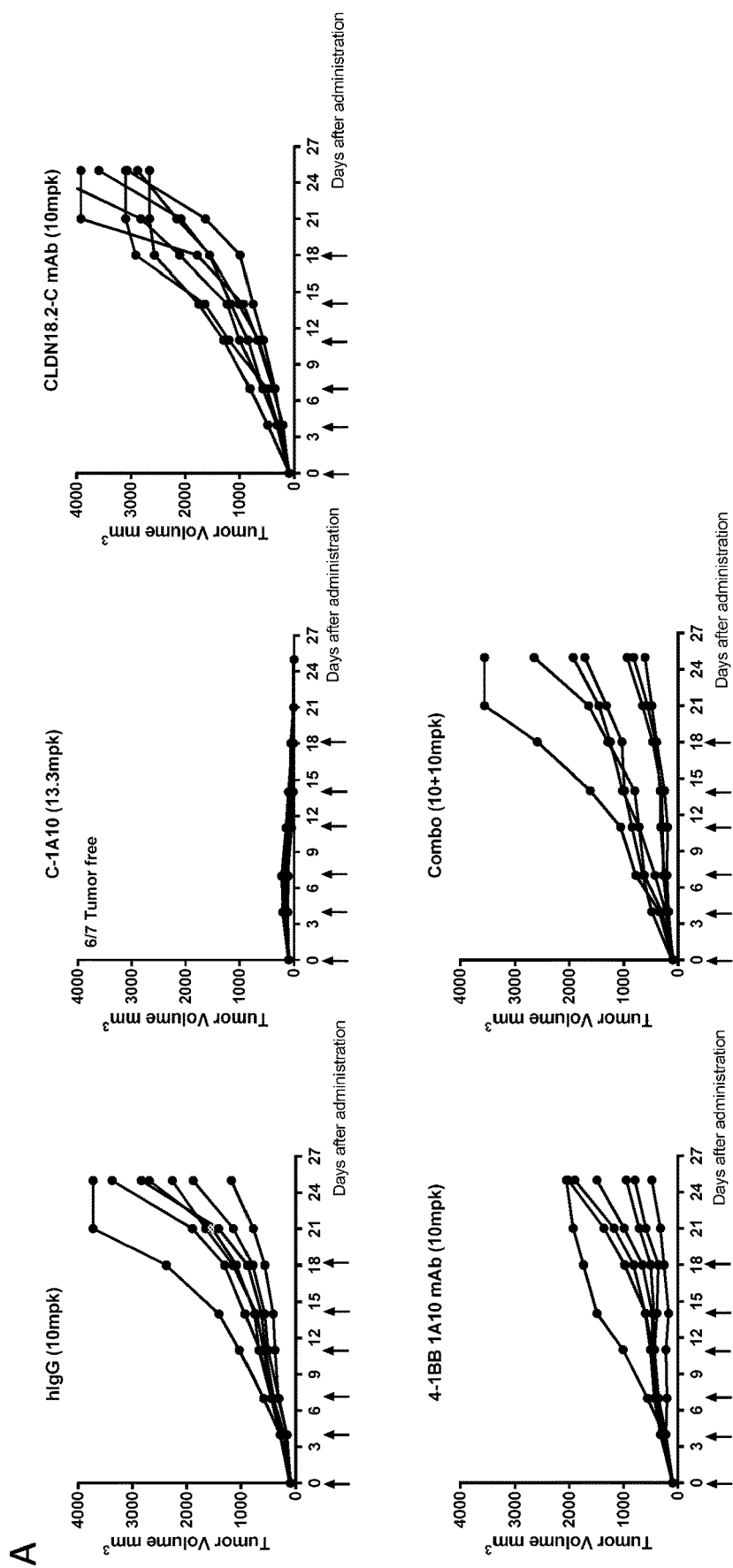
FIG. 9A-C show in vivo efficacy of C-1A10 bispecific antibody in syngeneic mouse model.

In another repeated experiment using the same animal model, the in vivo efficacy was further proved. The FIG. 9A showed the tumor growth curve of each animal in each group. The tumor growth inhibition of anti-CLDN18.2-4-1BB antibody (C-1A10) reached 105% at the end of study. Six of 7 mice in the group of bispecific were tumor free by day 25 following the first treatment.

Figures 9B, 9C:
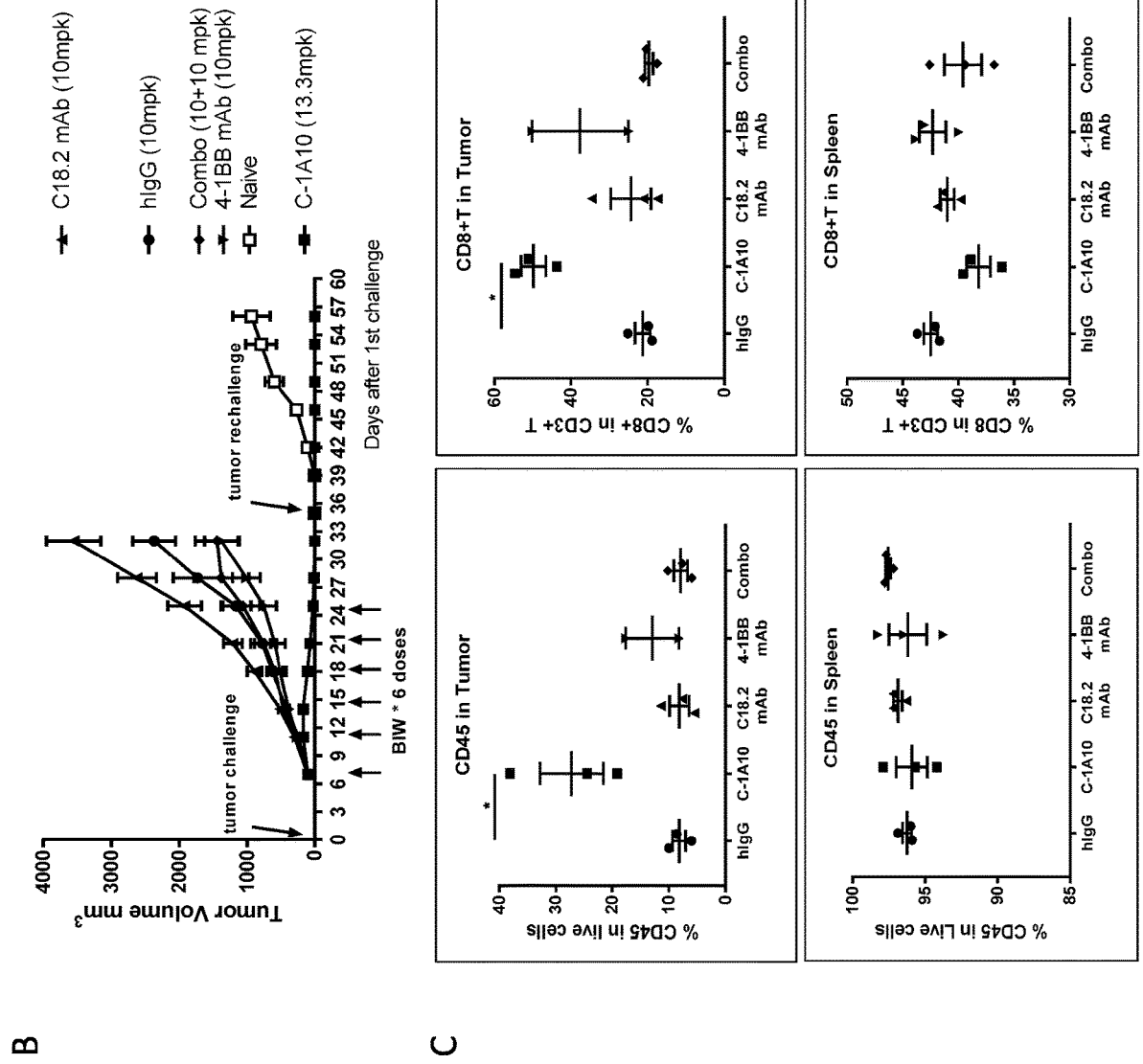

In addition, this example re-challenged all anti-CLDN18.2-4-1BB antibody (C-1A10)-treated animals with a second dose of MC38-hCLDN18.2 tumor cells in the contralateral flank 35 days after the first tumor inoculation and monitored tumor growth without giving additional treatment. Results showed that as the tumor cells continued to grow in naïve mice, all BsAb-treated mice were resistant to tumor re-challenge and were deemed tumor free till the end of the study (FIG. 9B), suggesting that the present bispecific antibodies can induce long-term protective immunological memory again MC38 tumors. Similarly, in a satellite group (N=3/group) where mice received the same treatment, tumors were extracted 3 days after the second dose of antibodies to quantify tumor-infiltrating lymphocytes (TILs). The percentage of CD45+ and CD8+TILs was significantly higher in BsAb treatment group. In contrast, there was no effect on the peripheral lymphocytes (FIG. 9C).

Figure 10:
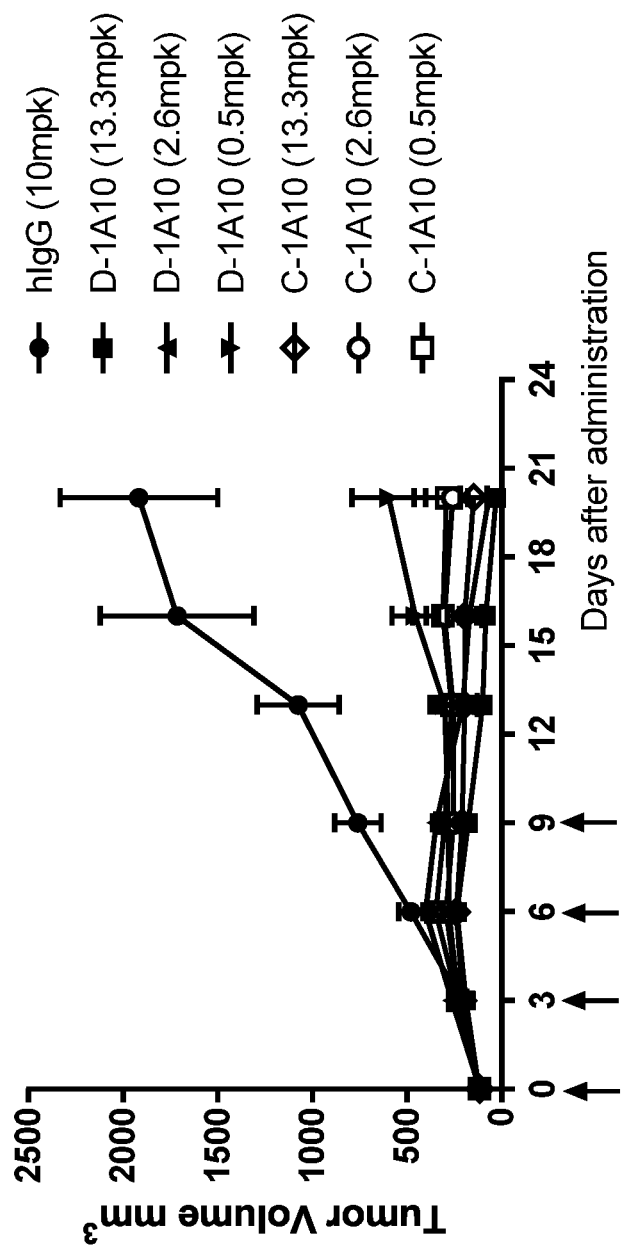
FIG. 10 shows dose-dependent anti-tumor efficacy of C-1A10 and D-1A10 in syngeneic mouse model.

To further evaluate the anti-tumor efficacy of anti-CLDN18.2-4-1BB bispecific antibodies, different concentrations of bispecific antibodies were given to 4-1BB humanized mice implanted with MC38-hCLDN18.2 antibodies. Mouse were intraperitoneally administered every 3 days for 4 times with following antibodies: isotype control (10 mg/kg), C-1A10 (13.3 mg/kg), C-1A10 (2.6 mg/kg), C-1A10 (0.5 mg/kg), D-1A10 (13.3 mg/kg), D-1A10 (2.6 mg/kg), D-1A10 (0.5 mg/kg). Tumor volumes were monitored by caliper measurement twice per week for the duration of the experiment. As shown in FIG. 10, both C-1A10 and D-1A10 can suppress the tumor growth in a dose-dependent manner.

To understand the pharmacokinetics (PK) and pharmacodynamics relationship of anti-CLDN18.2-4-1BB in humanized mouse mode, single administration of D-1A10 at 3 different concentrations was given to tumor bearing—humanized mice. Serum concentration was measured at various time points. As showed in FIG. 11, overall, it displayed a dose-dependent PK profile. And the in vivo efficacy was correlated with the dose level. Ex vivo TIL analysis suggested a dose-dependent increase of CD8+ cells and CD45+ cells.

Example 5. Testing of Additional Conditional Agonist Full Human Anti-4-1BB Antibodies The following anti-4-1BB antibodies were identified for their ability to bind to 4-1BB at high affinity and not to activate 4-1BB signaling upon binding.

TABLE 4

Additional Anti-4-1BB Antibodies

| Antibody No. | VH | SEQ ID NO: |
|---|---|---|
| 41B01 | EVQLLESGGGLVQPGGSLRLSCAASGFTFS<u>SYDMS</u>WVRQAPGKGLEWVS<u>WIS YSGGSIYYADSVKG</u>RFTISRDNSKNTLYLQMNSLRAEDTAVYYCARDGQRNS MREFDYWGQGTLVTVSS | 46 |
| 41B01.01 | EVQLLESGGGLVQPGGSLRLSCAASGFTFS<u>SYDMS</u>WVRQAPGKGLEWVS<u>WIS YSGGSIYYADSVKG</u>RFTISRDNSKNTLYLQMNSLRAEDTAVYYCARDAQRNS MREFDYWGQGTLVTVSS | 47 |
| 41B01.02 | EVQLLESGGGLVQPGGSLRLSCAASGFTFS<u>SYDMS</u>WVRQAPGKGLEWVS<u>WIS YSGGSIYYADSVKG</u>RFTISRDNSKNTLYLQMNSLRAEDTAVYYCARDAQRQS MREFDYWGQGTLVTVSS | 48 |
| 41B01.03 | EVQLLESGGGLVQPGGSLRLSCAASGFTFS<u>SYDMS</u>WVRQAPGKGLEWVS<u>WIS YSGGSIYYADSVKG</u>RFTISRDNSKNTLYLQMNSLRAEDTAVYYCARDGQRQS MREFDYWGQGTLVTVSS | 49 |
| 41B01.04 | EVQLLESGGGLVQPGGSLRLSCAASGFTFS<u>SYDMS</u>WVRQAPGKGLEWVS<u>WIS YSGGSIYYADSVKG</u>RFTISRDNSKNTLYLQMNSLRAEDTAVYYCARDAQRNA MREFDYWGQGTLVTVSS | 50 |

TABLE 4-continued

Additional Anti-4-1BB Antibodies

| | | |
|---|---|---|
| 41B02 | EVQLLESGGGLVQPGGSLRLSCAASGFTFS<u>GYDMS</u>WVRQAPGKGLEWVS<u>VIY PDDGNTYYADSVKG</u>RFTISRDNSKNTLYLQMNSLRAEDAAVYYCAK<u>HGGQKP TTKSSSAYGMDG</u>WGQGTLVTVSS | 51 |

| Antibody No. | VL | SEQ ID NO: |
|---|---|---|
| 41B01 | QSVLTQPPSASGTPGRRVTISC<u>SGSSSNIGNNYVT</u>WYQQLPGTAPKLLIY<u>AD SHRPS</u>GVPDRFSGSKSGTSASLAISGLRSEDEADYYC<u>ATWDYSLSGYV</u>FGGG TKLTVL | 52 |
| 41B01.01 | QSVLTQPPSASGTPGRRVTISC<u>SGSSSNIGNNYVT</u>WYQQLPGTAPKLLIY<u>AD SHRPS</u>GVPDRFSGSKSGTSASLAISGLRSEDEADYYC<u>ATWDYSLSGYV</u>FGGG TKLTVL | 52 |
| 41B01.02 | QSVLTQPPSASGTPGRRVTISC<u>SGSSSNIGNNYVT</u>WYQQLPGTAPKLLIY<u>AD SHRPS</u>GVPDRFSGSKSGTSASLAISGLRSEDEADYYC<u>ATWDYSLSGYV</u>FGGG TKLTVL | 52 |
| 41B01.03 | QSVLTQPPSASGTPGQRVTISC<u>SGSSSNIGNNYVT</u>WYQQLPGTAPKLLIY<u>AD SHRPS</u>GVPDRFSGSKSGTSASLAISGLRSEDEADYYC<u>ATWDYSLSGYV</u>FGGG TKLTVL | 53 |
| 41B01.04 | QSVLTQPPSASGTPGQRVTISC<u>SGSSSNIGNNYVT</u>WYQQLPGTAPKLLIY<u>AD SHRPS</u>GVPDRFSGSKSGTSASLAISGLRSEDEADYYC<u>ATWDYSLSGYV</u>FGGG TKLTVL | 53 |
| 41B02 | QSVLTQPPSASGTPGRRVTISC<u>SGSSSNIGNNYVT</u>WYQQLPGTAPKLLIY<u>AD SHRPS</u>GVPDRFSGSKSGTSASLAISGLRSEDEADYYC<u>ATWDYSLSGYV</u>FGGG TKLTVL | 52 |

CDRs for VHs in Table 4

| SEQ ID NO | VH_CDR1 | SEQ ID NO | VH_CDR2 | SEQ ID NO | VH_CDR3 |
|---|---|---|---|---|---|
| 1 | SYDMS | 2 | WISYSGGSIYYADSVKG | 3 | DAQRNSMREFDY |
| | | | | 56 | DGQRNSMREFDY |
| | | | | 57 | DAQRQSMREFDY |
| | | | | 58 | DGQRQSMREFDY |
| | | | | 59 | DAQRNAMREFDY |
| 60 | GYDMS | 61 | VIYPDDGNTYYADSVKG | 62 | HGGQKPTTKSSSAYGMDG |

TABLE 5

VHs and VLs of Anti-4-1BB scFv

| Antibody No. | VH | SEQ ID NO: |
|---|---|---|
| 41B01 | EVQLLESGGGLVQPGGSLRLSCAASGFTFS<u>SYDMS</u>WVRQAPGKCLEWVS<u>WIS YSGGSIYYADSVKG</u>RFTISRDNSKNTLYLQMNSLRAEDTAVYYCARD<u>GQRNS MREFDY</u>WGQGTLVTVSS | 63 |
| 41B01.01 | EVQLLESGGGLVQPGGSLRLSCAASGFTFS<u>SYDMS</u>WVRQAPGKCLEWVS<u>WIS YSGGSIYYADSVKG</u>RFTISRDNSKNTLYLQMNSLRAEDTAVYYCARD<u>AQRNS MREFDY</u>WGQGTLVTVSS | 64 |
| 41B01.03 | EVQLLESGGGLVQPGGSLRLSCAASGFTFS<u>SYDMS</u>WVRQAPGKCLEWVS<u>WIS YSGGSIYYADSVKG</u>RFTISRDNSKNTLYLQMNSLRAEDTAVYYCARD<u>AQRNS MREFDY</u>WGQGTLVTVSS | 65 |
| 41B01.04 | EVQLLESGGGLVQPGGSLRLSCAASGFTFS<u>SYDMS</u>WVRQAPGKCLEWVS<u>WIS YSGGSIYYADSVKG</u>RFTISRDNSKNTLYLQMNSLRAEDTAVYYCARD<u>AQRQS MREFDY</u>WGQGTLVTVSS | 66 |
| 41B02 | EVQLLESGGGLVQPGGSLRLSCAASGFTFS<u>GYDMS</u>WVRQAPGKCLEWVS<u>VIY PDDGNTYYADSVKG</u>RFTISRDNSKNTLYLQMNSLRAEDAAVYYCAK<u>HGGQKP TTKSSSAYGMDG</u>WGQGTLVTVSS | 67 |
| 41B02.01 | EVQLLESGGGLVQPGGSLRLSCAASGFTFS<u>GYDMS</u>WVRQAPGKCLEWVS<u>VIY PDDGNTYYADSVKG</u>RFTISRDNSKNTLYLQMNSLRAEDTAVYYCAK<u>HGGQKP TTKSSSAYGMDG</u>WGQGTLVTVSS | 68 |

| Antibody No. | VL | SEQ ID NO: |
|---|---|---|
| 41B01 | QSVLTQPPSASGTPGRRVTISC<u>SGSSSNIGNNYVT</u>WYQQLPGTAPKLLIY<u>AD SHRPS</u>GVPDRFSGSKSGTSASLAISGLRSEDEADYYC<u>ATWDYSLSGYV</u>FGCG TKLTVL | 69 |
| 41B01.01 | QSVLTQPPSASGTPGRRVTISC<u>SGSSSNIGNNYVT</u>WYQQLPGTAPKLLIY<u>AD SHRPS</u>GVPDRFSGSKSGTSASLAISGLRSEDEADYYC<u>ATWDYSLSGYV</u>FGCG TKLTVL | 70 |

TABLE 5-continued

VHs and VLs of Anti-4-1BB scFv

| 41B01.03 | QSVLTQPPSASGTPGQRVTISC<u>SGSSSNIGNNYVT</u>WYQQLPGTAPKLLIY<u>AD</u><u>SHRP</u>SGVPDRFSGSKSGTSASLAISGLRSEDEADYY<u>CATWDYSLSGYV</u>FGCGTKLTVL | 71 |
|---|---|---|
| 41B01.04 | QSVLTQPPSASGTPGQRVTISC<u>SGSSSNIGNNYVT</u>WYQQLPGTAPKLLIY<u>AD</u><u>SHRP</u>SGVPDRFSGSKSGTSASLAISGLRSEDEADYY<u>CATWDYSLSGYV</u>FGCGTKLTVL | 72 |
| 41B02 | QSVLTQPPSASGTPGRRVTISC<u>SGSSSNIGNNYVT</u>WYQQLPGTAPKLLIY<u>AD</u><u>SHRP</u>SGVPDRFSGSKSGTSASLAISGLRSEDEADYY<u>CATWDYSLSGYV</u>FGCGTKLTVL | 73 |
| 41B02.01 | QSVLTQPPSASGTPGQRVTISC<u>SGSSSNIGNNYVT</u>WYQQLPGTAPKLLIY<u>AD</u><u>SHRP</u>SGVPDRFSGSKSGTSASLAISGLRSEDEADYY<u>CATWDYSLSGYV</u>FGCGTKLTVL | 74 |

5.1 Antigen Binding Measured by ELISA

To evaluate the antigen binding activity, the antibodies were subjected to ELISA test. Briefly, microtiter plates were coated with human 4-1BB-Fc protein at 0.1 µg/ml in PBS, 100 µl/well at 4° C. overnight, then blocked with 100 µl/well of 5% BSA. Five-fold dilutions of the antibodies starting from 10 µg/ml were added to each well and incubated for 1-2 hours at RT. The plates were washed with PBS/Tween and then incubate with goat-anti-human IgG antibody conjugated with Horse Radish Peroxidase (HRP) for 1 hour at RT. After washing, the plates were developed with TMB substrate and analyzed by spectrophotometer at OD 450-630 nm. The anti-4-1BB antibodies tested showed 4-1BB binding abilities.

5.2 Cell Binding Measured by FACS

To evaluate the antigen binding property, the antibody candidates were analyzed for its binding to mammalian expressed 4-1BB by FACS. Briefly, 4-1BB-Jurkat cells were incubated with the antibodies. After wash by FACS buffer (1% BSA in PBS), the FITC-anti-human IgG antibody was added to each well and incubated at 4° C. for 1 hour. The MFI of FITC was evaluated by FACS Caliber. The anti-4-1BB antibodies tested showed binding abilities to 4-1BB which expressed on cell surface and can efficiently bind to 4-1BB expressed on mammalian cells.

5.3 Protein Kinetic for 4-IBB

To explore the binding kinetics of the antibodies, this example performed the affinity ranking by using Octet Red 96. As shown in Table 5, the anti-4-1BB antibodies tested had high 4-1BB binding affinities.

TABLE 5

Binding Kinetics

| Antibody | KD (M) | kon (1/Ms) | kdis (1/s) | Chi | $R^2$ |
|---|---|---|---|---|---|
| 41B01 | 1.80E−10 | 6.58E+05 | 1.19E−04 | 0.0392 | 0.9987 |
| 41B02 | 1.01E−09 | 5.95E+05 | 6.03E−04 | 0.0525 | 0.9973 |

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

---

The invention claimed is:

1. An antibody, comprising:
an anti-claudin 18.2 (CLDN18.2) unit having binding specificity to a CLDN18.2 protein; and
an anti-4-1BB unit having binding specificity to a 4-1BB protein,
wherein the anti-4-1BB unit comprises a heavy chain variable region (VH) comprising a CDRH1, a CDRH2, and a CDRH3, and a light chain variable region (VL) comprising a CDRL1, a CDRL2 and a CDRL3, wherein:
the CDRH1 comprises the amino acid sequence of SEQ ID NO:1;
the CDRH2 comprises the amino acid sequence of SEQ ID NO:2;
the CDRH3 comprises the amino acid sequence of SEQ ID NO:3, 56, 57, 58, or 59;
the CDRL1 comprises the amino acid sequence of SEQ ID NO:4;
the CDRL2 comprises the amino acid sequence of SEQ ID NO:5; and
the CDRL3 comprises the amino acid sequence of SEQ ID NO:6.

2. The antibody of claim 1, wherein the binding of the anti-4-1BB unit to 4-1BB proteins on a cell does not result in clustering of the 4-1BB proteins, in the absence of the anti-CLDN18.2 unit binding to a CLDN18.2 protein.

3. The antibody of claim 1, further comprising a Fc fragment that has reduced effector function.

4. The antibody of claim 3, wherein the Fc fragment is selected from the group consisting of:
an IgG1 Fc fragment with a L235E mutation,
an IgG1 Fc fragment with a L234A and/or L235A mutation,
an IgG1 Fc fragment with a P329G or P329A mutation,
an IgG4 Fc fragment with a F234A and/or L235A or L235E mutation,
an IgG2 Fc fragment with a H268Q, V309L, A330S, and/or P331S mutation, and
an IgG2 Fc fragment with a V234A, G237A, P238S, H268A, V309L, A330S, and/or P331S mutation (EU numbering).

5. The antibody of claim 1, wherein the VH of the anti-4-1BB unit comprises an amino acid sequence selected from the group consisting of SEQ ID NO:24, 46-50 and 63-66 and the VL of the anti-4-1BB unit comprises an amino acid sequence selected from the group consisting of SEQ ID NO:25, 52-53 and 69-74.

6. The antibody of claim 1, wherein the anti-CLDN18.2 unit comprises a heavy chain variable region (VH) comprising a CDRH1, a CDRH2, and a CDRH3, and a light chain variable region (VL) comprising a CDRL1, a CDRL2 and a CDRL3, wherein:
(a) the CDRH1 comprises the amino acid sequence of SEQ ID NO:7;
the CDRH2 comprises the amino acid sequence of SEQ ID NO:8;
the CDRH3 comprises the amino acid sequence of SEQ ID NO:9;
the CDRL1 comprises the amino acid sequence of SEQ ID NO:10;
the CDRL2 comprises the amino acid sequence of SEQ ID NO:11; and
the CDRL3 comprises the amino acid sequence of SEQ ID NO:12,
(b) the CDRH1 comprises the amino acid sequence of SEQ ID NO:13;
the CDRH2 comprises the amino acid sequence of SEQ ID NO:14;
the CDRH3 comprises the amino acid sequence of SEQ ID NO:15;
the CDRL1 comprises the amino acid sequence of SEQ ID NO:16;
the CDRL2 comprises the amino acid sequence of SEQ ID NO:17; and the CDRL3 comprises the amino acid sequence of SEQ ID NO:18, or
(c) the CDRH1 comprises the amino acid sequence of SEQ ID NO:19;
the CDRH2 comprises the amino acid sequence of SEQ ID NO:20;
the CDRH3 comprises the amino acid sequence of SEQ ID NO:21;
the CDRL1 comprises the amino acid sequence of SEQ ID NO:22;
the CDRL2 comprises the amino acid sequence of SEQ ID NO:11; and
the CDRL3 comprises the amino acid sequence of SEQ ID NO:23.

7. The antibody of claim 6, wherein the VH of the anti-CLDN18.2 unit comprises an amino acid sequence selected from the group consisting of SEQ ID NO:26, 28 and 30, and the VL of the anti-CLDN18.2 unit comprises an amino acid sequence selected from the group consisting of SEQ ID NO:27, 29 and 31.

8. An antibody comprising two first polypeptides and two second polypeptides,
wherein each first polypeptide comprises, from N- to C-terminus, a heavy chain variable region (VH), a CH1, a CH2, a CH3, and a single chain fragment (scFv) having specificity to a 4-1BB protein;
wherein each second polypeptide comprises a light chain variable region (VL) and a CL;
wherein each VH is paired with one of the VL and have specificity to a claudin 18.2 (CLDN18.2) protein; and
wherein the scFv comprises a heavy chain variable region (VH) comprising a CDRH1, a CDRH2, and a CDRH3, and a light chain variable region (VL) comprising a CDRL1, a CDRL2 and a CDRL3, wherein:
the CDRH1 comprises the amino acid sequence of SEQ ID NO:1;
the CDRH2 comprises the amino acid sequence of SEQ ID NO:2;
the CDRH3 comprises the amino acid sequence of SEQ ID NO:3, 56, 57, 58, or 59;
the CDRL1 comprises the amino acid sequence of SEQ ID NO:4;
the CDRL2 comprises the amino acid sequence of SEQ ID NO:5; and
the CDRL3 comprises the amino acid sequence of SEQ ID NO:6.

9. The antibody of claim 8, wherein the VH of the scFv comprises an amino acid sequence selected from the group consisting of SEQ ID NO:24, 46-50 and 63-66 and the VL of the scFv comprises an amino acid sequence selected from the group consisting of SEQ ID NO:25, 52-53 and 69-74.

10. The antibody of claim 8, wherein the VH of the VH/VL pair comprises a CDRH1, a CDRH2, and a CDRH3, and VL of the VH/VL pair comprises a CDRL1, a CDRL2 and a CDRL3, wherein:
(a) the CDRH1 comprises the amino acid sequence of SEQ ID NO:7;
the CDRH2 comprises the amino acid sequence of SEQ ID NO:8;
the CDRH3 comprises the amino acid sequence of SEQ ID NO:9;
the CDRL1 comprises the amino acid sequence of SEQ ID NO:10;
the CDRL2 comprises the amino acid sequence of SEQ ID NO:11; and
the CDRL3 comprises the amino acid sequence of SEQ ID NO:12,
(b) the CDRH1 comprises the amino acid sequence of SEQ ID NO:13;
the CDRH2 comprises the amino acid sequence of SEQ ID NO:14;
the CDRH3 comprises the amino acid sequence of SEQ ID NO:15;
the CDRL1 comprises the amino acid sequence of SEQ ID NO:16;
the CDRL2 comprises the amino acid sequence of SEQ ID NO:17; and
the CDRL3 comprises the amino acid sequence of SEQ ID NO:18, or
(c) the CDRH1 comprises the amino acid sequence of SEQ ID NO:19;
the CDRH2 comprises the amino acid sequence of SEQ ID NO:20;
the CDRH3 comprises the amino acid sequence of SEQ ID NO:21;
the CDRL1 comprises the amino acid sequence of SEQ ID NO:22;
the CDRL2 comprises the amino acid sequence of SEQ ID NO:11; and
the CDRL3 comprises the amino acid sequence of SEQ ID NO:23.

11. The antibody of claim 8, wherein the VH of the VH/VL pair comprises an amino acid sequence selected from the group consisting of SEQ ID NO:26, 28 and 30, and the VL of the VH/VL pair comprises an amino acid sequence selected from the group consisting of SEQ ID NO:27, 29 and 31.

12. The antibody of claim 8, wherein each of the first polypeptides comprises the amino acid sequence of SEQ ID NO:40 and each of the second polypeptides comprises the amino acid sequence of SEQ ID NO:41.

13. The antibody of claim 8, wherein each of the first polypeptides comprises the amino acid sequence of SEQ ID NO:42 and each of the second polypeptides comprises the amino acid sequence of SEQ ID NO:43.

14. The antibody of claim 8, wherein each of the first polypeptides comprises the amino acid sequence of SEQ ID NO:44 and each of the second polypeptides comprises the amino acid sequence of SEQ ID NO:45.

15. One or more polynucleotide encoding the antibody of claim 1.

16. A method for treating cancer in a patient in need thereof, comprising administering to the patient the antibody of claim 1.

17. The method of claim 16, wherein the cancer is an epithelial tumor, or wherein the cancer is selected from the group consisting of bladder cancer, breast cancer, colorectal cancer, endometrial cancer, esophageal cancer, head and neck cancer, kidney cancer, leukemia, liver cancer, lung cancer, lymphoma, melanoma, pancreatic cancer, prostate cancer, and thyroid cancer.

18. The antibody of claim 1, wherein the VH comprises the amino acid sequence of SEQ ID NO:24 and the VL comprises the amino acid sequence of SEQ ID NO:25.

19. The antibody of claim 8, wherein the VH comprises the amino acid sequence of SEQ ID NO:24 and the VL comprises the amino acid sequence of SEQ ID NO:25.

* * * * *